US010988463B2

United States Patent
Dowling et al.

(10) Patent No.: US 10,988,463 B2
(45) Date of Patent: *Apr. 27, 2021

(54) SUBSTITUTED 3-AZABICYCLO[3.1.0]HEXANES AS KETOHEXOKINASE INHIBITORS

(71) Applicant: Pfizer Inc., New York, NY (US)

(72) Inventors: Matthew Dowling, Old Lyme, CT (US); Dilinie Fernando, Jamaica Plain, MA (US); Kentaro Futatsugi, Quincy, MA (US); Kim Huard, Berkeley, CA (US); Thomas Victor Magee, Winchester, MA (US); Brian Raymer, Holliston, MA (US); Andre Shavnya, East Lyme, CT (US); Aaron Smith, North Providence, RI (US); Benjamin Thuma, Old Lyme, CT (US); Andy Tsai, Mystic, CT (US); Meihua Tu, Acton, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/999,295

(22) Filed: Aug. 21, 2020

(65) Prior Publication Data

US 2020/0377482 A1 Dec. 3, 2020

Related U.S. Application Data

(63) Continuation of application No. 16/744,283, filed on Jan. 16, 2020, which is a continuation of application No. 16/211,283, filed on Dec. 6, 2018, now abandoned, which is a continuation of application No. 15/729,885, filed on Oct. 11, 2017, now Pat. No. 10,174,007, which is a continuation of application No. 15/381,295, filed on Dec. 16, 2016, now Pat. No. 9,809,579.

(60) Provisional application No. 62/423,549, filed on Nov. 17, 2016, provisional application No. 62/272,598, filed on Dec. 29, 2015.

(51) Int. Cl.

| C07D 401/14 | (2006.01) |
|---|---|
| C07D 403/14 | (2006.01) |
| A61K 31/403 | (2006.01) |
| C07D 401/04 | (2006.01) |
| C07D 403/04 | (2006.01) |

(52) U.S. Cl.
CPC .......... *C07D 403/14* (2013.01); *A61K 31/403* (2013.01); *C07D 401/04* (2013.01); *C07D 401/14* (2013.01); *C07D 403/04* (2013.01)

(58) Field of Classification Search
CPC ... C07D 401/14; C07D 403/14; A61K 31/403
USPC ................ 544/323; 546/276.7; 514/275, 339
See application file for complete search history.

(56) References Cited

U.S. PATENT DOCUMENTS

| 4,980,350 | A | 12/1990 | MacCoss et al. |
|---|---|---|---|
| 5,571,815 | A | 11/1996 | Schaper et al. |
| 6,596,727 | B1 | 7/2003 | Schaper et al. |
| 8,288,385 | B2 | 10/2012 | Caroff et al. |
| 9,387,245 | B2 | 7/2016 | Johnson et al. |
| 9,809,579 | B2 | 11/2017 | Dowling et al. |
| 10,174,007 | B2 * | 1/2019 | Dowling ............... A61P 1/16 |
| 2018/0037575 | A1 | 2/2018 | Dowling et al. |

FOREIGN PATENT DOCUMENTS

| CL | 200600669 | 3/2006 |
|---|---|---|
| CL | 200700906 | 3/2007 |
| CL | 201102467 | 10/2011 |
| CL | 201503290 | 3/2015 |
| RU | 2011144763 | 5/2013 |
| WO | 199319050 | 9/1993 |
| WO | 2008024902 | 2/2008 |
| WO | 2009049165 | 4/2009 |
| WO | 2011133750 | 10/2011 |
| WO | 2012019188 | 2/2012 |
| WO | 2012041158 | 5/2012 |
| WO | 2015123264 | 8/2015 |

OTHER PUBLICATIONS

Chilean Patent Application No. 01667-2018, Examination Report, dated Jun. 19, 2018, 10 pages.
Maryanoff, et al., "Pyrimidinopyrimidine inhibitors of ketohexokinase: Exploring the ring C2 group that interacts with Asp-27B in the ligand binding pocket", Bioorg. Med. Chem. Lett., 2012, pp. 5326-5329, 22(16).
Maryanoff, et al., "Inhibitors of Ketohexokinase: Discovery of Pyrimidinopyrimidines with Specific Substitution that Complements the ATP-Binding Site", ACS Medicinal Chemistry Letters, 2011, pp. 538-543, 2(7).
Russian Patent Application No. 2018123528, Search Report, dated Feb. 13, 2019, 2 pages.
Zhang et al., "Optimization of a pyrazole hit from FBDD into a novel series of indazoles as ketokexokinase inhibitors", Bioorg. Med. Chem. Lett., 2011, pp. 4762-4767, vol. 21.

* cited by examiner

*Primary Examiner* — Deepak R Rao
(74) *Attorney, Agent, or Firm* — Richard V. Zanzalari

(57) ABSTRACT

Provided herein are substituted 3-azabicyclo[3.1.0]hexanes as ketohexokinase inhibitors, processes to make said compounds, and methods comprising administering said compounds to a mammal in need thereof.

8 Claims, 5 Drawing Sheets

Structures of Examples in Table 4

Continued

Continued

SUBSTITUTED 3-AZABICYCLO[3.1.0]HEXANES AS KETOHEXOKINASE INHIBITORS

CROSS REFERENCE TO PRIOR APPLICATIONS

This application is a CONTINUATION of application Ser. No. 16/744,283, filed Jan. 16, 2020 which claims the benefit of CONTINUATION of application Ser. No. 16/211,283, filed Dec. 6, 2018 which claims the benefit of CONTINUATION application Ser. No. 15/729,885, filed Oct. 11, 2017, which claims the benefit of CONTINUATION application Ser. No. 15/381,295, filed Dec. 16, 2016, which claims the benefit of U.S. Provisional Application Ser. No. 62/423,549, filed Nov. 17, 2016 and U.S. Provisional Application Ser. No. 62/272,598, filed Dec. 29, 2015, under 35 USC 119(e), the disclosures of which are hereby incorporated in their entirety.

FIELD OF THE INVENTION

Provided herein are substituted 3-azabicyclo[3.1.0] hexanes as ketohexokinase inhibitors, processes to make said compounds, and methods comprising administering said compounds to a mammal in need thereof.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2D) usually begins with either insulin resistance or when there is insufficient production of insulin to maintain an acceptable glucose level.

Although T2D is most commonly associated with hyperglycemia and insulin resistance, other diseases associated with T2D include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion do.

Recent human data suggests that fructose consumption may contribute to the development of NAFLD/NASH (Vos, M. B., and Lavine, J. E. (2013, *Hepatology* 57, 2525-2531). Compared to glucose, fructose significantly elevates de novo lipid synthesis (Stanhope, K. L., Schwarz, et al., (2009), *J Clin Invest* 119, 1322-1334), a distinct characteristic of patients with NAFLD (Lambert, J. E., et al., (2014), *Gastroenterology* 146, 726-735). Studies in humans have demonstrated that short term fructose feeding causes increases in hepatic triglycerides and that removal of fructose consumption can reverse hepatic triglyceride accumulation (Schwarz, J. M., Noworolski, et al., (2015), *J Clin Endocrinol Metab* 100, 2434-2442). Moreover, in adolescents with NAFLD, 50% reduction of sugar intake for 10 days reduced hepatic triglyceride by 20% (Schwarz, J. M., Noworolski, et al., (2015) PP07-3: Isocaloric Fructose Restriction for 10 Days Reduces Hepatic De Novo Lipogenesis and Liver Fat in Obese Latino and African American Children. http://press.endocrine.org.proxy1.athensams.net/doi/abs/10.1210/endo-meetings.2015.OABA.6.PP07-3).

The high prevalence of T2D, obesity and NAFLD/NASH and associated co-morbidities, such as cardiovascular disease and stroke, has led to increased desire for both preventive care and therapeutic interventions. Current pharmacotherapies for T2D range in strategy to include agents that increase insulin secretion, impact insulin action (thiazolidinediones (TZD), biguanides), alter lipid metabolism (TZD's, fibrates), affect central-feeding behavior, promote urinary glucose excretion (SGLT2 inhibitors) and reduce nutrient absorption (lipase inhibitors). Inhibiting KHK metabolism of fructose offers a novel alternative to current treatment strategies.

Ketohexokinase (KHK) is the principle enzyme in fructose metabolism and catalyzes the conversion of fructose to fructose-1-phosphate (F1P). KHK is expressed as two alternative mRNA splice variants, denoted KHKa and KHKc, resulting from alternative splicing of the third exon. The affinity and capacity of KHKc for fructose phosphorylation is much greater than KHKa as evidenced by a much lower Km (Ishimoto, Lanaspa et al., *PNAS* 109, 4320-4325, 2012). While KHKa is ubiquitously expressed, the expression of KHKc is highest in the liver, kidney and intestines, the primary sites of fructose metabolism in the body (Diggle C P, et al. (2009) *J Histochem Cytochem* 57:763-774; Ishimoto, Lanaspa, et al., *PNAS* 109, 4320-4325, 2012). Additionally, loss of function mutations have been reported in humans with no adverse effects except the appearance of fructose in the urine after ingestion of the sugar.

A more severe condition involved in fructose metabolism is Hereditary Fructose Intolerance (HFI, OMIM #229600) which is caused by defects in aldolase B (GENE: ALDOB) which is the enzyme responsible for breaking down F1P and is immediately downstream of the KHK step in the pathway (Bouteldja N, et. al, *J. Inherit. Metab. Dis.* 2010 April; 33(2):105-12; Tolan, D R, *Hum Mutat.* 1995; 6(3):210-8; http://www.omim.org/entry/229600). It is a rare disorder which affects an estimated 1 in 20,000 people, and mutations result in accumulation of F1P, depletion of ATP, and increase in uric acid, the combination of which causes hypoglycemia, hyperuricemia, and lactic acidosis, among other metabolic derangements. HFI impairs the body's ability to metabolize dietary fructose resulting in acute symptoms such as vomiting, severe hypoglycemia, diarrhea, and abdominal distress, leading to long term growth defects, liver and kidney damage and potentially death (Ali M et al, *J. Med. Genet.* 1998 May: 35(5):353-65). Patients generally suffer through the first years of life prior to diagnosis, and the only course of treatment is avoiding fructose in the diet. This is made challenging by the presence of this macronutrient in a majority of food items. In addition to physical symptoms, many patients experience emotional and social isolation as a consequence of their unusual diet, and constantly struggle to adhere to strict dietary limitations (HFI-INFO Discussion Board, http://hfiinfo.proboards.com. Accessed 14 Dec. 2015). Even when they appear non-symptomatic, some patients develop NAFLD and kidney disease, which underscores the inadequacy of self-imposed dietary restriction as the only treatment option, and the high unmet medical need for this condition.

In hyperglycemic conditions, endogenous fructose production occurs through the polyol pathway, a pathway by which glucose is converted to fructose with sorbitol as an intermediate. The activity of this pathway increases with hyperglycemia. In these studies, the authors demonstrated that the KHK null mice were protected from glucose induced weight gain, insulin resistance and hepatic steatosis suggesting that under hyperglycemic conditions, endogenously produced fructose may contribute to insulin resistance and hepatic steatosis (Lanaspa, M. A., et al., *Nature Comm.* 4, 2434, 2013). Therefore, the inhibition of KHK is anticipated to benefit many diseases where alterations of either or both of endogenous or ingested fructose are involved.

There remains a need for an easily administered treatment for cardiometabolic and associated diseases including diabetes (T1D and/or T2D), idiopathic T1D (Type 1 b), latent autoimmune diabetes in adults (LADA), early-onset T2D (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, obesity, eating disorders, excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), HFI, coronary artery disease, peripheral vascular disease, hypertension, endothelial dysfunction, impaired vascular compliance, congestive heart failure, myocardial infarction (e.g. necrosis and apoptosis), stroke, hemorrhagic stroke, ischemic stroke, pulmonary hypertension, restenosis after angioplasty, intermittent claudication, post-prandial lipemia, metabolic acidosis, ketosis, arthritis, osteoporosis, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, foot ulcerations, ulcerative colitis, hyper apo B lipoproteinemia, Alzheimer's Disease, schizophrenia, impaired cognition, inflammatory bowel disease, ulcerative colitis, Crohn's disease, and irritable bowel syndrome.

DETAILED DESCRIPTION OF THE INVENTION

Figure 1:
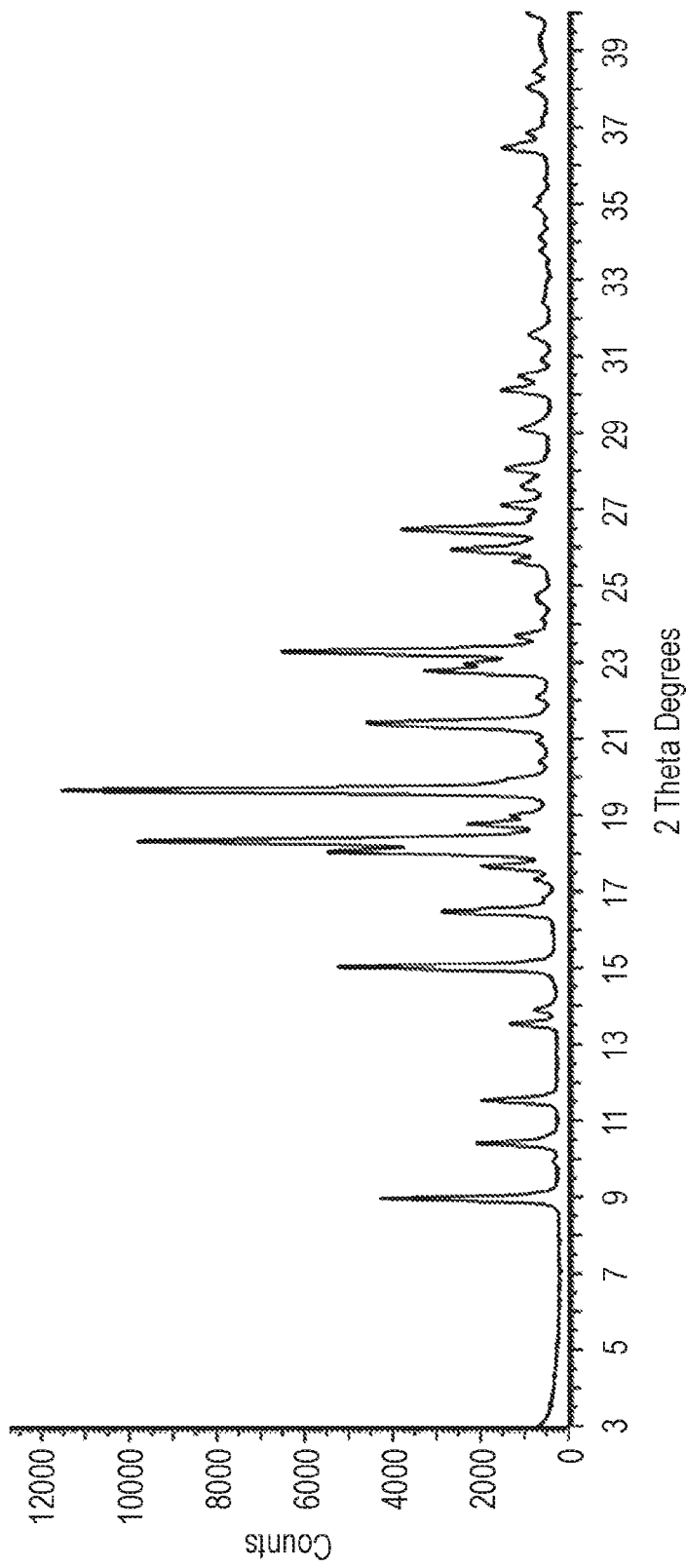
FIG. 1 provides the PXRD pattern of crystalline free acid of Example 4.

The present invention concerns compounds of Formula I

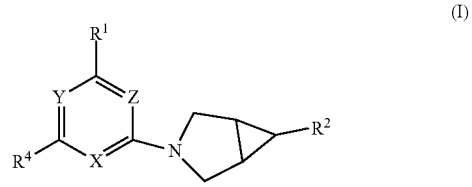

or a pharmaceutically salt thereof, wherein
Y is N or C—CN;
Z is N or CH;
X is N or CR$^3$;
provided that at least one of Y, Z, or X is N;
R$^1$ is C$_{3-7}$cycloalkyl or a 4- to 7-membered heterocyclic moiety, wherein the heterocyclic moiety contains 1 to 2 atoms independently selected from nitrogen, oxygen and sulfur, and wherein the cycloalkyl or heterocyclic moiety has 0 to 3 substitutents independently selected from —C$_{1-3}$alkyl and —OH, wherein —C$_{1-3}$alkyl is substituted with 0 to 3 halogen atoms, and provided that there is no more than one —OH substituent; or
N(C$_{1-3}$alkyl)$_2$, NH(C$_{1-3}$alkyl), or NH(C$_{3-4}$cycloalkyl), wherein each C$_{1-3}$alkyl is substituted with 0 to 1 OH;
R$^2$ is -(L)$_m$-CON(R$^N$)$_2$, -(L)$_m$-SO$_2$R$^S$, -L-(CH$_2$)$_n$SO$_2$R$^S$, -L-(CH$_2$)$_n$CO$_2$H, -L-(CH$_2$)$_n$C(O)R$^C$, -L-(CH$_2$)$_n$CONHSO$_2$R$^S$, -L-(CH$_2$)$_n$SO$_2$NHCOR$^S$, -L-(CH$_2$)$_n$SO$_2$NHCONH$_2$, or -L-(CH$_2$)$_n$tetrazol-5-yl;
m is 0 or 1;
n is 0 or 1;
R$^N$ is H or —C$_{1-3}$alkyl;
R$^S$ is H or —C$_{1-3}$alkyl;
L is CH$_2$, CHF, or CF$_2$;
R$^C$ is —C$_{1-4}$alkyloxy, —C$_{1-4}$alkyloxycarbonyloxy-C$_{1-4}$alkyloxy, or —C$_{1-4}$alkylcarbonyloxy-C$_{1-4}$alkyloxy;
R$^3$ is H, halogen, —CN, —C$_{1-3}$alkyl, —OC$_{1-3}$alkyl, —C$_{1-3}$alkyl substituted with 1 to 3 halogen atoms, or —C$_{3-4}$cycloalkyl; and
R$^4$ is cyclopropyl, cyclobutyl, or —C$_{1-3}$alkyl substituted with 0 to 5 halogen atoms as valency allows.

Another embodiment concerns compounds of Formula I, or a pharmaceutically acceptable salt thereof, wherein X, Y and Z provide any one of the following:

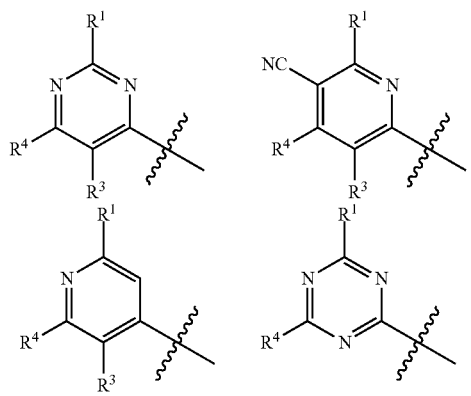

-continued

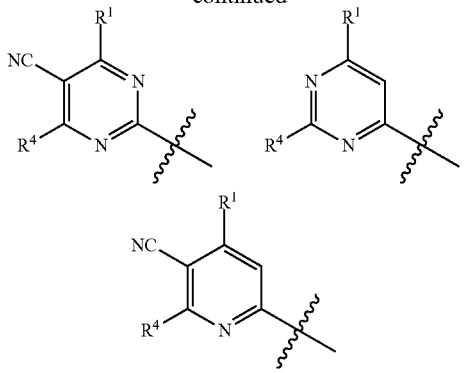

Another embodiment concerns compounds of Formula I, or a pharmaceutically acceptable salt thereof, wherein
Y is N or C—CN;
Z is N or CH;
X is $CR^3$;
provided that at least one of Y or Z is N;
$R^1$ is $C_{3-7}$cycloalkyl or a 4- to 7-membered heterocyclic moiety, wherein the heterocyclic moiety contains 1 to 2 atoms independently selected from nitrogen, oxygen and sulfur, and wherein the cycloalkyl or heterocyclic moiety has 0 to 3 substitutents independently selected from —$C_{1-3}$ alkyl and —OH, wherein —$C_{1-3}$alkyl is substituted with 0 to 3 F atoms (wherein halogen is F), and provided that there is no more than one —OH substituent; or
$N(C_{1-3}alkyl)_2$, $NH(C_{1-3}alkyl)$, or $NH(C_{3-4}cycloalkyl)$, wherein each $C_{1-3}$alkyl is substituted with 0 to 1 OH;
$R^2$ is -$(L)_m$-CON$(R^N)_2$, -$(L)_m$-SO$_2R^S$, -L-$(CH_2)_n$SO$_2R^S$, -L-$(CH_2)_nCO_2H$, -L-$(CH_2)_nC(O)R^C$, -L-$(CH_2)_n$CONHSO$_2R^S$, -L-$(CH_2)_n$SO$_2$NHCOR$^S$, -L-$(CH_2)_n$SO$_2$NHCONH$_2$, or -L-$(CH_2)_n$tetrazol-5-yl;
m is 0 or 1;
n is 0 or 1;
$R^N$ is H or —$C_{1-3}$alkyl;
$R^S$ is H or —$C_{1-3}$alkyl;
L is $CH_2$, CHF, or $CF_2$;
$R^C$ is —$C_{1-4}$alkyloxy, —$C_{1-4}$alkyloxycarbonyloxy-$C_{1-4}$alkyloxy, or —$C_{1-4}$alkylcarbonyloxy-$C_{1-4}$alkyloxy;
$R^3$ is H, halogen, —CN, —$C_{1-3}$alkyl, —$OC_{1-3}$alkyl, —$C_{1-3}$alkyl substituted with 1 to 3 halogen atoms, or —$C_{3-4}$cycloalkyl; and
$R^4$ is —$C_{1-3}$alkyl substituted with 0 to 5 halogen atoms as valency allows.

Another embodiment concerns compounds of Formula I, or a pharmaceutically salt thereof, wherein
Y is C—CN;
Z is N;
X is $CR^3$;
$R^1$ is $C_{3-7}$cycloalkyl or a 4- to 7-membered heterocyclic moiety, wherein the heterocyclic moiety contains 1 to 2 atoms independently selected from nitrogen, oxygen and sulfur, and wherein the cycloalkyl or heterocyclic moiety has 0 to 3 substitutents independently selected from —$C_{1-3}$ alkyl and —OH, provided that there is no more than one —OH substituent;
$R^2$ is -$(L)_m$-CON$(R^N)_2$, -$(L)_m$-SO$_2R^S$, -L-$(CH_2)_n$SO$_2R^S$, -L-$(CH_2)_nCO_2H$, -L-$(CH_2)_nC(O)R^C$, -L-$(CH_2)_n$CONHSO$_2R^S$, -L-$(CH_2)_n$SO$_2$NHCOR$^S$, or -L-$(CH_2)_n$tetrazol-5-yl;
m is 0 or 1;
n is 0 or 1;
$R^N$ is H or —$C_{1-3}$alkyl;
$R^S$ is H or —$C_{1-3}$alkyl;
L is $CH_2$, CHF, or $CF_2$;
$R^C$ is —$C_{1-4}$alkyloxy, —$C_{1-4}$alkyloxycarbonyloxy-$C_{1-4}$alkyloxy, or —$C_{1-4}$alkylcarbonyloxy-$C_{1-4}$alkyloxy;
$R^3$ is H, halogen, —CN, —$C_{1-3}$alkyl substituted with 1 to 3 halogen atoms, or —$C_{3-4}$cycloalkyl; and
$R^4$ is —$C_{1-3}$alkyl substituted with 0 to 5 halogen atoms as valency allows.

Another embodiment concerns compounds of Formula I, or a pharmaceutically acceptable salt thereof, wherein
Y is N;
Z is N;
X is $CR^3$;
$R^1$ is $C_{3-7}$cycloalkyl or a 4- to 7-membered heterocyclic moiety, wherein the heterocyclic moiety contains 1 to 2 atoms independently selected from nitrogen, oxygen and sulfur, and wherein the cycloalkyl or heterocyclic moiety has 0 to 3 substitutents independently selected from —$C_{1-3}$ alkyl, and —OH, provided that there is no more than one —OH substituent;
$R^2$ is -$(L)_m$-CON$(R^N)_2$, -$(L)_m$-SO$_2R^S$, -L-$(CH_2)_n$SO$_2R^S$, -L-$(CH_2)_nCO_2H$, -L-$(CH_2)_nC(O)R^C$, -L-$(CH_2)_n$CONHSO$_2R^S$, -L-$(CH_2)_n$SO$_2$NHCOR$^S$, or -L-$(CH_2)_n$tetrazol-5-yl;
m is 0 or 1;
n is 0 or 1;
$R^N$ is H or —$C_{1-3}$alkyl;
$R^S$ is H or —$C_{1-3}$alkyl;
L is $CH_2$, CHF, or $CF_2$;
$R^C$ is —$C_{1-4}$alkyloxy, —$C_{1-4}$alkyloxycarbonyloxy-$C_{1-4}$alkyloxy, or —$C_{1-4}$alkylcarbonyloxy-$C_{1-4}$alkyloxy;
$R^3$ is H, halogen, —CN, —$C_{1-3}$alkyl, —$OC_{1-3}$alkyl, —$C_{1-3}$alkyl substituted with 1 to 3 halogen atoms, or —$C_{3-4}$cycloalkyl; and
$R^4$ is —$C_{1-3}$alkyl substituted with 0 to 5 halogen atoms as valency allows.

Another embodiment concerns compounds of Formula I, or a pharmaceutically acceptable salt thereof, wherein
Y is N of C—CN;
Z is N of CH;
X is $CR^3$;
provided at least one of Y or Z is N;
$R^1$ is $C_{3-7}$cycloalkyl or a 4- to 7-membered heterocyclic moiety, wherein the heterocyclic moiety contains 1 to 2 atoms independently selected from nitrogen, oxygen and sulfur, and wherein the cycloalkyl or heterocyclic moiety has 0 to 3 substitutents independently selected from —$C_{1-3}$ alkyl, and —OH, provided that there is no more than one —OH substituent;
$R^2$ is -$(L)_m$-CON$(R^N)_2$, -$(L)_m$-SO$_2R^S$, -L-$(CH_2)_n$SO$_2R^S$, -L-$(CH_2)_nCO_2H$, -L-$(CH_2)_nC(O)R^C$, -L-$(CH_2)_n$CONHSO$_2R^S$, -L-$(CH_2)_n$SO$_2$NHCOR$^S$, or -L-$(CH_2)_n$tetrazol-5-yl;
m is 0 or 1;
n is 0 or 1;
$R^N$ is H or —$CH_3$;
$R^S$ is H or —$CH_3$;
L is $CH_2$, CHF, or $CF_2$;
$R^C$ is —$C_{1-4}$alkyloxy, —$C_{1-4}$alkyloxycarbonyloxy-$C_{1-4}$alkyloxy, or —$C_{1-4}$alkylcarbonyloxy-$C_{1-4}$alkyloxy;
$R^3$ is H, —Cl, —$CH_3$, —$CH_2CH_3$, —O—$CH_3$, cyclopropyl, or CN; and
$R^4$ is —$CF_3$, —$CHF_2$, or —$CF_2CH_3$.

Another embodiment concerns any other embodiment discussed herein regarding compounds of Formula I, or a pharmaceutically salt thereof, wherein $R^N$ is H or —$CH_3$.

Another embodiment concerns any other embodiment discussed herein regarding compounds of Formula I, or a pharmaceutically salt thereof, wherein $R^S$ is H or —$CH_3$.

Another embodiment concerns any other embodiment discussed herein regarding compounds of Formula I, or a pharmaceutically salt thereof, wherein $R^2$ is —$CH_2CO_2H$ (n is 0 and L is $CH_2$). Another embodiment concerns any other embodiment discussed herein regarding compounds of Formula I, or a pharmaceutically salt thereof, wherein $R^2$ is —$CH_2CO_2H$, —$CH_2CO_2CH_3$, or —$CH_2CO_2CH_2CH_3$ (n is 0, $R^c$ is $OCH_3$ or $OCH_2CH_3$ when present, and L is $CH_2$). Another embodiment concerns any other embodiment discussed herein regarding compounds of Formula I, or a pharmaceutically salt thereof, wherein $R^2$ is —$CH_2CH_2CO_2H$, —$CH_2CH_2CO_2CH_3$, or —$CH_2CH_2CO_2CH_2CH_3$ (n is 1, $R^c$ is $OCH_3$ or $OCH_2CH_3$ when present, and L is $CH_2$).

Another embodiment concerns any other embodiment discussed herein regarding compounds of Formula I, or a pharmaceutically salt thereof, wherein $R^2$ is -(L)$_m$-CON(R$^N$)$_2$, -(L)$_m$-SO$_2$R$^S$, -L-(CH$_2$)$_n$SO$_2$R$^S$, -L-(CH$_2$)$_n$CO$_2$H, -L-(CH$_2$)$_n$C(O)R$^S$, -L-(CH$_2$)$_n$CONHSO$_2$R$^C$, -L-(CH$_2$)$_n$SO$_2$NHCOR$^S$, or -L-(CH$_2$)$_n$tetrazol-5-yl.

Another embodiment concerns any other embodiment discussed herein regarding compounds of Formula I, or a pharmaceutically salt thereof, wherein $R^2$ is H, —Cl, —$CH_3$, —$CH_2CH_3$, —O—$CH_3$, cyclopropyl, or CN.

Another embodiment concerns any other embodiment discussed herein regarding compounds of Formula I, or a pharmaceutically salt thereof, wherein $R^4$ is —$CF_3$, —$CHF_2$, or —$CF_2CH_3$.

Another embodiment concerns any other embodiment discussed herein regarding compounds of Formula I, or a pharmaceutically salt thereof, wherein $R^1$ is cyclobutyl ($C_4$ cycloalkyl) having 0 to 3 substitutents independently selected from —$CH_3$ and —OH, provided that there is no more than one —OH substituent.

Another embodiment concerns any other embodiment discussed herein regarding compounds of Formula I, or a pharmaceutically salt thereof, wherein $R^1$ is the 4- to 7-membered heterocyclic moiety selected from azetidin-1-yl, pyrrolidin-1-yl, and piperidin-1-yl ($R^1$ being the 4- to 7-membered heterocyclic moiety) having 0 to 3 substitutents independently selected from —$CH_3$ and —OH, provided that there is no more than one —OH substituent.

A preferred embodiment concerns compounds of Formula I, or a pharmaceutically salt thereof, wherein X, $R^2$, m, n, $R^N$, $R^S$, L, $R^C$, $R^3$, and $R^4$ have any embodiment described herein, wherein $R^1$ is azetidin-1-yl, pyrrolidin-1-yl, and piperidin-1-yl having 0 to 2 —$CH_3$ substituents and having 0 to 1 —OH substituent, and wherein Y is C—CN and Z is N, or Y and Z are each N.

Another preferred embodiment concerns compounds of Formula I, or a pharmaceutically salt thereof, wherein X, $R^2$, m, n, $R^N$, $R^S$, L, $R^C$, $R^3$, and $R^4$ have any embodiment described herein, wherein $R^1$ is azetidin-1-yl, having 1 to 2 —$CH_3$ substituents and having 0 to 1 —OH substituent, and wherein Y is C—CN and Z is N, or Y and Z are each N.

Another embodiment concerns compounds of Formula I, or a pharmaceutically salt thereof, wherein Y is C—CN and Z is N, or Y and Z are each N.

Another embodiment of the invention concerns compounds of Formula I(a)

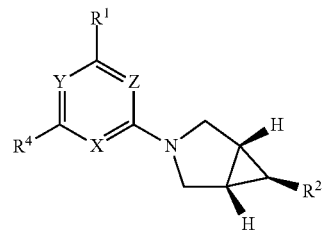

(Ia)

or a pharmaceutically salt thereof, wherein the $R^2$ substituent on azabicyclo[3.1.0]hex-6-yl and H atoms at the bridge carbons are in the same plane, and wherein X, Y, Z, $R^2$, m, n, $R^N$, $R^S$, L, $R^C$, $R^3$, and $R^4$ have any embodiment described herein.

Another embodiment of the invention concerns compounds of Formula I(b)

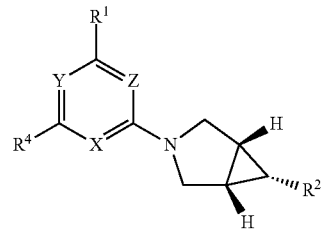

(Ib)

or a pharmaceutically salt thereof, wherein the $R^2$ substituent on azabicyclo[3.1.0]hex-6-yl and H atoms at the bridge carbons are in the same plane, and wherein X, Y, Z, $R^2$, m, n, $R^N$, $R^S$, L, $R^C$, $R^3$, and $R^4$ have any embodiment described herein.

The term "alkyl", as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl, and hexyl.

The term "cycloalkyl", as used herein, means a cyclic, monovalent hydrocarbon group of formula —$C_nH_{(2n-1)}$ containing at least three carbon atoms. Non-limiting examples include cyclopropyl, cyclobutyl, cyclopentyl, and cyclohexyl.

The term "alkyloxy", as used herein, means an alkyl substituent attached through an oxygen atom. Non-limiting examples include methoxy, ethoxy, propoxy, and butoxy.

The term "alkyloxycarbonyloxy", as used herein, means an alkoxy group attached through a carbonyl group (—CO—). Non-limiting examples include methoxycarbonyl, ethoxycarbonyl, and propoxycarbonyl.

The term "alkylcarbonyloxy", as used herein, means an alkyl group attached through a carbonyloxy group (—C(=O)—O—). Representative examples include methylcarbonyloxy, ethylcarbonyloxy, and tert-butylcarbonyloxy.

The term "alkyloxycarbonyloxy-alkyloxy" as used herein, means an alkyloxycarbonyloxy group attached through an alkyloxy group.

The term "halogen", as used herein, refers to F, Cl, Br, I.

The term "heterocyclic moiety", as used herein, refers to a cycloalkyl group having 4 to 7 carbon atoms in which one or more of the ring methylene groups (—$CH_2$—) has been replaced with a group selected from —O—, —S— or —N—, where valency requirements for —N— are satisfied with H or being a point of attachment.

Common abbreviations used herein:
ADP is adenosine diphosphate;
ATP is adenosine triphosphate;
$CDCl_3$ is deuterochloroform;
$CO_2Et$ is ethyl carboxylate;
DCM is dichloromethane;
DIPEA is N,N-diisopropylethylamine;
DMF is dimethylformamide;
DMSO is dimethylsulfoxide;
EtOAc is ethyl acetate;
H or h or hr is for hour(s);
HEPES is 4-(2-hydroxyethyl)-1-piperazine ethanesulfonic acid;
KCl is potassium chloride;
Min is for minute(s);
$MgCl_2$ is magnesium chloride;
$NaHCO_3$ is Sodium bicarbonate;
$Na_2SO_4$ is sodium sulfate
NADH is nicotinamide adenine dinucleotide (reduced form)
$NAD^+$ is nicotinamide adenine dinucleotide (oxidized form)
PEP is phosphoenolpyruvate;
RT or rt is room temperature;
TCEP is tris(2-carboxyethyl)phosphine;
TFA is trifluoroacetic acid;
THF is tetrahydrofuran.

Another embodiment concerns compounds of Formula I, or a pharmaceutically salt thereof, wherein each compound is independently selected from any one or more Example provided herein.

One way of carrying out the invention is to administer a compound of Formula (I) in the form of a prodrug. Thus, certain derivatives of a compound of Formula (I) which may have little or no pharmacological activity themselves can, when administered into or onto the body, would be converted into a compound of Formula (I) having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of Formula (I) with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a carboxylic acid in a compound of Formula (I); (b) an ester, carbonate, carbamate, phosphate or ether derivative of a hydroxyl group in a compound of Formula (I); (c) an amide, imine, carbamate or amine derivative of an amino group in a compound form Formula (I); (d) a thioester, thiocarbonate, thiocarbamate or sulfide derivatives of a thiol group in a compound of Formula (I); or (e) an oxime or imine derivative of a carbonyl group in a compound of Formula (I).

Some specific examples of prodrugs in accordance with the invention include where $R^2$ is -L-$(CH_2)_n$C(O)$R^C$. The following provides more general guidance on prodrugs of this invention:

(i) where the compound of Formula (I) contains a carboxylic acid functionality (—COOH), an ester thereof, such as a compound wherein the hydrogen of the carboxylic acid functionality of the compound of Formula (I) is replaced by $C_{1-8}$alkyl (e.g. ethyl) or $(C_{1-8}$ alkyl)C(=O)OCH$_2$— (e.g. tBuC(=O)OCH$_2$—);

(ii) where the compound of Formula (I) contains an alcohol functionality (—OH), an ester thereof, such as a compound wherein the hydrogen of the alcohol functionality of the compound of Formula (I) is replaced by —CO($C_{1-8}$alkyl) (e.g. methylcarbonyl) or the alcohol is esterified with an amino acid;

(iii) where the compound of Formula (I) contains an alcohol functionality (—OH), an ether thereof, such as a compound wherein the hydrogen of the alcohol functionality of the compound of Formula (I) is replaced by $(C_{1-8}$alkyl)C(=O)OCH$_2$— or —CH$_2$OP(=O)(OH)$_2$;

(iv) where the compound of Formula (I) contains an alcohol functionality (—OH), a phosphate thereof, such as a compound wherein the hydrogen of the alcohol functionality of the compound of Formula (I) is replaced by —P(=O)(OH)$_2$ or —P(=O)(ONa)$_2$ or —P(=O)(O—)$_2$Ca$^{2+}$;

(v) where the compound of Formula (I) contains a primary or secondary amino functionality (—NH$_2$ or —NHR where R≠H), an amide thereof, for example, a compound wherein, as the case may be, one or both hydrogens of the amino functionality of the compound of Formula (I) is/are replaced by $(C_{1-10})$alkanoyl, —COCH$_2$NH$_2$ or the amino group is derivatised with an amino acid;

(vi) where the compound of Formula (I) contains a primary or secondary amino functionality (—NH$_2$ or —NHR where R≠H), an amine thereof, for example, a compound wherein, as the case may be, one or both hydrogens of the amino functionality of the compound of Formula (I) is/are replaced by —CH$_2$OP(=O)(OH)$_2$.

Certain compounds of Formula (I) may themselves act as prodrugs of other compounds of Formula (I). It is also possible for two compounds of Formula (I) to be joined together in the form of a prodrug. In certain circumstances, a prodrug of a compound of Formula (I) may be created by internally linking two functional groups in a compound of Formula (I), for instance by forming a lactone.

As used herein, the term "Formula I" may be referred to as a "compound(s) of the invention," "compound(s) of the present invention," "the invention," and "compound of Formula I." Such terms are used interchangeably. Furthermore, it is intended that the embodiments discussed herein with reference to Formula I also concern compounds of Formula I(a) or Formula I(b). Such terms are also defined to include all forms of the compound of Formula I, including hydrates, solvates, clathrates, isomers, crystalline (including co-crystals) and non-crystalline forms, isomorphs, polymorphs, tautomers, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see *Chem Commun*, 17, 1889-1896, by O. Almarsson and M. J. Zaworotko (2004). For a general review of multi-component complexes, see *J Pharm Sci*, 64 (8), 1269-1288, by Haleblian (August 1975).

The compounds of the invention may contain asymmetric or chiral centers, and, therefore, exist in different stereoisomeric forms. Unless specified otherwise, it is intended that all stereoisomeric forms of the compounds of the invention as well as mixtures thereof, including racemic mixtures, form part of the present invention. In addition, the invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the invention possess one or more stereogenic centers and no stereochemistry is given in the name or structure, it is understood that the name or structure is intended to encompass all forms of the compound, including the racemic form. Where the compounds of the invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Stereogenic centers of molecules may be represented by multiple, alternate combinations of solid and dashed wedges. Many Examples provided herein may include a 3.1.0 ring system with meso stereochemistry as defined by IUPAC naming rules or the Cahn-Ingold-Prelog conventions, which have been used in naming Examples and intermediates, and utilizing ChemBioDraw Ultra 14.0.0.117 and/or ACD/Name Software v12.0. It should be noted that bonds may be wedged or dashed while representing the same stereochemistry, e.g., compare, Examples 1 and 54, due to rotation at the bond between the nitrogen of the 3.1.0 moiety and core moiety and which can also occur between the bond from the core moiety and $R^1$, where the core moiety is pyridinyl, pyrimidinyl, or triazinyl depending on the definitions of X, Y, and Z.

In another embodiment, the invention provides a pharmaceutical composition comprising a compound of Formula I, or a pharmaceutically acceptable salt thereof, as defined in any of the embodiments described herein, in admixture with at least one pharmaceutically acceptable excipient.

The present invention also provides any one or combination of:

a method of treating a disease for which an inhibitor of KHK is indicated, in a subject in need of such treatment, comprising administering to the subject a therapeutically effective amount of a compound of Formula I, or a pharmaceutically acceptable salt thereof;

the use of a compound of Formula I, or a pharmaceutically acceptable salt thereof, for the manufacture of a medicament for treating a disease for which an inhibitor of KHK is indicated;

a compound of Formula I, or a pharmaceutically acceptable salt thereof, for use as a medicament;

a compound of Formula I, or a pharmaceutically acceptable salt thereof, for use in the treatment of a disease for which an inhibitor of KHK is indicated;

a pharmaceutical composition comprising a compound of Formula I, or a pharmaceutically acceptable salt thereof, and a pharmaceutically acceptable excipient;

a pharmaceutical composition for the treatment of a disease for which an inhibitor of KHK is indicated, comprising a compound of Formula I, or a pharmaceutically acceptable salt thereof.

As used herein, treatment of a disease for which an inhibitor of KHK is indicated means that at least one compound of Formula I, or a pharmaceutically acceptable salt thereof, is administered to a patient in need thereof to treat, or used to prepare a medicament to treat a patient in need thereof, by inhibiting KHK and the subsequent metabolism of fructose, to treat a disease, disorder, condition, or associated co-morbidity (referred to generally herein as a disease) selected from any one or more of the following: T1D, T2D, idiopathic T1D, LADA, EOD, YOAD, MODY, malnutrition-related diabetes, gestational diabetes, hyperglycemia, insulin resistance, hepatic insulin resistance, impaired glucose tolerance, diabetic neuropathy, diabetic nephropathy, kidney disease, acute kidney disorder, tubular dysfunction, proinflammatory changes to the proximal tubules, diabetic retinopathy, adipocyte dysfunction, visceral adipose deposition, obesity, eating disorders, excessive sugar craving, dyslipidemia, hyperlipidemia, hypertriglyceridemia, increased total cholesterol, high LDL cholesterol, low HDL cholesterol, hyperinsulinemia, NAFLD, steatosis, NASH, fibrosis, cirrhosis, hepatocellular carcinoma, HFI, coronary artery disease, peripheral vascular disease, hypertension, endothelial dysfunction, impaired vascular compliance, congestive heart failure, myocardial infarction, stroke, hemorrhagic stroke, ischemic stroke, pulmonary hypertension, restenosis after angioplasty, intermittent claudication, post-prandial lipemia, metabolic acidosis, ketosis, arthritis, osteoporosis, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, foot ulcerations, ulcerative colitis, hyper apo B lipoproteinemia, Alzheimer's Disease, schizophrenia, impaired cognition, inflammatory bowel disease, ulcerative colitis, Crohn's disease, and irritable bowel syndrome.

In another embodiment, the invention provides a method of treating a disease selected from any one or combination of the following: T1D, T2D, insulin resistance, kidney disease, acute kidney disorder, tubular dysfunction, proinflammatory changes to the proximal tubules, adipocyte dysfunction, visceral adipose deposition, obesity, eating disorders, excessive sugar craving, dyslipidemia, hyperlipidemia, hypertriglyceridemia, increased total cholesterol, high LDL cholesterol, low HDL cholesterol, NAFLD, steatosis, NASH, fibrosis, cirrhosis, hepatocellular carcinoma, HFI, hypertension, endothelial dysfunction, metabolic syndrome, hyperuricemia, and gout.

The invention also relates to a pharmaceutical composition comprising a compound of Formula I, or a pharmaceutically acceptable salt thereof, as defined in any of the embodiments described herein, for use in the treatment of any one or more diseases discussed herein.

In another embodiment, the invention provides a pharmaceutical composition comprising a compound of Formula I, or a pharmaceutically acceptable salt thereof, as defined in any of the embodiments described herein, in admixture with at least one pharmaceutically acceptable excipient.

In another embodiment, the invention provides a pharmaceutical composition comprising a compound of Formula I, or a pharmaceutically acceptable salt thereof, as defined in any of the embodiments described herein, in admixture with at least one other therapeutic agent described herein.

The phrase "therapeutically effective amount" means an amount of a compound of the invention that (i) treats or prevents the particular disease, (ii) attenuates, ameliorates, or eliminates one or more symptoms of the particular disease, or (iii) prevents or delays the onset of one or more symptoms of the particular disease described herein.

The term "mammal" refers to warm blooded animals, including humans (male or female) and companion animals (e.g., dogs, cats, horses, etc.), and other animals including guinea pigs, mice, rats, gerbils, cattle, goats, sheep, monkeys, and chimpanzees.

The term "patient" is an alternative reference for mammal.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment, i.e., relieve, alleviate, or slow the progression of the patient's disease or any tissue damage associated with the disease.

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O.

Certain isotopically-labelled compounds of Formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagents in place of the non-labelled reagent previously employed.

Combination Agents

The compounds of the present invention may be used, alone or in combination with other therapeutic agents, in the treatment of various conditions or diseases. The compound(s) of the present invention and other therapeutic agent(s) may be administered simultaneously (either in the same dosage form or in separate dosage forms) or sequentially.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

In another embodiment, the compounds of this invention are co-administered with any one or more additional therapeutic agent(s) as described herein. The combination agents are administered to a mammal in a therapeutically effective amount to treat the diseases described herein.

The phrases "concurrent administration," "co-administration," "simultaneous administration," and "administered simultaneously" mean that the compounds are administered in combination.

In another embodiment of the present invention, a compound of Formula I may be co-administered with an anti-obesity agent where the anti-obesity agent is selected from the group consisting of gut-selective MTP inhibitors (e.g., dirlotapide, mitratapide and implitapide, R56918 (CAS No. 403987 and CAS No. 913541-47-6)), cholecystokinin-A (CCK-A) agonists (e.g., N-benzyl-2-[4-(1H-indol-3-ylmethyl)-5-oxo-1-phenyl-4,5-dihydro-2,3,6,10b-tetraazabenzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, lipase inhibitors (such as tetrahydrolipstatin, i.e. orlistat), exenatide (Byetta®), AOD-9604 (CAS No. 221231-10-3) and sibutramine.

Other anti-obesity agents include 11β-hydroxy steroid dehydrogenase-1 (11β-HSD type 1) inhibitors, stearoyl-CoA desaturase-1 (SCD-1) inhibitor, monoamine reuptake inhibitors (such as sibutramine), sympathomimetic agents, $β_3$ adrenergic agonists, dopamine agonists (such as bromocriptine), melanocyte-stimulating hormone analogs, melanin concentrating hormone antagonists, leptin (the OB protein), leptin analogs, leptin agonists, galanin antagonists, anorectic agents (such as a bombesin agonist), neuropeptide-Y antagonists (e.g., NPY Y5 antagonists), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors), orexin antagonist, the combination of naltrexone with buproprion and the like.

In another embodiment of the present invention, a compound of Formula I may be co-administered with an anti-diabetic agent, where the anti-diabetic agent is selected from the group consisting of an acetyl-CoA carboxylase- (ACC) inhibitor (e.g., those described in WO2009144554, WO2003072197, WO2009144555 and WO2008065508), a diacylglycerol O-acyltransferase 1 (DGAT-1) inhibitor (e.g., those described in WO09016462 or WO2010086820, AZD7687 or LCQ908), monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767, SB-219994, and saroglitazar), a biguanide (e.g., metformin), a glucagon receptor antagonist, a glucagon-like peptide 1 (GLP-1) modulator such as an agonist (e.g., exendin-3, exendin-4, ZYOG-1 and TTP273), liraglutide (Victoza®), albiglutide, exenatide (Byetta®, Bydureon®), albiglutide, lixisenatide, dulaglutide, semaglutide (NN-9924), TTP-054, a protein tyrosine phosphatase-1B (PTP-1B) inhibitor (e.g., trodusquemine, hyrtiosal extract, and compounds disclosed by Zhang, S., et al., *Drug Discovery Today,* 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) (e.g., those in WO2010103437, WO2010103438, WO2010013161, WO2007122482, TTP-399, TTP-355, TTP-547, AZD1656, ARRY403, MK-0599, TAK-329, AZD5658 or GKM-001), insulin and insulin analogues thereof, an insulin mimetic, a glycogen phosphorylase inhibitor (e.g. GSK1362885), a VPAC2 receptor agonist, SGLT2 inhibitors (e.g., those described in E. C. Chao et al. *Nature Reviews Drug Discovery* 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594), a glucagon receptor modulator such as those described in Demong, D. E. et al. *Annual Reports in Medicinal Chemistry* 2008, 43, 119-137; GPR119 modulators (e.g., particularly agonists, such as those described in WO2010140092, WO2010128425, WO2010128414, WO2010106457, Jones, R. M. et al. in *Medicinal Chemistry* 2009, 44, 149-170 (e.g. MBX-2982, GSK1292263, APD597 and PSN821)), FGF21 derivatives or analogs (e.g., those described in Kharitonenkov, A. et al. et al., *Current Opinion in Investigational Drugs* 2009, 10(4)359-364), TGR5 (also termed GPBAR1) receptor modulators (e.g., and INT777 and agonists, such as those described in Zhong, M., Current Topics in *Medicinal Chemistry,* 2010, 10(4), 386-396), GPR40 agonists (e.g., those described in Medina, J. C., *Annual Reports in Medicinal Chemistry,* 2008, 43, 75-85, including but not limited to TAK-875, GPR120 modulators, particularly agonists, high affinity nicotinic acid receptor (HM74A) activators, and SGLT1 inhibitors, such as GSK1614235 (, listing of anti-diabetic agents (e.g., WO2011005611, in particular, those found at page 28, line 35 through page 30, line 19), inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha, suitable anti-diabetic agents include mechanisms listed by Carpino, P. A., Goodwin, B. Expert *Opin. Ther. Pat,* 2010, 20(12), 1627-51.

In another embodiment of the present invention, a compound of Formula I may be co-administered with agents typically used by those with diabetes, e.g., a thyroid hormone (like Synthroid), any agent for diabetic neuropathy (e.g., gabapentin, amitriptyline) or an agent or agents to treat any type of depression (e.g., fluoxetine, sertraline, paroxetine, escitalopram, citalopram, duloxetine, levomilnacipran, venlafaxine, desvenlafaxine. Bupropion, tricyclic antidepressants, including imipramine, nortriptyline, protriptyline, amitriptyline, doxepin, trimipramine, and desipramine).

In another embodiment of the present invention, a compound of Formula I may be co-administered with a cholesterol/lipid modulating agent, where the cholesterol/lipid modulating agent is selected from the group consisting of HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); HMG-CoA reductase gene expression inhibitor; squalene synthetase inhibitors; a squalene epoxidase inhibitor; a squalene cyclase inhibitor; a combined squalene epoxidase/squalene cyclase inhibitor, or a CETP inhibitor; fibrates; niacin, an ion-exchange resin, an antioxidant; bile acid sequestrants (such as questran); ACAT inhibitors; MTP/APO β secretion inhibitors; lipooxygenase inhibitors; cholesterol absorption inhibitors; cholesteryl ester transfer protein inhibitors; an agent such as mipomersen; and or atherosclerotic agents including PCSK9 modulators.

In another embodiment, a compound of Formula I may be co-administered with agents for the treatment of NASH and/or NAFLD, such as Obeticholic Acid (OCA, Intercept), GFT505 (elafibranor), caspase inhibitors (e.g. emricasan), glutathione transferase inducers (e.g. oltipraz), adenosylmethionine decarboxylase inhibitors (e.g. SAMe), fatty-acid/bile-acid conjugate (FABAC), such as aramchol, FGF21 analogs including long-acting pegylated FGF-21 (BMS-986036), CCR2/CCR5 dual receptor antagonist (e.g. cenicriviroc or TAK652), Galectin-3 inhibitor (e.g. GR-MD-02), apoptosis stimulating kinase-1 inhibitor (e.g. GS-4997), 5-lipoxygenase inhibitor (e.g. tipelukast), siRNA against HSP 47 (e.g. ND-L02-s0201), Orlistat, TZDs and other insulin sensitizing agents, Metformin, Omega-3-acid ethyl esters (e.g. Lovaza), Fibrates, HMG CoA-reductase Inhibitors, Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buprobrion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-inflammatory agents (steroidal and non-steroidal), anti-osteoporosis agents, hormone replacement therapies, oral contraceptives, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the invention include warfarin, synthetic pentasaccharide, and heparins (e.g., unfractioned and low molecular weight heparins such as enoxaparin and dalteparin).

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., cilostazol, dipyridamole), and pharmaceutically acceptable salts or prodrugs thereof.

The term anti-platelet agents (or platelet inhibitory agents), as used herein, is also intended to include ADP receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, argatroban, boroarginine derivatives, boropeptides, dabigatran, heparins (unfractionated and separately low molecular weight), hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Non-limiting examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrasentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopeptidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In another embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be co-administered with a phthalimidine-type diuretic. In still another embodiment, the phthalimidine-type diuretic is chlorthalidone.

Examples of suitable mineralocorticoid receptor antagonists include spironolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

In another embodiment, the invention provides combination therapies wherein the compounds of this invention may also be used in conjunction with other pharmaceutical agents for the treatment of the diseases, conditions and/or disorders described herein. Therefore, methods of treatment that include administering compounds of the invention in combination with other pharmaceutical agents are also provided.

Administration and Dosing

Typically, a compound of the invention is administered in an amount effective to treat a disease as described herein. The compounds of the invention are administered by any suitable route in the form of a pharmaceutical composition adapted to such a route, and in a dose effective for the treatment intended. Therapeutically effective doses of the compounds required to treat the progress of the disease are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

Pharmaceutical Compositions

For the treatment of the diseases referred to herein, the compounds of the invention may be administered as compound per se. Alternatively, pharmaceutically acceptable salts are suitable for medical applications because they may have greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Preparation

In the preparation of the compounds of Formula I, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I compounds.

The Reaction Schemes described below are intended to provide a general description of the methodology employed in the preparation of the compounds of the present invention. Some of the compounds of the present invention contain a single chiral center with stereochemical designation (R). It will be apparent to one skilled in the art that all of the synthetic transformations can be conducted in a similar manner whether the materials are enantioenriched or racemic. Moreover the resolution to the desired optically active material may take place at any desired point in the sequence using well known methods such as described herein and in the chemistry literature.

In the Reaction Schemes that follow, the variables X, Y, Z, $R^1$, $R^2$, $R^3$, $R^4$, $R^C$, $R^N$, $R^S$, L, m, and n are as described herein for compounds of Formula (I) unless otherwise noted. For the Schemes provided below, some leaving groups are identified as $LG^3$ or $LG^2$, each of which may independently be halogen, $SO_2$-alkyl, $SO_2$-aryl, S-alkyl, S-aryl, S(O)-alkyl, S(O)-aryl, or an oxygen bonded to a phosphorus containing moiety. Each $LG^3$ can independently be a leaving group such as any alkyl or aryl sulfonate (e.g., mesylate, tosylate, or triflate), or a halogen or any other group that can be displaced by an amine. Each "alkyl" is independent of the other and generally contains 1 to 6 carbon atoms. Aryl is generally phenyl. When the protecting group is identified as $PG^1$, it can be an alkyl amine protecting group such as benzyl, benzhydryl, or the like; a carbamate protecting group such as Boc, Cbz, or the like; or an amide protecting group such trifluoroacetamide.

The pyrimidinyl and cyanopyridinyl rings may be prepared as discussed in Scheme 1. Intermediates of formula 6 can be purchased or be generally synthesized by condensation reactions as shown in Scheme 1. Esters 1 (where $R^3$ can be F, Cl, Br, alkyl, and the like) can be deprotonated by the action of a base such as potassium t-butoxide, lithium diisoproprylamide, sodium hydride, and the like and reacted with esters 2 to provide beta-keto esters 3. Alternatively, ketones of general formula 7 can be treated with similar bases and reacted with chloroformates 8 to provide similar beta-keto esters 3.

Esters 3 can then be condensed with reagents like urea to form pyrimidines 5 with or without heating or alternatively with acid or base catalysis. Activation of the hydroxyl to a leaving group can be effected by reagents such as phosphorus oxyhalide, phosphorus pentahalide, alkyl or aryl-thiols and salts thereof (followed with oxidation or not), BOP, PyBOP, or other similar activating reagents to provide compounds of general formula 6.

Scheme 1
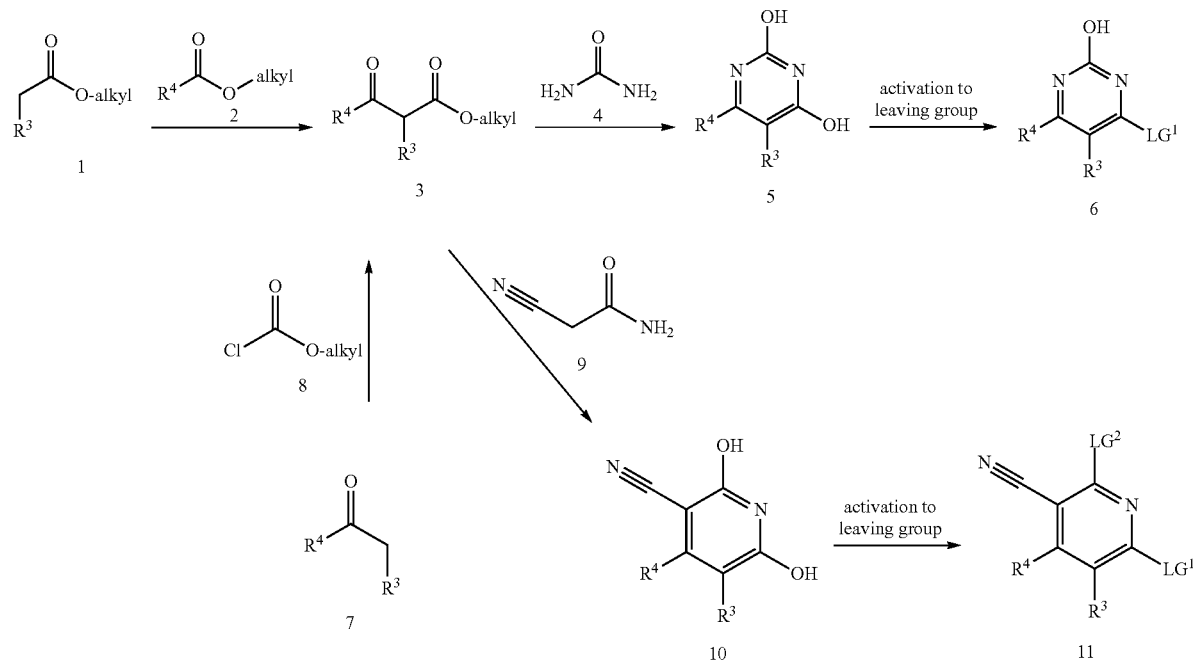
Compounds of general formula 11 can be purchased or synthesized starting from beta-keto esters 3 that can be reacted with cyanoacetamide 9 to give compounds of general formula 10. These can be converted to compounds of general formula 11 in a manner analogous to the transformation of 5 to 6.
Scheme 2
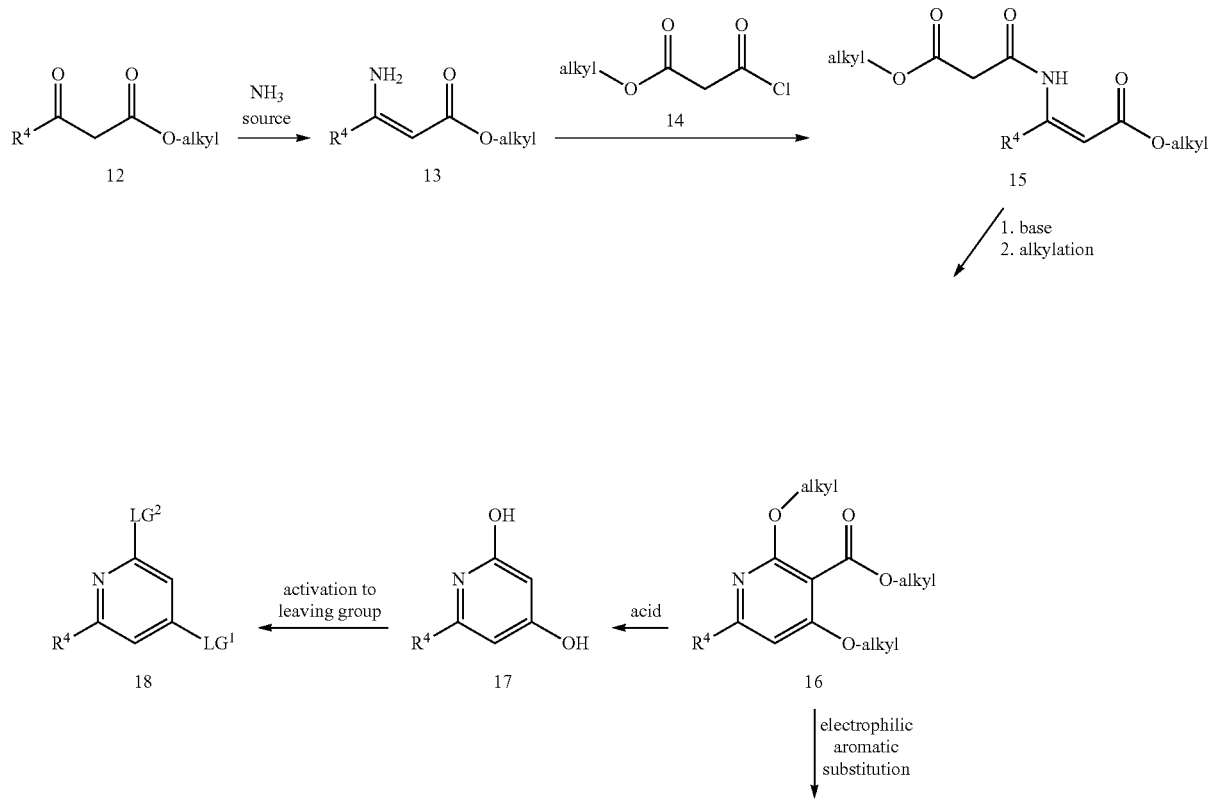

-continued

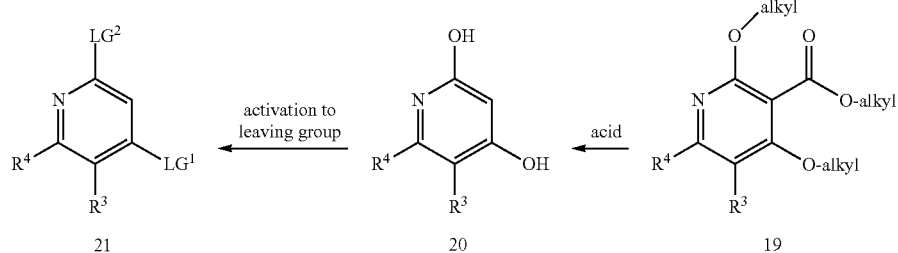

Intermediates 18 can be synthesized as shown in Scheme 2. Starting from beta keto esters 12, treatment with an ammonia source such as ammonium acetate, ammonium chloride, ammonium hydroxide, ammonia in solvent solution and the like under a variety of conditions including with or without heating or alternatively with acid or base catalysis to provide compounds of general formula 13. Treatment with acid chlorides 14 can then lead to compounds of general formula 15. Treatment with base can cyclize to the pyridine and alkylation of the resultant hydroxyl group can lead to pyridines 16. Treatment with acid such as hydrogen fluoride, chloride, bromide, iodide, or a variety of Lewis Acids with or without heating can lead to compounds of general formula 17. Activation of the hydroxyl functional groups to leaving groups to form intermediates of general formula 18 can take place in an analogous fashion to the conditions described for the transformation of 5 to 6 in Scheme 1. Alternatively, the pyridine can be prepared with substitution (where $R^3$ is F, Cl, Br, and alkyls that can be introduced via electrophilic aromatic substitution via methods such as Friedel-Crafts alkylations) by reacting compounds of formula 16 with one of a variety of electrophilic aromatic substitution conditions such as chlorine gas, bromine, selectFluor™, N-fluorobenzenesulfonimide, N-halosuccinimides, or any other known sources of electrophilic halide, or alkyl halides in the presence of aluminum catalysts, to provide compounds of general formula 19. This can then be converted into intermediates of general formula 21 by analogous methods as described for the conversion of 16 to 18.

Scheme 3A

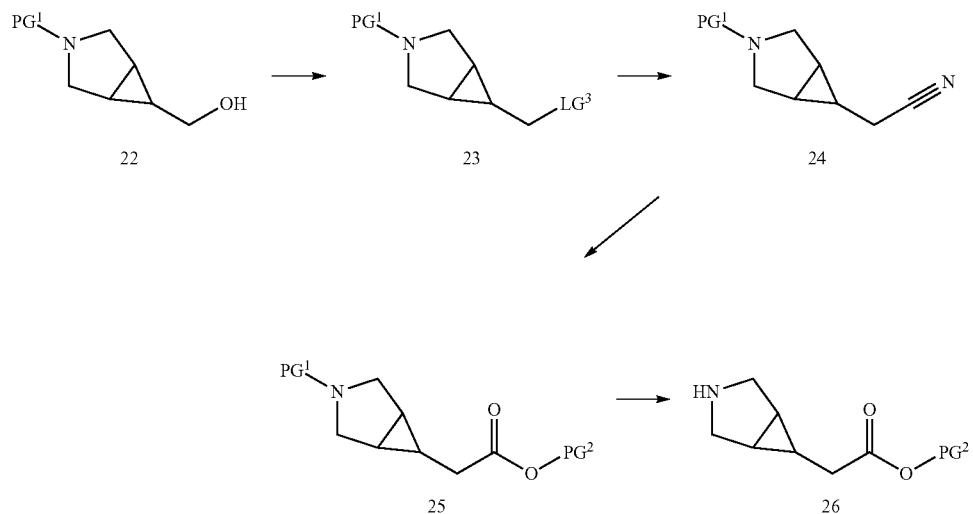

Amines of general formula 26 can be purchased or generally synthesized as shown in Schemes 3A to 3D. Starting from protected [3.1.0]azabicyclohexanes 22 (purchased or synthesized in manners similar to Berliner, M. A.; et al. *Org. Process Res. Dev.* 2011, 15, 1052-1062), the hydroxyl moiety can be converted into $LG^3$ using standard procedures and displaced with known carbon-containing homologation reagents such as sodium or potassium cyanides to provide nitriles 24. The nitrile moiety could then be hydrolyzed to esters 25 (or a carboxylic acid) under various standard conditions for acid or basic catalysis, where $PG^2$ is alkyl (e.g., $C_{1-6}$alkyl) or benzyl. Removal of $PG^1$ could be effected in many manners described in literature to provide amino esters 26.

Scheme 3B

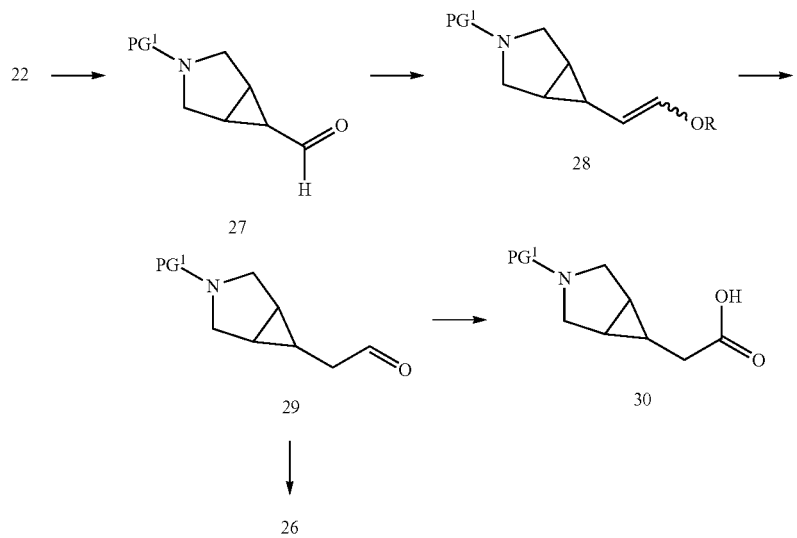

Alternatively, as in Scheme 3B, the hydroxyl moiety of 22 could be oxidized to aldehyde 27 and homologated using a Wittig reaction and hydrolysis to provide homologated aldehydes 29. Further oxidation using a variety of oxidants such as sodium chlorite, bleach, potassium permanganate, or others would then provide carboxylic acids 30 or esters 26.

Scheme 3C

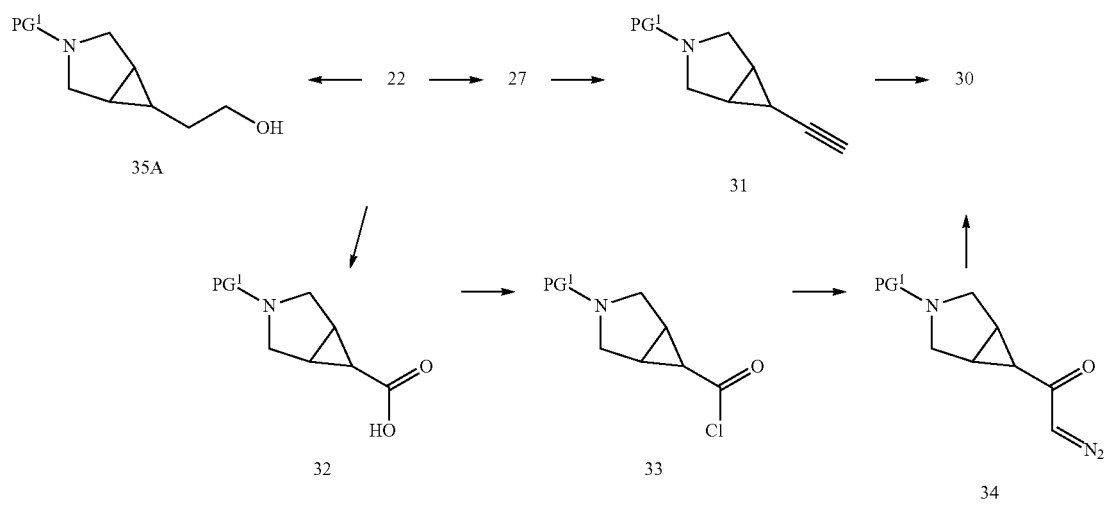

Alternatively, as in Scheme 3C, the aldehydes 27 could be converted into alkynes 31 using a variety of conditions such as Gilbert-Seyferth, Ohira-Bestman reagent, $CBr_4$ with $PPh_3$, or others. The alkyne could then be converted into carboxylic acids 30 using Brönsted or Lewis acids, or with metal catalysis such as with gold catalysis. Alternatively, the hydroxyl group could be oxidized to acids 32 and treated to Arndt-Eistert homologation (32 to 33 to 34 to 30) conditions to provide homologated acids 30. Alternatively compounds of general formula for intermediate 35A can be synthesized by functionalizing alcohols 22 under a variety of conditions described in literature (see, e.g., WO2010116328).

Scheme 3D

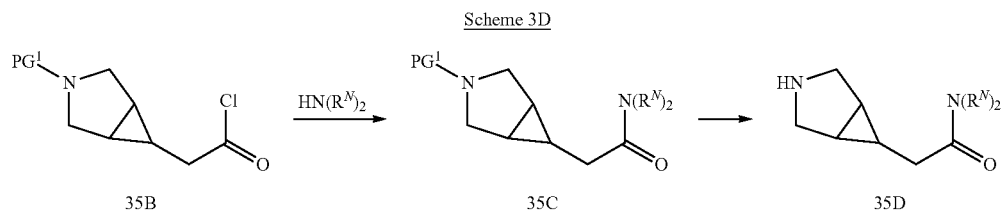

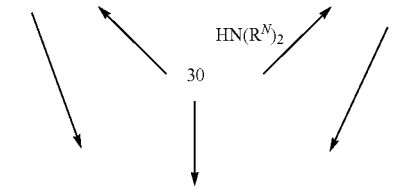

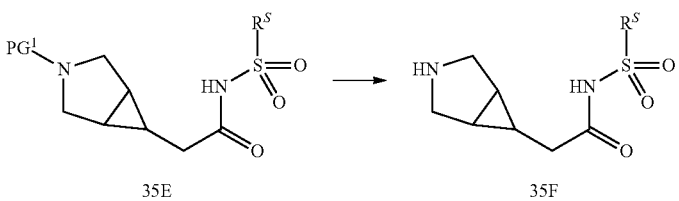

Amines of formula 35D, 35F, 35H, 35K, 35N can be synthesized as described in literature or synthesized as described in Schemes 3D to 3F. Starting from 30, treatment with a reagent that displaces hydroxyl with chloride (such as phosphorus oxychloride, oxalyl chloride, phosphorus pentachloride, thionyl chloride, sulfuryl chloride, and others in the presence of or in the absence of DMF) can lead to acid chlorides 35B. Subsequent treatment with an amine, $HN(R^N)_2$, in the presence of any base, such as DIPEA, TEA, DBU, $K_2CO_3$, $NaHCO_3$, or any others can lead to amides 35C. Alternatively, 30 can be directly coupled with an amine using any amide coupling reagent to activate the carboxylic acid (such as EDC, HATU, T3P, COMU, DCC, and many others described in literature) to provide 35C. Acid chloride 35B can be treated with a sulfonamide, $H_2NS(O)_2R^S$ to provide acyl sulfonamides 35E. Alternatively, 30 can be converted to 35E using a sulfonamide, $H_2NS(O)_2R^S$, and conditions analogous to those described for the conversion of 30 to 35C.

Scheme 3E

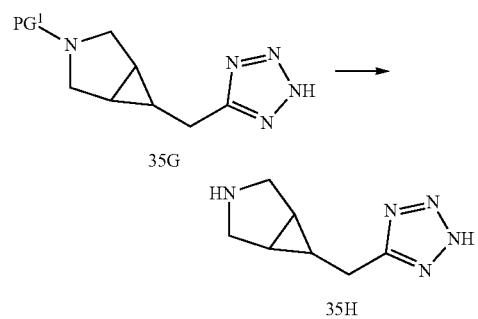

Intermediate 24 can be converted into tetrazole 35G with the addition of an azide such as sodium-, potassium-azide, trimethylsilylazide, tributyltin azide, or others, in the presence of heat or with the addition of a catalyst to accelerate the reaction. Tetrazole 35H is then obtained using standard procedures to remove $PG^1$.

Scheme 3F

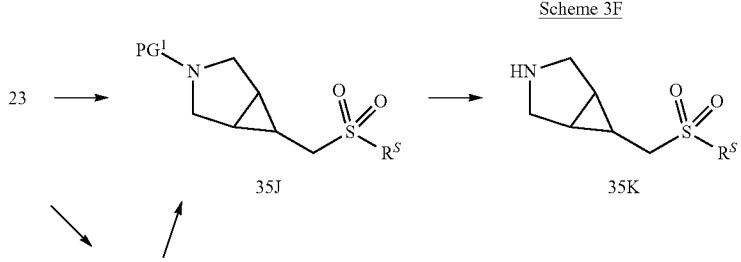

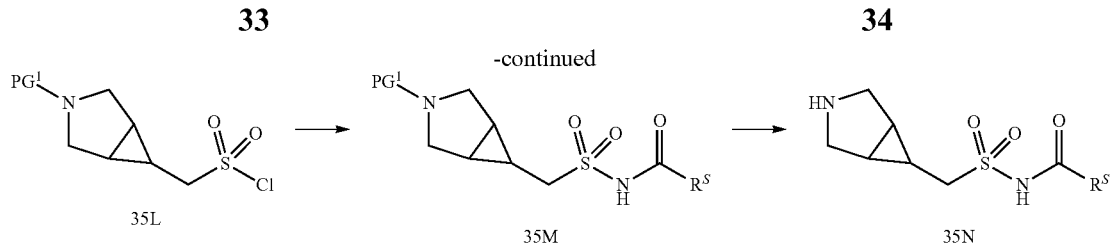

Intermediate 23 can be converted into sulfone 35J with a variety of methods such as displacement of the leaving group with a sulfinic acid or sodium, potassium, or other salt of sulfinic acid, $HOS(O)R^S$ under neutral or basic conditions. Alternatively, Intermediate 23 can be converted into 35J in a process consisting of displacement of the leaving group on Intermediate 23 with a thiol or a sodium, potassium, or other salt of thiol to provide a thioether, which can then be oxidized to a sulfone using an oxidant such as meta-chloroperbenzoic acid, hydrogen peroxide, potassium permanganate, or many other oxidants. Alternatively, Intermediate 23 can be converted into sulfonyl chloride 35L by treatment with thiourea followed by bleach; or with metal-halogen exchange with a reagent such as magnesium, or butyllithium, followed by treatment with sulfur dioxide or a sulfur dioxide source such DABCO-SO$_2$, and subsequent chlorination using NCS, thionyl chloride, phosphorus oxychloride, or other chlorinating reagents; or other methods known in literature. Intermediate 35L can be converted into 35J by treatment with an alkylating reagent such as alkyllithium, alkylmagnesium halide, trialkylaluminum, or any other nucleophilic sources of alkyl groups. Intermediate 35L can be converted into acyl sulfonamide 35M by treatment with an amide, $H_2NC(O)R^S$ in the presence of base such as sodium hydride, lithiumdiisopropylamide, potassium carbonate, DBU, or other bases. Removal of the protecting groups of 35C, 35E, 35G, 35J, and 35M can be effected with acidic, basic, hydrogenolysis, or other conditions known in literature to remove a given protecting group to provide 35D, 35F, 35H, 35K, and 35N, respectively.

Scheme 4A

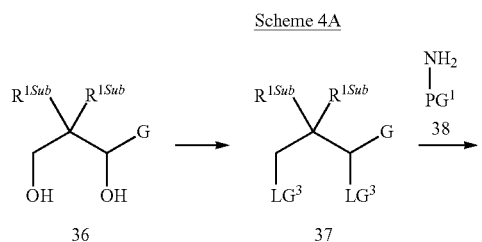

Azetidines 40 (where G can be H or any $C_{1-3}$alkyl) can be purchased, synthesized as described in literature (such as in *J. Med. Chem.* 1994, 37, 4195), or synthesized as described in Schemes 4A to 4C. Intermediate diols 36 can be converted into Intermediates 37 through activation with mesyl chloride or anhydride, triflic anhydride, and other sulfonate-forming reagents or converted into a halide leaving group with thionyl chloride, carbon tetrabromide with triphenylphosphine, iodine with triphenyl phosphine or imidazole, or a variety of other reagents. Treatment of 37 with amine 38 can lead to azetidines 39. Standard deprotection methods afford intermediates of general formula 40 that ultimately become $R^1$ of compounds of Formula (I), so $R^{1sub}$ is H when $R^1$ is not substituted or $R^{1sub}$ is —$C_{1-3}$alkyl and —OH as defined in any embodiment of compounds of Formula (I) for substituents off of $R^1$.

Scheme 4B

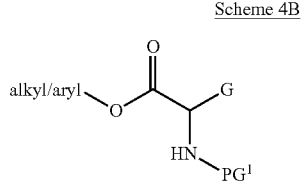

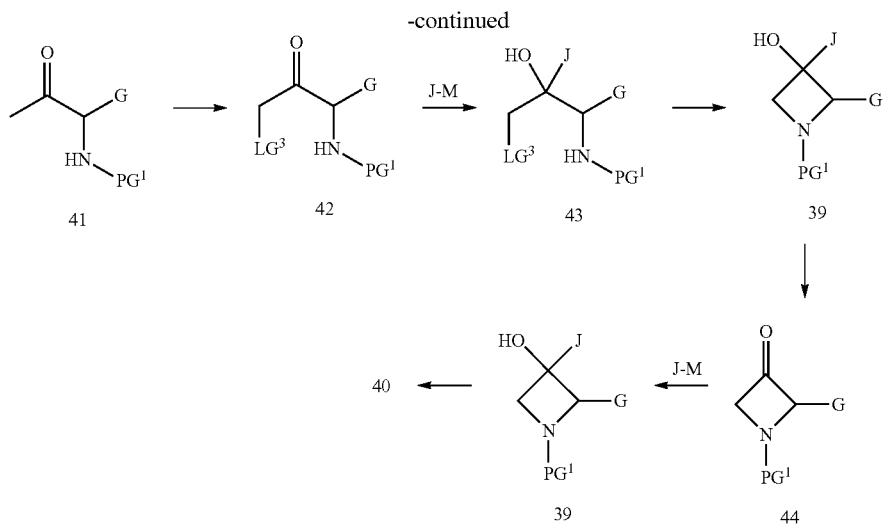

Alternatively, as in Scheme 4B, when J is hydrogen, oxidation can take place to provide ketones 44 (where G can be H or any $C_{1-3}$alkyl). Treatment with any known metal hydride (J-M, where J is hydrogen and M is a metal counterion such as lithium, magnesium, zinc, aluminum, boron, or others) source can lead to azetidinyl Intermediates 40 for $R^1$, influencing the desired stereochemical outcome through reagent selection. Alternatively, ketones 44 can be treated with metal alkylating agents (J-M, where J is any $C_{1-3}$alkyl and M is a metal counterion such as lithium, magnesium, zinc, aluminum, boron, or others) such as alkylmagnesium halides, alkyllithiums, or many other sources of nucleophilic alkyl groups to provide compounds of general formula 39 where J is alkyl. These can be taken forward to azetidines 40 as described previously. Alternatively, ketones 41 can be activated with a leaving group ($LG^3$) by treatment with base and electrophilic halogen source to provide ketones 42. Derivitization can then be performed in a manner analogous to the transformation of 44 to 39 to provide compounds 43. These can be exposed to basic conditions to form azetidines 39 where J is alkyl or hydrogen, which can be taken forward to Intermediates 40 as described previously. Alternatively, esters 45 can be converted into ketones 42 through a homologation reaction with the incorporation of a leaving group with reagents such as chloroacetic acid or dihalomethane both in the presence of strong base or with a sulfonium ylide, and many other reagents as described in literature. Intermediate 42 can then be taken forward to 40 as described previously.

Scheme 4C

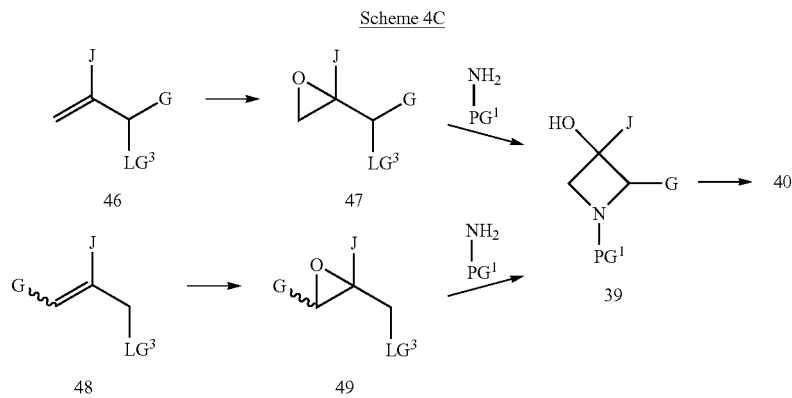

Alternatively, alkenes 46 or 48 (where J can be any alkyl or hydrogen; G can be H or any $C_{1-3}$alkyl); can be treated with a variety of oxidants such as m-CPBA (meta-chloroperbenzoic acid), hydrogen peroxide, t-butyl hydroperoxide, Sharpless epoxidation conditions, Shi epoxidation conditions, or many other conditions known in literature to provide epoxides 47 or 49, respectively. Epoxides 47 or 49 can be treated with an amine in a manner analogous to the transformation of 37 to 39 to provide azetidines 39, which can be taken forward to Intermediates 40.

Scheme 5

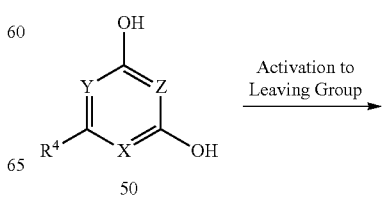

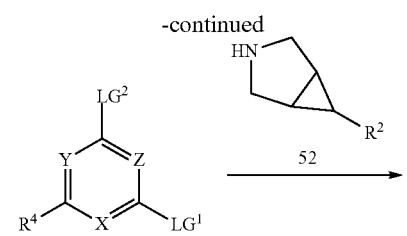

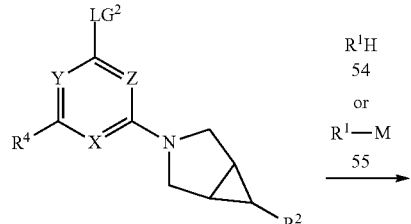

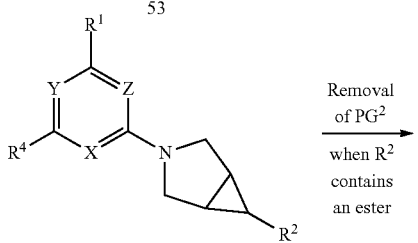

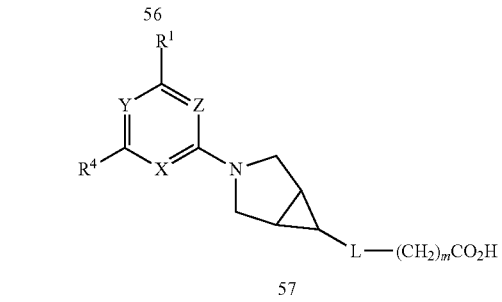

Intermediates of Formula 56 and 57 can generally be synthesized as shown in Scheme 5. Starting from bis-hydroxyheteroaryls of general formula 50 (purchased, known in literature, or described in previous schemes), conversion to intermediates of general formula 51 can occur in an analogous fashion to the process described for the transformation of Intermediate 5 to 6 in Scheme 1. Amines of general formula 52 (purchased, found in literature, or described in previous schemes, such as 30 or 25, which must first be deprotected under acidic, basic, hydrogenolysis, or other conditions as described in literature for a given protecting group) can be coupled with 51 under basic or acidic conditions via an $S_NAr$ reaction in the presence of bases such as sodium-, potassium-, or cesium carbonate, -bicarbonate, hydroxide, acetate, or an organic amine base such as triethylamine, diisopropylethylamine, DBU, and the like or under palladium catalysis with a variety of palladium sources, ligands, and bases to provide Intermediates 53. These can then be subsequently coupled with amines of general formula 54 (purchased, found in literature, or described in previous schemes such as 40) in an analogous manner to the previous step, but often with higher temperatures to produce Intermediates 56. Alternatively, treatment of compounds 53 with alkyl-metal or metalloid complexes 55 such as alkyl zinc, alkylboronic acid, -boronate, -trifluoroborate salts and the like under palladium catalysis can provide Intermediates 56. When $R^2$ contains an ester (see Scheme 3A), a carboxylic acid can be revealed using a variety of conditions as found in literature to provide Intermediates 57.

Scheme 6A

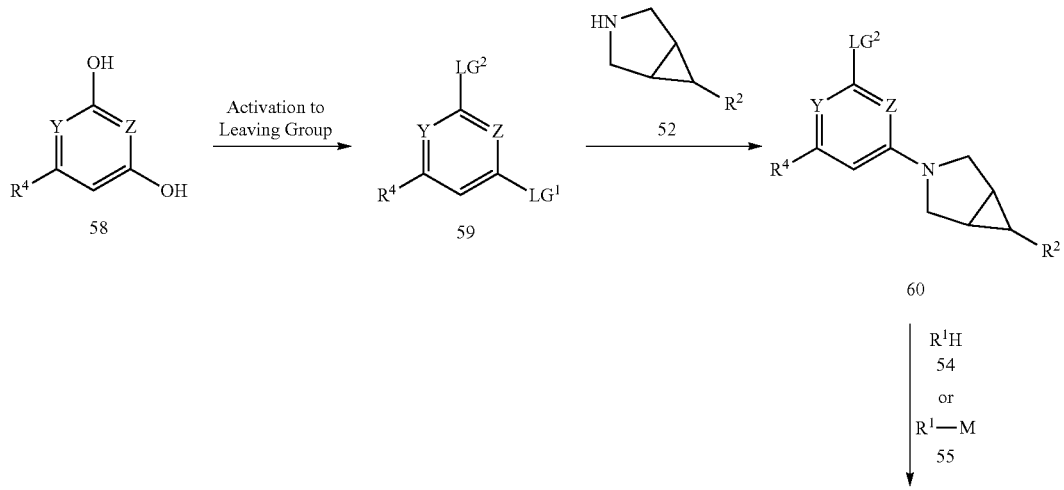

-continued

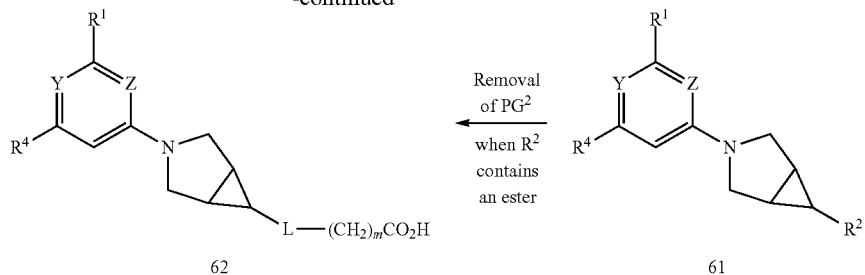

Alternatively, Intermediates 60, 61, and 62 (Scheme 6A) can be synthesized in a manner analogous to the methods described for Intermediates 53, 56, and 57, respectively, as shown in Scheme 5.

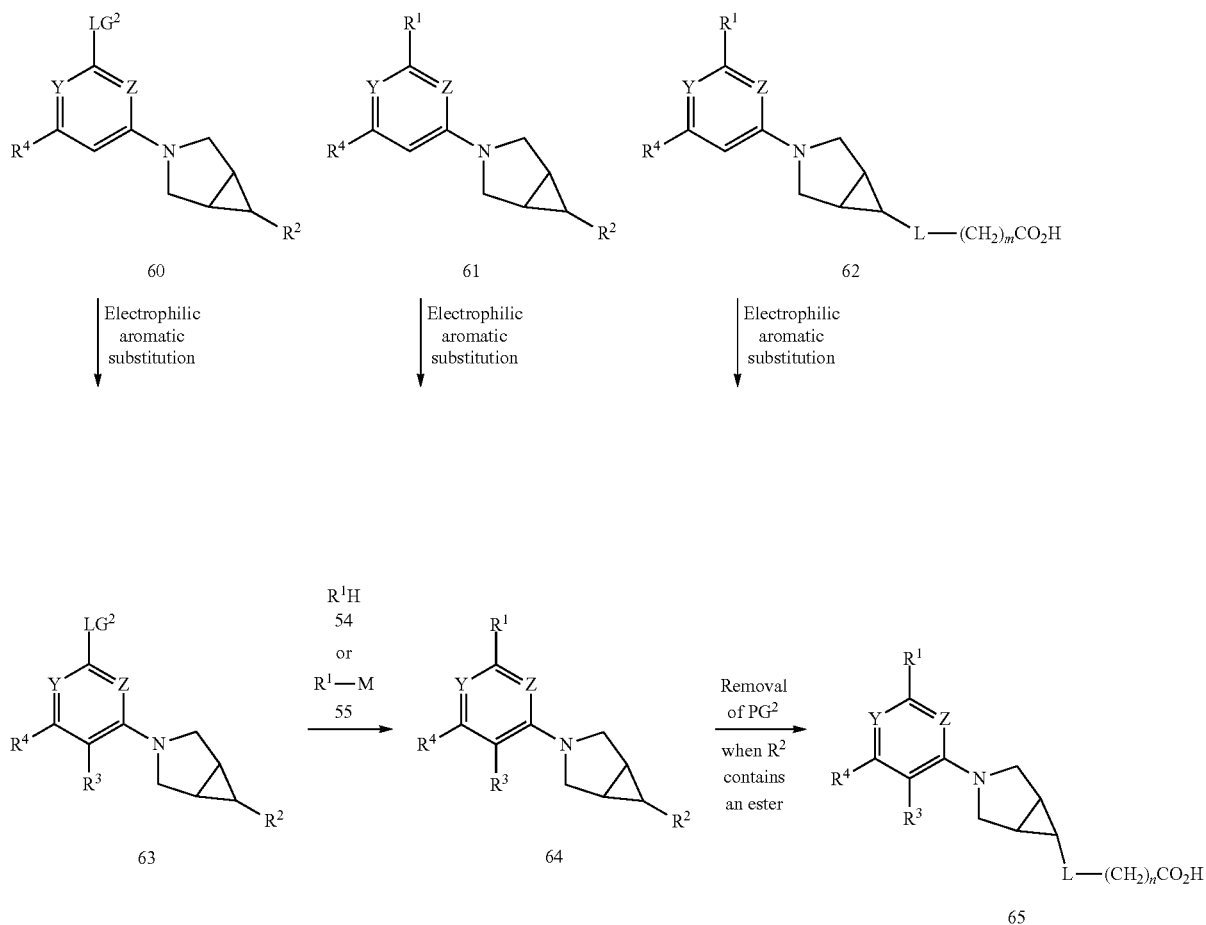

Intermediates 60, 61, and 62 can be subjected to electrophilic aromatic substitution reactions in a manner analogous to the methods described for the transformation of Intermediate 16 to 19 in Scheme 2 to produce Intermediates 63, 64, and 65, respectively, where $R^3$=F, Cl, Br, I or alkyls that can be introduced via electrophilic aromatic substitution via methods such as Friedel-Crafts alkylations. Intermediates 63 and 64 can then be taken forward to compounds of formula 65 through methods analogous to those already described.

Scheme 6C

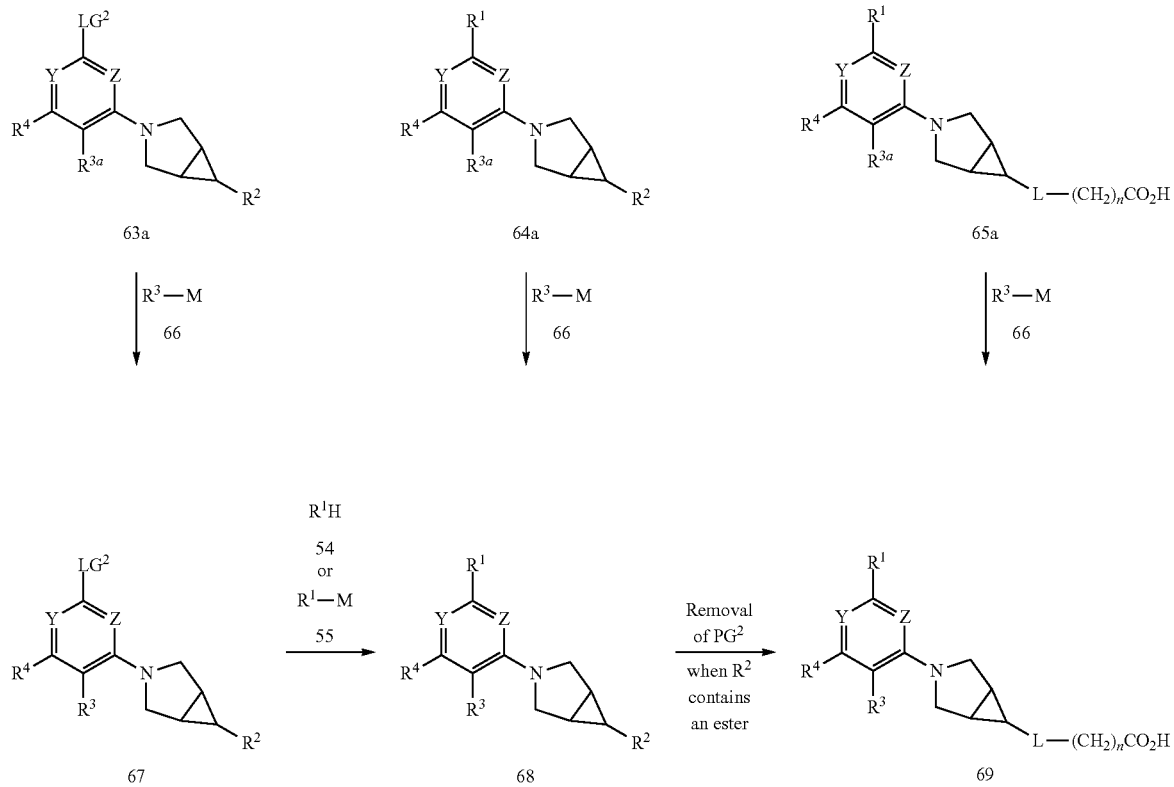

Alternatively, as shown in Scheme 6C, compounds 63a, 64a, and 65a (where $R^{3a}$=halogen) can be converted into compounds of general formula 67, 68, and 69, respectively, (where $R^3$=Me, Et, iPr, cPr, and OMe) by treatment with $R^3M$ (reagent 66 where M can be a metal or metalloid such as sodium, potassium, zinc, tin, boron, aluminum, magnesium, or others) and palladium or copper catalysis in a manner analogous to the described coupling of 53 with 55 to from compounds 56 (Scheme 5).

Exemplified Intermediates 2,4-dichloro-6-(difluoromethyl)pyrimidine

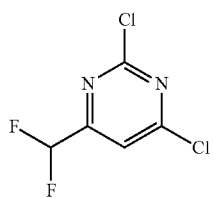 [SMILES: FC(F)c1cc(Cl)nc(Cl)n1]

A solution of ethyl difluoroacetate (250 g, 2.01 mol) and EtOAc (1070 g, 12.10 mol) was heated to 70° C. and treated with a solution of sodium ethoxide (151 g, 2.22 mol) in anhydrous ethanol (2500 mL) over 2 h. The resulting yellow mixture was stirred at 70° C. for 14 h. The cooled reaction mixture was acidified to pH=2-3 with a solution of 4M HCl in EtOAc, resulting in precipitation of solids. The mixture was filtered through a pad of Celite®, and the filtrate cake was washed with EtOAc (4×30 mL). The filtrate was concentrated to give crude ethyl 4,4-difluoro-3-oxobutanoate (200 g, 59.8%) as yellow oil, which was used in the next step without further purification.

To a solution of ethyl 4,4-difluoro-3-oxobutanoate (100 g, 602 mmol) in anhydrous toluene (1000 mL) was added urea (43.4 g, 722 mmol) and 2M sodium ethoxide in ethanol (81.7 g, 1.20 mol) dropwise. The resulting yellow solution was stirred at rt for 30 min, and then stirred at 120° C. for 16 h. The yellow suspension was then stirred at 130° C. for an additional 16 h. The yellow suspension was cooled to rt and concentrated to give 6-(difluoromethyl)pyrimidine-2,4-diol as a yellow solid (100 g, quant.), which was used in the next step directly without further purification.

In two separate batches, a brown suspension of 6-(difluoromethyl)pyrimidine-2,4-diol (97.6 g, 602 mmol) and N,N-dimethylaniline (67.8 g, 560 mmol) in acetonitrile (1000 mL) was cooled to 0° C. and phosphorus oxychloride (231 mL, 2.48 mol) was added dropwise. After the addition was complete, the resulting mixture was heated to 95° C. for 16 h. The reaction was then cooled to 25° C., quenched with ice water (1000 mL), and extracted with methyl tert-butyl ether (8×500 mL). The combined organic layers were washed with brine (200 mL), dried over anhydrous $Na_2SO_4$, filtered and concentrated to give a brown oil (100 g). The two batches were combined and purified using column chromatography (100:0 to 98:2 petroleum ether/EtOAc) to give 2,4-dichloro-6-(difluoromethyl)pyrimidine (92.0 g) as a light yellow oil.

$^1$H NMR (400 MHz, $CD_3OD$) δ: 7.87 (s, 1H), 6.72 (t, 1H).

2,4-dichloro-6-(difluoromethyl)-5-methylpyrimidine

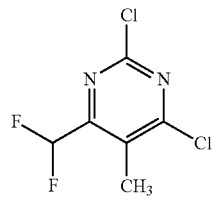

A solution of ethyl propionate (200 g, 1.96 mol) in THF (1250 mL) was treated with sodium hydride (60% in mineral oil, 78.3 g, 1.96 mol) in portions. The resulting slurry was then treated with ethyl difluoroacetate (486 g, 3.92 mol) dropwise over 2 h. The slurry was heated at 50° C. for 19 h. The cooled reaction mixture was then treated with 10% sulfuric acid (600 mL) and extracted with EtOAc (4×500 mL). The combined organic layers were washed with brine (1000 mL), dried over $Na_2SO_4$, filtered and evaporated. The crude product was purified using column chromatography eluting with petroleum ether/EtOAc (100:0 to 5:1) to give ethyl 4,4-difluoro-2-methyl-3-oxobutanoate (260 g, 74%) as a red oil, which was used directly in the next step.

In two separate batches, to a solution of 4,4-difluoro-2-methyl-3-oxobutanoate (130 g, 722 mmol) in anhydrous toluene (1.44 L) was added urea (52.0 g, 866 mmol) and 2M sodium ethoxide in ethanol (98.2 g, 1.44 mol) dropwise. The resulting yellow solution was stirred at rt for 30 min, and then stirred at 130° C. for 16 h. The cooled reaction mixtures were combined and concentrated to give 6-(difluoromethyl)-5-methylpyrimidine-2,4-diol (254 g) as a light yellow solid which was used directly in the next step.

A mixture of 6-(difluoromethyl)-5-methylpyrimidine-2,4-diol (84.7 g, 481 mmol) and phosphorus pentachloride (401 g, 1.92 mol) was stirred at 140° C. for 16 h. The cooled reaction mixture was poured into ice water (5000 mL) and extracted with methyl tert-butyl ether (8×1000 mL). The organic phase was washed with brine (3000 mL) dried over $Na_2SO_4$, filtered and concentrated to give a dark brown oil (300 g, crude). The crude product was divided into three batches and purified using column chromatography eluting with petroleum ether/EtOAc (100:0 to 98:2) to give 2,4-dichloro-6-(difluoromethyl)-5-methylpyrimidine as a red oil (92 g, 30%).

$^1$H NMR (400 MHz, $CD_3OD$) δ: 6.83 (t, 1H), 2.49 (s, 3H).

2,4-dichloro-5-methyl-6-(trifluoromethyl)pyrimidine

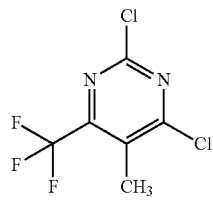

To a solution of ethyl propionate (35.0 g, 340 mmol) in THF (350 mL) at 25° C. was added sodium hydride (60% in mineral oil, 13.7 g, 343 mmol). The grey slurry was heated to 50° C. and ethyl trifluoroacetate (97.4 g, 685 mmol) was added dropwise to the mixture over 15 min. The reaction was stirred at 50° C. for 16 h. The cooled reaction mixture was slowly added to 10% sulfuric acid at 0° C. The resulting yellow mixture was extracted with EtOAc (3×500 mL) and the combined organic layers were dried over $Na_2SO_4$, filtered and concentrated to give ethyl 4,4,4-trifluoro-2-methyl-3-oxobutanoate (60 g) which was used directly in the next step.

To a solution of ethyl 4,4,4-trifluoro-2-methyl-3-oxobutanoate (60.0 g, 303 mmol) in anhydrous toluene (500 mL) was added urea (21.8 g, 363 mmol) and freshly prepared 2M sodium ethoxide in ethanol (41.2 g, 606 mmol) in portions. The resulting yellow solution was stirred at rt for 15 min, and then heated to 130° C. for 48 h. The reaction mixture was concentrated and solvent was removed to provide crude 5-methyl-6-(trifluoromethyl)pyrimidine-2,4-diol (60 g) as a gum, which was used in the next step without further purification.

5-Methyl-6-(trifluoromethyl)pyrimidine-2,4-diol (120 g, 480 mmol) was added into phosphorus oxychloride (371.0 g, 2.420 mmol) at 0° C. and treated with N,N-dimethylaniline (54.6 g, 451 mmol) dropwise. The resulting mixture was heated to 100° C. for 16 h. The dark reaction mixture was cooled to rt and poured into ice water. The water layer was extracted with methyl tert-butyl ether (3×1000 mL) and combined organic layers were dried over $Na_2SO_4$ and concentrated to give a dark yellow oil (80 g). The crude product was dissolved in n-hexane and some insoluble material formed which was removed by filtration. The filtrate was concentrated under reduced pressure to provide 2,4-dichloro-5-methyl-6-(trifluoromethyl)pyrimidine (40 g, 36%) as a yellow oil with residual n-hexane present.

$^1$H NMR (400 MHz, $CD_3OD$) δ: 2.53 (s, 3H).

2,4-dichloro-6-(1,1-difluoroethyl)pyrimidine

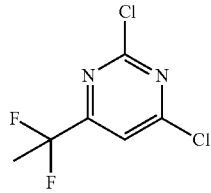

Step 1: 6-(1,1-difluoroethyl)pyrimidine-2,4-diol

A solution of lithium hexamethyldisilazide (217 ml, 1M solution in THF, 217 mmol) in dry THF (400 mL) was cooled under an atmosphere of argon to −78° C. and treated with EtOAc (19.1 g, 217 mmol) dropwise. The reaction mixture was stirred at −78° C. for 1 h, then treated with ethyl 2,2-difluoropropionate (15.0 g, 110 mmol) dropwise. Stirring was continued for 4 h at -78° C. A saturated solution of ammonium chloride (150 ml) was added dropwise. The mixture was warmed to rt, acidified with 1M HCl (150 ml) and left standing for 2 h. The phases were separated, the aqueous phase was extracted with EtOAc, and the combined organic phases were washed with 1M HCl, brine, dried over $Na_2SO_4$ and concentrated. The crude product was purified using column chromatography eluting with petroleum ether/EtOAc (100:0 to 7:3) to give ethyl 4,4-difluoro-3-oxopentanoate (27 g) as a yellow oil which was used directly in the next step.

To a solution of ethyl 4,4-difluoro-3-oxopentanoate (20.0 g, 111 mmol) and urea (8.00 mg, 133 mmol) in anhydrous toluene (400 mL) and ethanol (30 mL) was added solid sodium ethoxide (30200 mg, 222 mmol) at rt. Then the mixture was heated to 125° C. under a reflux condenser fitted with a Dean-Stark trap. The reaction mixture was cooled to rt and the solvent was removed under reduced pressure. The residue was acidified to pH=4 with 4N HCl in EtOAc and extracted with EtOAc (3×100 mL). The combined organic layer was washed with brine, dried over with $Na_2SO_4$, filtered and the filtrate was concentrated to give the crude product (20.0 g) as yellow oil. The crude product was purified using EtOH:petroleum ether (1:1) to allow collection of the title compound (11.6 g, 59%) as a solid.

$^1$H NMR (400 MHz, $CDCl_3$) δ: 5.71 (s, 1H), 1.93 (t, 3H).

Step 2

To a solution of 6-(1,1-difluoroethyl)pyrimidine-2,4-diol (9.60 g, 54.5 mmol) in acetonitrile (120 mL) was added phosphorus oxychloride (41.8 g, 273 mmol) followed by N,N-diisopropylamine (704 mg, 5.45 mmol). The mixture was stirred at 80° C. for 16 h. The reaction mixture was cooled to rt and poured into ice-water (60 mL). The mixture was basified to pH=7 to 8 with saturated aqueous sodium carbonate and extracted with EtOAc (3×30 mL). The organic phase was dried over $Na_2SO_4$, filtered and concentrated to give a brown oil. The crude product was purified by using column chromatography eluting with DCM/petroleum ether to provide 2,4-dichloro-6-(1,1-difluoroethyl)pyrimidine (6.5 g, 56%) as a clear oil.

$^1$H NMR (400 MHz, $CD_3OD$) δ: 7.85 (s, 1H), 1.97 (t, 3H).

2,4-dichloro-6-(1,1-difluoroethyl)-5-methylpyrimidine

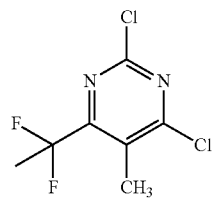

Step 1: ethyl 4,4-difluoro-2-methyl-3-oxopentanoate

To a solution of ethyl propionate (15.0 g, 147 mmol) in THF (70 mL) was added sodium hydride (60% in mineral oil, 5.87 g, 147 mmol) in portions. The resulting grey slurry was then treated with ethyl 2,2-difluoropropionate (24.3 g, 176 mmol) dropwise over 15 min. The slurry was heated to 50° C. for 4 h, then stirred at 16° C. for 60 h. The mixture was slowly poured into 10% sulfuric acid (60 mL) and extracted with EtOAc (2×50 mL). The organic phase was dried over $Na_2SO_4$, filtered and concentrated. The crude product was purified with column chromatography eluting with EtOAc:petroleum ether (1:10) to give the title compound (18 g) as a brown oil.

$^1$H NMR (400 MHz, $CD_3OD$) δ: 3.76 (q, 2H), 3.52 (q, 1H), 1.32 (t, 3H), 0.98 (d, 3H), 0.83 (t, 3H).

Step 2

To a solution of ethyl 4,4-difluoro-2-methyl-3-oxopentanoate (18 g, 93 mmol) and urea (6.68 g, 111 mmol) in toluene (270 mL) was added a solution of sodium ethoxide (12.6 g, 185 mmol) in ethanol (90 mL). The solution was stirred at 130° C. for 16 h. The cooled reaction mixture was concentrated to give 6-(1,1-difluoroethyl)-5-methylpyrimidine-2,4-diol (19 g) as a grey solid which was used in the next step without further purification.

A mixture of 6-(1,1-difluoroethyl)-5-methylpyrimidine-2,4-diol (7.5 g, 39 mmol) in phosphorus oxychloride (50 mL) and DMF (8 mL) was stirred at 100° C. for 5 h. The cooled reaction mixture was carefully poured into ice water (150 mL) and extracted with EtOAc (3×80 mL). The combined organic layers were washed with brine (2×100 mL), dried over $Na_2SO_4$, filtered and concentrated. The crude product was purified using column chromatography to give 2,4-dichloro-6-(1,1-difluoroethyl)-5-methylpyrimidine as a yellow oil (6.0 g, 67%).

$^1$H NMR (400 MHz, $CDCl_3$) δ: 2.59 (s, 3H), 2.01 (t, 3H).

(2S,3R)-3-hydroxy-2-methylazetidin-1-ium [(1R, 4S)-7,7-dimethyl-2-oxobicyclo[2.2.1]hept-1-yl] methanesulfonate

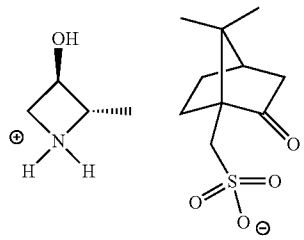

Step 1: (2R)-2-[(1R)-1-bromoethyl]oxirane

In three separate reaction vessels, a solution of (2E)-but-2-en-1-ol (967 g, 13.4 mol) in chloroform (10 L) was treated with bromine (2.15 kg, 13.4 mol) over the course of 2 h at 0° C. The mixture was stirred at 15° C. for 30 min. The mixtures were quenched with saturated sodium thiosulfate solution (500 mL) at 15° C. The three reaction mixtures were combined and extracted with DCM (3×5 L). The combined organics were concentrated in vacuo to give trans-2,3-dibromobutan-1-ol (10.5 kg, quant.) as yellow oil, which was taken to the next step without further purification. In three separate reaction vessels, a solution of KOH (711 g, 12.7 mol) in water (6 L) was added to a solution of trans-2,3-dibromobutan-1-ol (3.33 kg, 12.7 mol) in THF (9 L) dropwise at 15° C. The reaction mixture was stirred at rt for 2 h. The three reaction mixtures were combined and the organic layer was separated. The aqueous phase was extracted with EtOAc (3×5 L). The combined organic layers were washed with brine (5 L×3), dried with $Na_2SO_4$, filtered and concentrated in vacuo to give the title compound (6.5 kg, quant.) as a yellow oil, which was taken to next step without further purification.

$^1$H NMR (600 MHz, $CD_3OD$) δ: 3.86 (quin., 1H), 3.19-3.22 (m, 1H), 2.94 (t, 1H), 2.76-2.78 (m, 1H), 1.73 (d, 3H).

Step 2:
(2S,3R)-1-(diphenylmethyl)-2-methylazetidin-3-ol

In two separate reaction vessels, a solution of (2R)-2-[(1R)-1-bromoethyl]oxirane (3.28 kg, 16.2 mol) and benzhydrylamine (2.97 kg, 16.2 mol) in anhydrous ethanol (5.41

L) was treated with NaHCO$_3$ (2.07 kg, 24.34 mol) and the mixture was stirred at rt for 80 h. Then the mixture was stirred at 65° C. for an additional 24 h. The two reaction mixtures were cooled to rt, combined and filtered. The filtrate was concentrated. The residue was dissolved in DCM (10 L), washed with saturated aqueous ammonium chloride (2×5 L), dried over Na$_2$SO$_4$, filtered and concentrated. The crude product was purified by column chromatography on silica gel eluting with petroleum ether/EtOAc (50:1 to 1:1) to give the title compound (3.18 kg, ~80% purity, 36.5% yield) as yellow oil.

$^1$H NMR (400 MHz, CDCl$_3$) δ: 7.16-7.46 (m, 10H), 4.34 (s, 1H), 3.93 (q, 1H), 3.66 (t, 1H), 3.03 (q, 1H), 2.58 (t, 1H), 0.76 (d, 3H).

Step 3: (2S,3R)-1-(diphenylmethyl)-3-hydroxy-2-methylazetidinium [(1R,4S)-7,7-dimethyl-2-oxobicyclo[2.2.1]hept-1-yl]methanesulfonate To a solution of [(1R,4S)-7,7-dimethyl-2-oxobicyclo[2.2.1]hept-1-yl]methanesulfonic acid (2.7 kg, 12 mol) in ethanol (8 L) was added a solution of (2S,3R)-1-(diphenylmethyl)-2-methylazetidin-3-ol (3.18 kg, 11.7 mol) in ethanol (2 L). The resulting solution was evaporated to remove EtOH. The residue was treated with methyl tert-butyl ether (5 L) and evaporated until ~1 L of solvent remained. The residue was treated with additional methyl tert-butyl ether (5 L) and filtered. The filter cake was dried in vacuo to give a white solid (3.5 kg) which was dissolved in DCM (7.6 L) and EtOAc (10.9 L) was added. The mixture was stirred at rt for 30 min, resulting in the precipitation of white solids which were collected by filtration. The filter cake was suspended in DCM (10.6 L), stirred at rt for 10 min, and then EtOAc (10.6 L) was added to the solution. The mixture was stirred at rt for 30 min and the resulting white precipitates were collected by filtration. The filter cake was dissolved in DCM (10.6L), stirred at rt for 10 min, then EtOAc (10.6 L) was added. The reaction mixture was stirred at rt for 30 min, and the precipitated solids were collected by filtration to give a white solid (1.3 kg, ee=95.2% by chiral SFC). This material was dissolved in DCM (7 L) and heated to refluxed for 40 min. EtOAc (3.5 L) was added and the mixture was stirred at 40° C. for an additional 20 min and white solids precipitated. The solids were collected by filtration. The filter cake was dried in vacuo to give the title compound (1.1 kg, 98.2% ee by chiral SFC, 62.9% chiral resolution yield) as a white solid.

$^1$H NMR (600 MHz, CD$_3$OD) δ: 7.44-7.59 (m, 10H), 5.66 (s, 1H), 4.35-4.41 (m, 1H), 4.25-4.30 (m, 2H), 3.73-3.78 (m, 1H), 3.37 (d, 1H), 2.80 (d, 1H), 2.68-2.74 (m, 1H), 2.36 (dt, 1H), 2.02-2.09 (m, 2H), 1.91 (d, 1H), 1.60-1.66 (m, 1H), 1.40-1.45 (m, 1H), 1.16 (s, 3H), 1.09 (d, 3H), 0.88 (s, 3H).

Step 4

A partial solution of (2S,3R)-1-(diphenylmethyl)-3-hydroxy-2-methylazetidinium [(1R,4S)-7,7-dimethyl-2-oxobicyclo[2.2.1]hept-1-yl]methanesulfonate (18.96 g, 39.04 mmol) in methanol (60 mL) was treated with 10% palladium hydroxide on carbon (1.11 g) in a stainless steel reaction vessel. The reaction vessel was flushed with nitrogen gas then filled with hydrogen gas (60 psi). The reaction mixture was stirred at rt for 17 h, then re-pressurized with hydrogen gas (55 psi). After an additional 24 h, the reaction mixture was flushed with nitrogen gas and filtered through a plug of Celite®, eluting with methanol (4×80 mL). The combined filtrates were evaporated to give a white oily semi-solid. This material was suspended in heptane (100 mL), the sides of the flask were scrapped with a spatula, and the heptanes were decanted. This process was repeated two times, and the solids were suspended in heptanes (200 mL) and stirred at rt for 2.5 h. The solids were collected by filtration, suspended in heptanes (100 mL) and stirred at rt for 1 h. The solids were collected by filtration, suspended in heptanes (120 mL) and stirred vigorously for 24 h. The solids were collected by filtration to give (2S,3R)-3-hydroxy-2-methylazetidin-1-ium [(1R,4S)-7,7-dimethyl-2-oxobicyclo[2.2.1]hept-1-yl]methanesulfonate (11.8 g, 95%) as a white solid.

$^1$H NMR (600 MHz, CD$_3$OD) δ: 4.27-4.34 (m, 2H), 4.04-4.09 (m, 1H), 3.76-3.80 (m, 1H), 3.31 (d, 1H), 2.80 (d, 1H), 2.62-2.69 (m, 1H), 2.34-2.39 (m, 1H), 2.04-2.09 (m, 2H), 1.92 (d, 1H), 1.63-1.68 (m, 1H), 1.54 (d, 3H), 1.41-1.47 (m, 1H), 1.13 (s, 3H), 0.88 (s, 3H).

(2S,3R)-3-hydroxy-2,3-dimethylazetidinium [(1R,4S)-7,7-dimethyl-2-oxobicyclo[2.2.1]hept-1-yl]methanesulfonate

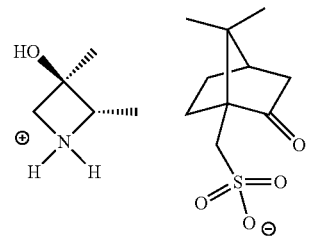

Step 1: tert-butyl [(2S)-4-chloro-3-oxobutan-2-yl]carbamate

Magnesium turnings (120 g, 4.90 mol) and iodine (50 mg) were combined in a three-necked 250 ml round bottom flask equipped with a reflux condenser. A solution of tert-butyl chloride (22.5 g, 245 mmol) in THF (80 mL) was added followed by ethyl bromide (5 mL). The reaction was heated to 60° C., and vigorous bubbling was observed. Additional tert-butyl chloride (428 g, 4.65 mol) in THF (1.52 L) was added dropwise via addition funnel at such a rate that a gentle reflux is maintained. After the addition was complete, the dark solution with Mg turnings was heated at 60° C. for 30 min then cooled to 0° C. To the cooled Grignard solution was added triethylamine (120 g, 1.19 mol) and solid sodium chloroacetic acid (139 g, 1.19 mol). A solution of Boc-L-alanine methyl ester (157 g, 0.77 mol) in toluene (900 mL) was then added dropwise. The reaction was warmed to rt and stirred for 16 h. The reaction was then cooled to 0° C., and acetic acid (320 g, 5.50 mol) in water (640 mL) was added dropwise. Aqueous 2M HCl (70 mL) was added to adjust the aqueous layer to pH=~4 to 5. The reaction was stirred at rt for 45 min until gas evolution ceased. The layers were separated and the aqueous layer was extracted with EtOAc (500 mL). The combined organic layers were washed with saturated aqueous NaHCO$_3$ (60 mL) and brine (30 mL). The organic layers were dried over anhydrous Na$_2$SO$_4$ and concentrated to give a yellow oil. Heptane (300 mL) was added to the oil and stirred at rt for 30 min. The resulting solid is filtered and washed with heptane to give the title compound (105 g, 61%) as a white solid.

¹H NMR (400 MHz, CDCl₃) δ: 5.08 (br. s, 1H), 4.50-4.57 (m, 1H), 4.23-4.32 (m, 2H), 1.44 (s, 9H), 1.36 (d, 3H).

Step 2: tert-butyl [(2S,3S)-4-chloro-3-hydroxy-3-methylbutan-2-yl]carbamate

To a solution of tert-butyl [(2S)-4-chloro-3-oxobutan-2-yl]carbamate (90 g, 0.40 mol) in DCM (2.0 L) cooled to −70° C. was added methyl magnesium bromide (460 mL, 1.38 mol, 3 M in diethyl ether) dropwise. The mixture was stirred at −70° C. for 1 h and then warmed to ~−5° C. and stirred for 5 h. The reaction mixture was quenched with saturated aqueous ammonium chloride (500 mL) dropwise at a rate so that the internal temperature did not rise above 10° C. The grey suspension became milky white, and then the pH was adjusted to ~2 with 2N aqueous HCl. The organic layer was separated, and the aqueous layer was extracted with DCM (3×800 mL). The combined organic layers were washed with brine, dried over anhydrous Na₂SO₄ and concentrated in vacuo. The crude product was dissolved in hexane/EtOAc (10/1, 200 mL). The yellow mixture was warmed to 50° C., stirred for 10 min and then slowly cooled to 0° C. A solid formed which was filtered to give the title compound (45 g, 47%) as a white solid.

¹H NMR (400 MHz, CDCl₃) δ: 4.72 (br. s, 1H), 3.77-3.87 (m, 1H), 3.60 (d, 1H), 3.52 (d, 1H), 1.46 (s, 9H), 1.30 (s, 3H), 1.21 (d, 3H).

Step 3

To a solution of the tert-butyl [(2S,3S)-4-chloro-3-hydroxy-3-methylbutan-2-yl]carbamate (55 g, 0.23 mmol) in DCM (20 mL) and methanol (100 mL) was added 4N HCl in dioxane (150 mL) at 0° C. The brown mixture was warmed to 20° C. and stirred for 2.5 h. The brown mixture was concentrated to give a brown oil (40 g, 100%) that was dissolved in CH₃CN (300 mL) and treated with solid NaHCO₃ (146 g, 1.74 mol). The white suspension was stirred at 70° C. for 4 hours, then cooled to rt, filtered through Celite® and washed with acetonitrile. The yellow filtrate was concentrated in vacuo to give (2S,3R)-2,3-dimethylazetidin-3-ol (22 g, 75%) as a brown oil. The compound was used in the subsequent step without further purification.

A yellow solution of (2S,3R)-2,3-dimethylazetidin-3-ol (23.4 g, 0.23 mol) in acetonitrile (130 mL) was added [(1R,4S)-7,7-dimethyl-2-oxobicyclo[2.2.1]hept-1-yl]methanesulfonic acid (48 g, 0.21 mol) and stirred at 15° C. for 4 h. The formed precipitate was collected by filtration to give (2S,3R)-3-hydroxy-2,3-dimethylazetidinium [(1R,4S)-7,7-dimethyl-2-oxobicyclo[2.2.1]hept-1-yl]methanesulfonate (50 g, 65%) as a white solid.

¹H NMR (400 MHz, CD₃OD) δ: 4.36 (q, 1H), 3.89 (d, 1H), 3.76 (d, 1H), 3.32 (d, 1H), 2.80 (d, 1H), 2.63-2.72 (m, 1H), 2.36 (dt, 1H), 2.02-2.10 (m, 2H), 1.93 (d, 1H), 1.60-1.68 (m, 1H), 1.42-1.48 (m, 7H), 1.16 (s, 3H), 0.88 (s, 3H).

(2S)-2-methylazetidinium [(1R,4S)-7,7-dimethyl-2-oxobicyclo[2.2.1]hept-1-yl]methanesulfonate

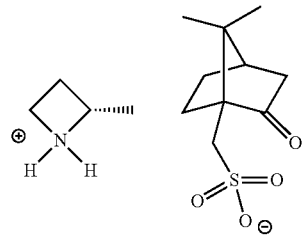

Step 1: (2S)-1-(diphenylmethyl)-2-methylazetidinium [(1R,4S)-7,7-dimethyl-2-oxobicyclo[2.2.1]hept-1-yl]methanesulfonate A solution of R-(−)-1,3-butanediol (20.0 g, 222 mmol) and DIPEA (101.5 mL, 585.0 mmol) in acetonitrile (444 mL) was cooled to −30° C. and treated with trifluoromethanesulfonic anhydride (81.2 mL, 480 mmol) dropwise via addition funnel over 90 min, maintaining the internal reaction temperature between −30 and −35° C. After the addition was complete, the reaction mixture was stirred for 10 min at −30° C. and then treated with additional trifluoromethanesulfonic anhydride (1.5 mL) dropwise and stirred at −30° C. for an additional 15 min. The reaction mixture was then treated with additional DIPEA (101.5 mL, 585.0 mmol) over the course of 15 min while maintaining the internal temperature at −30° C. After an additional 10 min at −30° C. the reaction mixture was treated with a solution of benzhydrylamine (38 mL) in acetonitrile (40 mL) dropwise over 30 min via an addition funnel, maintaining the internal reaction temperature below −30° C. The reaction mixture was stirred at −30° C. for 20 min then placed in an ice water bath for 30 min. The reaction was then stirred at rt for 30 min, followed by heating at 45° C. for 30 min. The reaction mixture was cooled to rt, poured into deionized water (900 mL) and extracted with toluene (1 L). The aqueous phase was back-extracted with toluene (300 mL) and the combined organic layers were washed with water (2×250 mL), dried over Na₂SO₄, filtered and evaporated. The crude product was dissolved in DCM (300 mL) and loaded onto a plug of silica gel (300 mL SiO₂, preflushed with 1:1 heptane/EtOAc). The plug was flushed with 1:1 heptane/EtOAc (1.2 L) and the filtrate was evaporated to give a red oil (50.2 g). The crude product was dissolved in methanol (200 mL), placed in a water bath at 10° C., and treated with [(1R,4S)-7,7-dimethyl-2-oxobicyclo[2.2.1]hept-1-yl]methanesulfonic acid (49 g) in batches over 5 minutes. The solution was stirred at rt for 2 h, the solvent was evaporated and the solids were dried under high vacuum for 15 h to give a solid (99.2 g). The solid was dissolved in DCM (100 mL) and stirred at rt for 10 min to give a dark solution. EtOAc (850 mL) was added slowly with stirring and solids precipitated from solution after ~5 min. The suspension was stirred at rt for 2 h, and the solids were collected by filtration and washed with EtOAc (50 mL). The solids were dissolved in DCM (100 mL) and EtOAc (700 mL) was added. The mixture was stirred at rt and solids immediately precipitated from solution. The suspension was stirred at rt for 15 h, then the solids were collected by filtration, washed with EtOAc (50 mL)

and dried under reduced pressure to give the title compound (66.7 g, 65% yield) as a white solid.

$^1$H NMR (500 MHz, CD$_3$OD) δ: 7.54-7.59 (m, 4H), 7.43-7.53 (m, 6H), 5.67 (s, 1H), 4.69-4.76 (m, 1H), 3.97-4.02 (m, 2H), 3.36 (d, 1H), 2.81 (d, 1H), 2.70-2.75 (m, 1H), 2.58-2.64 (m, 1H), 2.31-2.39 (m, 2H), 2.03-2.09 (m, 2H), 1.91 (d, 1H), 1.62-1.66 (m, 1H), 1.41-1.47 (m, 1H), 1.16 (s, 3H), 1.11 (d, 3H), 0.88 (s, 3H); Elemental analysis: Calculated for C$_{27}$H$_{35}$NO$_4$S: C=69.05%, H=7.51%, N=2.98%; Found: C=68.90%, H=7.59%, N=2.91%.

Step 2

A 300 mL stainless steel reactor was charged with solution of (2S)-1-(diphenylmethyl)-2-methylazetidinium [(1R,4S)-7,7-dimethyl-2-oxobicyclo[2.2.1]hept-1-yl]methanesulfonate (29.4 g, 62.6 mmol) in methanol (125 mL) and 20% Pd(OH)$_2$/C (1.78 g). The reactor was flushed with nitrogen three times and then hydrogen three times and then pressurized to 60 psi hydrogen and stirred at rt for 16 h. The hydrogen was released and the reactor was flushed with nitrogen. The reaction mixture was filtered through a pad of Celite®, eluting with methanol (100 mL), and the filtrate was concentrated in vacuo to give a white solid. The white solid was suspended in a mixture of EtOAc/methyl tert-butyl ether (1:1, 200 mL) and stirred for 1 h at 60° C. After cooling to rt, the slurry was stirred for an additional hour and the solids were collected by filtration. The resulting solids are suspended in methyl tert-butyl ether (100 mL) and stirred at rt for 16 hours. The solids were collected by filtration, washed with methyl tert-butyl ether (25 mL) and dried under reduced pressure to give (2S)-2-methylazetidinium [(1R,4S)-7,7-dimethyl-2-oxobicyclo[2.2.1]hept-1-yl]methanesulfonate (18.1 g, 95%) as a white solid.

$^1$H NMR (500 MHz, CD$_3$OD) δ: 4.59-4.66 (m, 1H), 4.05 (q, 1H), 3.92 (td, 1H), 3.32 (m, 1H), 2.80 (d, 1H), 2.59-2.70 (m, 2H), 2.36 (dt, 1H), 2.25-2.32 (m, 1H), 2.03-2.10 (m, 2H), 1.92 (d, 1H), 1.62-1.68 (m, 1H), 1.57 (d, 3H), 1.41-1.47 (m, 1H), 1.15 (s, 3H), 0.89 (s, 3H); Elemental analysis: Calculated for C$_{14}$H$_{25}$NO$_4$S: C=55.42%, H=8.31%, N=4.62%; Found: C=55.59%, H=8.41%, N=4.49%.

(2S)-2-methylazetidine hydrochloride

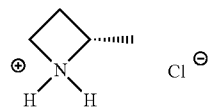

Step 1: (2R)-4-[(methylsulfonyl)oxy]butan-2-yl methanesulfonate

A solution of (3R)-butane-1,3-diol (3 g, 30 mmol) and triethylamine (10.1 g, 99.9 mmol) in DCM (60 mL) was cooled to 0° C. and treated with methanesulfonyl chloride (11.4 g, 99.9 mmol) in a dropwise manner at 0° C. After 15 min the ice-water bath was removed and the mixture was stirred at rt for 2 h. The mixture was diluted with aqueous saturated ammonium chloride (80 mL) and extracted with DCM (3×50 mL). The combined organic layers were washed with brine, dried over Na$_2$SO$_4$ and concentrated to give a residue. The residue was purified using column chromatography eluting with EtOAc/petroleum ether (1:4 to 3:2) to give the title compound (7.3 g, 89%) as a colourless oil.

$^1$H NMR (400 MHz, CDCl$_3$) δ: 5.00 (s, 1H), 4.35 (t, 2H), 3.07 (s, 3H), 3.06 (s, 3H), 2.05-2.12 (m, 2H), 1.50 (d, 3H).

Step 2

(2R)-4-[(methylsulfonyl)oxy]butan-2-yl methanesulfonate (7.20 g, 29.2 mmol) was dissolved in benzylamine (19.2 mL, 175 mmol) and stirred at 45° C. for 16 h. The reaction mixture was cooled to rt and a mixture of cyclohexane/methyl tert-butyl ether (1:1) was added, resulting in the precipitation of white solids. The precipitates were removed by filtration and the filtrate was evaporated under reduced pressure and purified using column chromatography eluting with DCM and 1% ammonium hydroxide/methanol, 100:0 to 99.5:0.5) to give a light yellow oil (2.5 g, 53%). This yellow oil (2.28 g, 14.1 mmol) was dissolved in methanol (50 mL) and treated with 10% palladium hydroxide on carbon (500 mg). The resulting suspension was heated to 50° C. under an atmosphere of hydrogen gas (30 PSI) for 20 h, then heated to 60° C. and stirred under hydrogen (30 PSI) for an additional 40 h. The cooled reaction mixture was filtered and the filtrated with treated with 4N HCl in EtOAc (15 mL) and stirred at rt for 30 min. The mixture was concentrated to give (2S)-2-methylazetidine hydrochloride (1.47 g, 96.6%) as a white gum.

$^1$H NMR (400 MHz, CDCl$_3$) δ: 4.50-4.60 (m, 1H), 3.97-4.04 (m, 1H), 3.75-3.90 (m, 1H), 2.58-2.65 (m, 1H), 2.26-2.35 (m, 1H), 1.54 (d, 3H).

ethyl (1R,5S,6S)-3-azabicyclo[3.1.0]hex-6-ylacetate

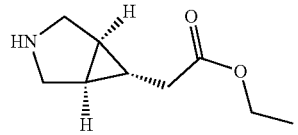

Step 1: [(1R,5S,6r)-3-benzyl-3-azabicyclo[3.1.0]hex-6-yl]methyl methanesulfonate The preparation of [(1R,5S,6r)-3-benzyl-3-azabicyclo[3.1.0]hex-6-yl]methanol is described in Berliner, M. A.; et al. *Org. Process Res. Dev.* 2011, 15, 1052-1062.

To a solution of [(1R,5S,6r)-3-benzyl-3-azabicyclo[3.1.0]hex-6-yl]methanol (95.0 g, 396 mmol) in dry THF (1230 mL) and DMF (95 mL) was added triethylamine (241 g, 2.38 mol) at 0° C. The mixture was stirred at 0° C. for 5 min and treated with methanesulfonyl chloride (82.22 g, 717.8 mmol) dropwise over 5 min. The mixture was stirred at 10° C. for 16 h. The reaction was quenched with addition of saturated NaHCO$_3$ (1000 mL) and then the mixture was extracted with methyl tert-butyl ether (5×500 mL). The organic phase was concentrated in vacuo to give the title compound (99 g, 89%) as a brown oil.

MS (ES+): 281.9 (M+H).

Step 2: [(1R,5S,6S)-3-benzyl-3-azabicyclo[3.1.0]hex-6-yl]acetonitrile

To a solution of [(1R,5S,6r)-3-benzyl-3-azabicyclo[3.1.0]hex-6-yl]methyl methanesulfonate (99 g, 352 mmol) in DMF (700 mL) was added sodium cyanide (18.49 g, 377.3 mmol) at 20° C. The mixture was stirred at 20° C. for 16 h. Saturated aqueous NaHCO₃ was added to the reaction (200 mL) and the mixture was extracted with methyl tert-butyl ether (2×150 mL). The organics were dried over Na₂SO₄, filtered and concentrated to give a brown oil (50 g). The brown oil was purified by column chromatography on silica gel eluting with petroleum ether/EtOAc (10:1 to 5:1) to give the title compound (37 g, 50%) as a yellow oil.

MS (APCI): 213.1 (M+H).

Step 3: ethyl [(1R,5S,6S)-3-benzyl-3-azabicyclo[3.1.0]hex-6-yl]acetate

To ethanol (215 mL) was added concentrated sulfuric acid (108 mL) at 0° C. The mixture was stirred at 10° C. for 5 min, then re-cooled to 0° C. A solution of [(1R,5S,6S)-3-benzyl-3-azabicyclo[3.1.0]hex-6-yl]acetonitrile (37 g, 170 mmol) in EtOH (95 mL) was added to the mixture of EtOH and sulfuric acid at 0° C. The mixture was stirred at 80° C. for 16 h. The mixture was adjusted to pH=9 with 5M NaOH at 0° C., and the product was extracted with EtOAc (5×500 mL). The combined organics were dried over Na₂SO₄, filtered and concentrated to give a yellow oil (45 g). The yellow oil was purified by column chromatography on silica gel eluting with petroleum ether/EtOAc (10:1 to 5:1) to give the title compound (37 g, 82%) as yellow oil.

MS (APCI): 260.1 (M+H).

Step 4: ethyl (1R,5S,6S)-3-azabicyclo[3.1.0]hex-6-ylacetate

To a solution of ethyl [(1R,5S,6S)-3-benzyl-3-azabicyclo[3.1.0]hex-6-yl]acetate (37 g, 140 mmol) in EtOH (1500 mL) was added 10% palladium hydroxide on carbon (5 g, 4 mmol). The mixture was degassed and refilled three times with nitrogen and degassed and then refilled for three times with hydrogen gas. The mixture was stirred under an atmosphere of hydrogen (50 PSI) at 50° C. for 16 h. The cooled reaction mixture was flushed with nitrogen, filtered, and the filter cake was washed with MeOH (500 mL). The filtrate was concentrated in vacuo to give ethyl (1R,5S,6S)-3-azabicyclo[3.1.0]hex-6-ylacetate (22 g, 91%) as yellow oil.

MS (ES+): 170.1 (M+H).

ethyl (1R,5S,6S)-3-azabicyclo[3.1.0]hex-6-ylacetate trifluoroacetic acid salt

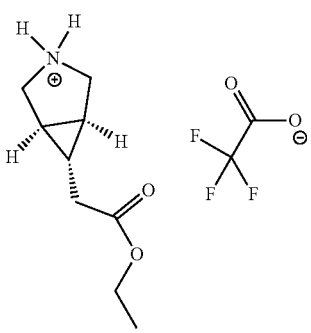

MFCD12198681) in DCM (12 mL) was added ethanol (0.4 mL), 4-dimethylaminopyridine (203 mg, 1.66 mmol) and N,N'-dicyclohexylcarbodiimide (342 mg, 1.66 mmol) at rt. The resulting colorless suspension was stirred at rt for 16 h. The mixture was diluted with water (15 mL) and aqueous ammonium chloride (10 mL). The product was extracted with DCM (3×25 mL). The combined organic layers were washed with brine, dried over Na₂SO₄ and concentrated to give a residue (650 mg) as white solid, which was purified by flash column chromatography, eluting with EtOAc/petroleum ether (1% to 11% EtOAc) to give the title compound (350 mg, 78%) as a colorless oil.

¹H NMR (400 MHz, CDCl₃) δ 4.15 (q, 2H), 3.53-3.64 (m, 2H), 3.29-3.37 (m, 2H), 2.17-2.32 (m, 2H), 1.44 (s, 9H), 1.35-1.38 (m, 2H), 1.27 (t, 3H), 0.88-0.92 (m, 1H).

Step 2

To a solution of tert-butyl (1R,5S,6S)-6-(2-ethoxy-2-oxoethyl)-3-azabicyclo[3.1.0]hexane-3-carboxylate (340 mg, 1.26 mmol) in DCM (6 mL) was added TFA (5 mL). The mixture was stirred at rt for 1 h. The mixture was concentrated to dryness to give ethyl (1R,5S,6S)-3-azabicyclo[3.1.0]hex-6-ylacetate trifluoroacetic acid salt (400 mg, 99%) as a brown liquid.

¹H NMR (400 MHz, CD₃OD) δ 4.13 (q, 2H), 3.37-3.45 (m, 4H), 2.35 (d, 2H), 1.72-1.77 (m, 2H), 1.25 (t, 3H), 1.06-1.12 (m, 1H).

ethyl (1R,5S,6S)-3-azabicyclo[3.1.0]hex-6-ylacetate hydrochloride

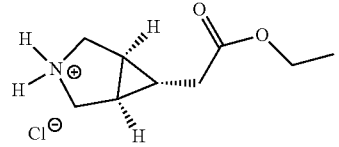

Step 1: tert-butyl (1R,5S,6r)-6-(bromomethyl)-3-azabicyclo[3.1.0]hexane-3-carboxylate To a solution of tert-butyl (1R,5S,6r)-6-(hydroxymethyl)-3-azabicyclo[3.1.0]hexane-3-carboxylate (5.1 g, 23.91 mmol, MFCD14525755) in DCM (180 mL) was added carbon tetrabromide (11.9 g, 35.9 mmol) and triphenylphosphine (9.41 g, 35.9 mmol) at 5° C. The reaction mixture was warmed to rt and stirred for 12 h. The reaction mixture was evaporated to dryness and purified using column chromatography eluting with petroleum ether/EtOAc (100:1 to 10:1) to give the title compound (5.6 g, 85%) as a yellow oil.

¹H NMR (400 MHz, CD₃OD) δ 3.54 (d, 2H), 3.32-3.43 (m, 4H), 1.61-1.64 (m, 2H), 1.46 (s, 9H), 1.03-1.05 (m, 1H).

Step 2: tert-butyl (1R,5S,6S)-6-(cyanomethyl)-3-azabicyclo[3.1.0]hexane-3-carboxylate To a solution of tert-butyl (1R,5S,6r)-6-(bromomethyl)-3-azabicyclo[3.1.0]hexane-3-carboxylate (6000 mg, 21.73 mmol) in DMF (150 mL) was added sodium cyanide (1600 mg, 32.6 mmol) at rt and the reaction mixture was stirred for 16 h at rt. The yellow mixture was diluted with EtOAc (100 mL), washed with brine (100 mL). The organic layer was dried over Na₂SO₄, filtered and evaporated to afford a

Step 1: tert-butyl (1R,5S,6S)-6-(2-ethoxy-2-oxoethyl)-3-azabicyclo[3.1.0]hexane-3-carboxylate To a solution of [(1R,5S,6S)-3-(tert-butoxycarbonyl)-3-azabicyclo[3.1.0]hex-6-yl]acetic acid (400 mg, 1.66 mmol, yellow oil, that was purified using column chromatography eluting with petroleum ether/EtOAc (100:1 to 5:1) to give the title compound (4.0 g, 83%) as a yellow oil.

$^1$H NMR (400 MHz, CDCl$_3$) δ 3.58 (dd, 2H), 3.30-3.35 (m, 2H), 2.45-2.51 (m, 1H), 2.31-2.36 (m, 1H), 1.49-1.52 (m, 2H), 1.41 (s, 9H), 0.88-0.91 (m, 1H).

Step 3

Acetyl chloride (300 mg, 3.82 mmol) was added to dry ethanol (2.5 mL) at 0° C. and stirred at rt for 1 h in sealed flask. Tert-butyl (1R,5S,6S)-6-(cyanomethyl)-3-azabicyclo[3.1.0]hexane-3-carboxylate (85 mg, 0.38 mmol) was added to the solution and the mixture was stirred at 70° C. for 68 h. The solution was cooled to rt and concentrated to give ethyl (1R,5S,6S)-3-azabicyclo[3.1.0]hex-6-ylacetate hydrochloride (80 mg, >99%) as a white solid.

$^1$H NMR (400 MHz, CD$_3$OD) δ 4.15-4.18 (m, 2H), 3.44-3.47 (m, 4H), 2.36-2.38 (m, 2H), 1.74-1.78 (m, 2H), 1.25-1.30 (m, 3H), 1.14-1.17 (m, 1H).

methyl (1R,5S,6S)-3-azabicyclo[3.1.0]hex-6-ylacetate hydrochloride

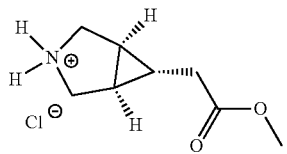

Step 1: (1R,5S,6r)-3-benzyl-6-(chloromethyl)-3-azabicyclo[3.1.0]hexane

The preparation of [(1R,5S,6r)-3-benzyl-3-azabicyclo[3.1.0]hex-6-yl]methanol is described in Berliner, M. A.; et al. *Org. Process Res. Dev.* 2011, 15, 1052-1062.

To a stirred solution of [(1R,5S,6r)-3-benzyl-3-azabicyclo[3.1.0]hex-6-yl]methanol (620 g, 3.05 mol) in methanol (600 mL) was added 4M HCl in methanol (6.2 L) at 10° C. over a period of 45 min and the mixture was stirred for 15 min. The reaction mixture slowly heated to 25-30° C. for 2 h. The solvent was evaporated under reduced pressure to afford crude product. The crude product was triturated with ether (1.5 L) to give [(1R,5S,6r)-3-benzyl-3-azabicyclo[3.1.0]hex-6-yl]methanol hydrochloride (703 g, 96% yield) as pale brown solid which was used directly in the next step.

To a stirred solution of [(1R,5S,6r)-3-benzyl-3-azabicyclo[3.1.0]hex-6-yl]methanol hydrochloride (699 g, 2.91 mol) in toluene (1.4 L) was added thionyl chloride (693 g, 5.83 moles) at 5 to 10° C. over a period of 30 min and stirred for 15 min. The reaction mixture temperature was slowly warmed to 45° C. and stirred for 30 min. The reaction mixture was cooled to rt and concentrated under reduced pressure. The crude product was dissolved in EtOAc (5 L) and saturated NaHCO$_3$ solution (3 L, pH=~8) and stirred for 1 h, then the layers were separated. The aqueous layer was further extracted with EtOAc (2×2 L). The combined organic layers were washed with brine solution (2.0 L), dried over anhydrous Na$_2$SO$_4$ and evaporated under reduced pressure to give the title compound (611 g, 95%) as a brown color liquid.

$^1$H NMR (600 MHz, DMSO-d$_6$) δ 7.30 (t, 2H), 7.20-7.25 (m, 3H), 3.51-3.56 (m, 4H), 2.87 (d, 2H), 2.29 (d, 2H), 1.54-1.57 (m, 1H), 1.43 (s, 2H).

Step 2: [(1R,5S,6S)-3-benzyl-3-azabicyclo[3.1.0]hex-6-yl]acetonitrile

To a stirred solution of (1R,5S,6r)-3-benzyl-6-(chloromethyl)-3-azabicyclo[3.1.0]hexane (664 g, 2.99 mol) in DMF (2.9 L) was added sodium cyanide (191 g, 3.89 mol) at rt and the mixture was slowly heated to 50° C. for 48 h. The reaction mixture was cooled to rt, quenched with water (10 L) and extracted with EtOAc (3×4 L). The combined organic layers were washed with water (5 L), brine (3 L), dried over anhydrous Na$_2$SO$_4$ and evaporated under reduced pressure. The crude product was purified using column chromatography eluting with 20% EtOAc in petroleum ether to give the title compound (593 g, 93.2%) as a brown color liquid.

$^1$H NMR (600 MHz, DMSO-d$_6$) δ 7.27-7.32 (m, 2H), 7.19-7.26 (m, 3H), 3.54 (s, 2H), 2.87 (d, 2H), 2.45 (d, 2H), 2.28 (d, 2H), 1.33-1.41 (m, 3H).

Step 3: methyl [(1R,5S,6S)-3-benzyl-3-azabicyclo[3.1.0]hex-6-yl]acetate

Acetyl chloride (2.21 kg, 28.3 mol) was added to methanol (3.77 L) at 0° C. over a period of 1 h. The reaction temperature was slowly heated to 45° C. for 30 min. The reaction mixture was again cooled to 0° C. and added a solution of [(1R,5S,6S)-3-benzyl-3-azabicyclo[3.1.0]hex-6-yl]acetonitrile (400 g, 1.88 mol) in methanol (700 mL) was added over a period of 2 h at 0° C. The resulting solution was slowly heated to 65° C. for 4 h. The reaction mixture was cooled to rt and concentrated under reduced pressure. The crude was dissolved in EtOAc (6 L) and saturated NaHCO$_3$ solution (4 L, pH ~8) and stirred for 1 h. The layers were separated and the aqueous layer was further extracted with EtOAc (2×1 L). The combined organic layers were washed with brine solution (2.0 L), dried over anhydrous Na$_2$SO$_4$ and evaporated under reduced pressure to give the title compound (377 g, 82%) as a brown color liquid.

$^1$H NMR (600 MHz, CDCl$_3$) δ 7.19-7.31 (m, 5H), 3.67 (s, 3H), 3.56 (s, 2H), 2.99 (d, 2H), 2.34 (d, 2H), 2.18 (d, 2H), 1.50-1.54 (m, 1H), 1.23 (s, 2H).

Step 4

To a solution of methyl [(1R,5S,6S)-3-benzyl-3-azabicyclo[3.1.0]hex-6-yl]acetate (542 g, 2.21 mol) in methanol (550 mL) was added 4M HCl in methanol (5.4 L) at 10° C. over a period of 30 min. The reaction mixture was warmed to rt and stirred for 2 h. The solvent was evaporated under reduced pressure. The crude product was triturated with ether (1.5 L) to give an off-white solid (545 g, 87.7% yield) that was used directly in the next step. The crude product (420 g, 149 moles) was dissolved in methanol (4 L) in an autoclave and treated with 10% Pd(OH)$_2$/C (41.4 g, 50% wet) under nitrogen, the autoclave was evacuated twice with nitrogen and placed under an atmosphere of hydrogen gas (100 psi) and heated to 70° C. for 8 h. The reaction mixture was cooled to rt and stirred for 4 h. The reaction mixture was filtered through a bed of Celite®, washing with methanol (2×1 L). The filtrate was evaporated under reduced pressure. The crude product was triturated with ether (1 L) and the solids were collected by filtration to give the methyl (1R,5S,6s)-3-azabicyclo[3.1.0]hex-6-ylacetate hydrochloride (345 g, 99% yield) as an off-white solid.

¹H NMR (600 MHz, DMSO-d₆) δ: 9.25-9.80 (br. s, 2H), 4.05-4.44 (br. s, 1H), 3.2-3.4 (br. s, 1H), 3.21 (s, 3H), 3.15 (s, 2H), 2.30 (d, 2H), 1.60 (s, 2H), 1.20-1.27 (m, 1H).

2,6-dichloro-4-(1,1-difluoroethyl)-5-fluoropyridine-3-carbonitrile

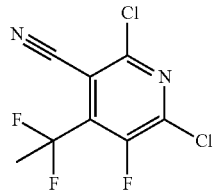

Step 1: 4-(1,1-difluoroethyl)-5-fluoro-2,6-dihydroxypyridine-3-carbonitrile

To a solution of ethyl 2,2-difluoropropanoate (10.0 g, 72.4 mmol) in THF (10.0 mL) was added sodium hydride (60% in mineral oil, 3.19 g, 79.6 mmol) and the mixture was heated to 50° C. Ethyl fluoroacetate (15.4 g, 145 mmol) was added dropwise over 1 min and the reaction was stirred at 50° C. for 2 h. The solution was poured into aqueous ammonium chloride (100 mL) at 0° C. The mixture was extracted with EtOAc (3×150 mL), washed with brine (100 mL), dried over Na₂SO₄, filtered and concentrated to give a yellow oil (13 g). The crude product was dissolved in ethanol (200 mL) and treated with 2-cyanoacetamide (5.52 g, 65.6 mmol) and piperidine (5.59 g, 65.6 mmol). The resulting colorless solution was stirred at 50° C. for 16 h. The product precipitated out of solution and was collected by filtration to give the title compound (10 g, 70%) as a white solid.

¹H NMR (400 MHz, DMSO-d₆) δ: 8.20 (br. s, 2H), 1.89 (t, 3H).

Step 2

A mixture of 4-(1,1-difluoroethyl)-5-fluoro-2,6-dihydroxypyridine-3-carbonitrile (10.0 g, 45.8 mmol) and phosphorus pentachloride (95.5 g, 458 mmol) was stirred at 130° C. for 32 h. The reaction mixture was cooled to rt and poured into aqueous NaHCO₃ (750 mL) at 0° C. The product was extracted with EtOAc (3×150 mL), washed with brine (150 mL), dried over Na₂SO₄, filtered and concentrated to give a yellow oil. The crude product was purified by column chromatography (EtOAc/petroleum ether from 0:100 to 3:97) to give 2,6-dichloro-4-(1,1-difluoroethyl)-5-fluoropyridine-3-carbonitrile (6.0 g, 51%) as a yellow oil.

¹H NMR (400 MHz, DMSO-d₆) δ: 2.10 (t, 3H).

2,4-dichloro-6-(1,1-difluoroethyl)pyridine

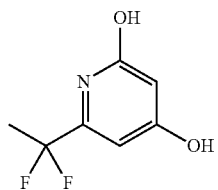

Step 1: 6-(1,1-difluoroethyl)pyridine-2,4-diol

A suspension of ethyl 6-(1,1-difluoroethyl)-2,4-dihydroxypyridine-3-carboxylate (10.5 g, 42.5 mmol) in 6N HCl (100 mL) was stirred at 100° C. for 16 h. The reaction mixture was cooled to rt and evaporated under reduced pressure to give the title compound (8.0 g, 90%) as a white solid.

¹H NMR (400 MHz, DMSO-d₆) δ: 7.9-8.6 (m, 2H), 6.62 (s, 1H), 6.27 (s, 1H), 1.95 (t, 3H).

Step 2: 2,4-dichloro-6-(1,1-difluoroethyl)pyridine

A mixture of 6-(1,1-difluoroethyl)pyridine-2,4-diol (7.0 g, 33 mmol) and phosphorus pentachloride (34.4 g, 165 mmol) was stirred at 125° C. for 20 h. The mixture was quenched with ice-water (200 mL), and extracted with EtOAc (2×100 mL). The organic phase was dried over Na₂SO₄, filtered and concentrated. The crude product was purified using column chromatography eluting with petroleum ether to give 2,4-dichloro-6-(1,1-difluoroethyl)pyridine (2.5 g, 36% yield) as a light yellow oil.

MS (ES+): 211.6 (M+H).

EXAMPLES

Example 1: [(1R,5S,6R)-3-{5-cyano-6-[(2S,3R)-3-hydroxy-2-methylazetidin-1-yl]-4-(trifluoromethyl)pyridin-2-yl}-3-azabicyclo[3.1.0]hex-6-yl]acetic acid

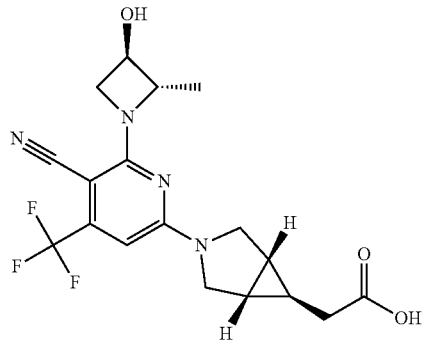 [SMILES: C[C@H]1[C@H](O)CN1c1nc(N2C[C@@H]3[C@@H](CC(=O)O)[C@@H]3C2)cc(C(F)(F)F)c1C#N]

Step 1: ethyl {(1R,5S,6S)-3-[6-chloro-5-cyano-4-(trifluoromethyl)pyridin-2-yl]-3-azabicyclo[3.1.0]hex-6-yl}acetate A suspension of 2,6-dichloro-4-(trifluoromethyl)pyridine-3-carbonitrile (2.4 g, 9.8 mmol), ethyl (1R,5S,6S)-3-azabicyclo[3.1.0]hex-6-ylacetate (1.7 g, 9.8 mmol) and NaHCO₃ (2.6 g, 31 mmol), in ethanol (25 mL) was stirred at rt overnight. The reactions mixture was concentrated, diluted with saturated aqueous NaHCO₃ and extracted with EtOAc (3×25 mL). The combined organics were washed with water, dried over Na₂SO₄, filtered and concentrated. The crude was purified by silica gel chromatography (10-35% EtOAc in n-heptane) to afford the title compound as an off-white solid (2.2 g, 57%).

MS (ES+): 374.2 (M+H), ¹H NMR (600 MHz, DMSO-d₆) δ: 6.90 (s, 1H), 4.07 (q, 2H), 3.79 (m, 2H), 3.67-3.53 (m, 2H), 2.43-2.21 (m, 2H), 1.75-1.57 (m, 2H), 1.19 (t, 3H), 0.81 (dt, 1H).

Step 2: ethyl [(1R,5S,6R)-3-{5-cyano-6-[(2S,3R)-3-hydroxy-2-methylazetidin-1-yl]-4-(trifluoromethyl)pyridin-2-yl}-3-azabicyclo[3.1.0]hex-6-yl]acetate Ethyl {(1R,5S,6S)-3-[6-chloro-5-cyano-4-(trifluoromethyl)pyridin-2-yl]-3-azabicyclo[3.1.0]hex-6-yl}acetate (2.1 g, 5.7 mmol), (2S,3R)-3-hydroxy-2-methylazetidin-1-ium [(1R,4S)-7,7-dimethyl-2-oxobicyclo[2.2.1]hept-1-yl]methanesulfonate (2.0 g, 6.2 mmol), NaHCO₃ (1.7 g, 20 mmol) were suspended in ethanol and stirred at 80° C. for 18 h. The reaction was diluted with saturated NaHCO₃ (200 mL) and extracted with EtOAc (3×100 mL). The combined organics were dried over Na₂SO₄, filtered and concentrated. The resultant white solid was carried forward to the next step without purification.
MS (ES+): 447.0 (M+Na).

Step 3

Sodium hydroxide (40 mL, 1M aq) was added to a suspension of ethyl [(1R,5S,6R)-3-{5-cyano-6-[(2S,3R)-3-hydroxy-2-methylazetidin-1-yl]-4-(trifluoromethyl)pyridin-2-yl}-3-azabicyclo[3.1.0]hex-6-yl]acetate (2.5 g, 5.9 mmol) in ethanol (80 mL) and the reaction was stirred at rt for 1 h. The reaction was concentrated, diluted with water (25 mL), acidified with 1 N HCl to pH=2, and extracted with EtOAc (3×25 mL). The combined organics were dried over Na₂SO₄, filtered and concentrated to afford a white solid. The white solid was combined with product from other preparation using the same conditions to provide 1.1 g for purification. The white solid was slurried at reflux for 3 h in MTBE/n-Hep and then at rt for 5 days. The slurry was then filtered and the filter cake washed with n-heptane to afford Example 1 as a white solid (2.4 g, 73%). (MP=193.2-195.8° C.). The solid was then dissolved in refluxing EtOAc and hot-filtered. The filtrate was concentrated and recrystallized from ethyl acetate/n-heptane. The solid was collected by vacuum filtration and dried in a vacuum oven at 50° C. for 2 h to afford Example 1 as a white solid (1.4 g, 44%).
MP=189.9-196.8° C. MS (ES+): 397.1 (M+H). ¹H NMR (600 MHz, DMSO-d₆) δ: 12.10 (br. s, 1H), 6.22 (s, 1H), 5.63 (br. s, 1H), 4.54 (t, 1H), 4.20 (quin, 1H), 4.06 (br. s, 1H), 3.94-3.60 (m, 3H), 3.51 (br. s, 2H), 2.24 (d, 2H), 1.60 (br. d, 2H), 1.40 (d, 3H), 0.74 (br. s, 1H).

Example 2: [(1R,5S,6R)-3-{3-chloro-5-cyano-6-[(2S,3R)-3-hydroxy-2-methylazetidin-1-yl]-4-(trifluoromethyl)pyridin-2-yl}-3-azabicyclo[3.1.0]hex-6-yl]acetic acid

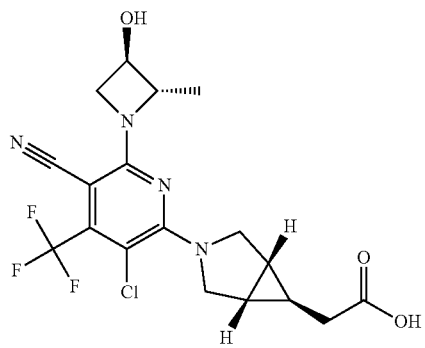 [SMILES: C[C@H]1[C@H](O)CN1c1nc(N2C[C@@H]3[C@@H](CC(=O)O)[C@@H]3C2)c(Cl)c(C(F)(F)F)c1C#N]

Step 1 ethyl [(1R,5S,6R)-3-{3-chloro-5-cyano-6-[(2S,3R)-3-hydroxy-2-methylazetidin-1-yl]-4-(trifluoromethyl)pyridin-2-yl}-3-azabicyclo[3.1.0]hex-6-yl]acetate Ethyl [(1R,5S,6R)-3-{5-cyano-6-[(2S,3R)-3-hydroxy-2-methylazetidin-1-yl]-4-(trifluoromethyl)pyridin-2-yl}-3-azabicyclo[3.1.0]hex-6-yl]acetate (60 mg, 0.14 mmol) in DMF (2.5 mL) was treated with N-chlorosuccinimide (28.3 mg, 0.212 mmol) at rt and the mixture was stirred for 16 h at 25° C. The mixture was diluted with water (15 mL) and saturated aqueous ammonium chloride (5 mL), then extracted with EtOAc (15 mL×3). The organic layer was washed with brine, dried over Na₂SO₄ and concentrated in vacuo to provide the title compound (80 mg, quant.) as an off-yellow solid, which was used to the next step directly.

Step 2

Example 2 was prepared in an analogous manner to Example 1, step 3, using ethyl [(1R,5S,6R)-3-{3-chloro-5-cyano-6-[(2S,3R)-3-hydroxy-2-methylazetidin-1-yl]-4-(trifluoromethyl)pyridin-2-yl}-3-azabicyclo[3.1.0]hex-6-yl]acetate and purified via preparative reverse phase HPLC to give the Example 2 (30 mg, 49%) as a white solid.
MS (ES+): 431.1 (M+H). ¹H NMR (400 MHz, CD₃OD) δ 4.70 (dd, 1H), 4.39-4.25 (m, 2H), 4.24-4.08 (m, 2H), 3.86-3.67 (m, 3H), 2.30 (d, 2H), 1.59 (br. s, 2H), 1.48 (d, 3H), 0.90-0.74 (m, 1H).

Example 3: Methyl [(1R,5S,6R)-3-{2-[(2S)-2-methylazetidin-1-yl]-6-(trifluoromethyl)pyrimidin-4-yl}-3-azabicyclo[3.1.0]hex-6-yl]acetate

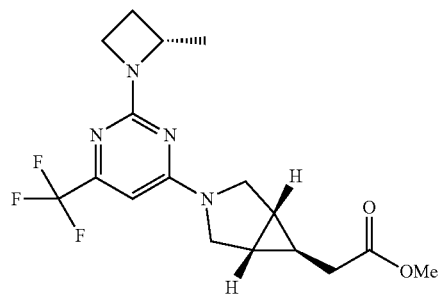 [SMILES: COC(=O)C[C@@H]1[C@H]2CN(c3cc(C(F)(F)F)nc(N4CC[C@@H]4C)n3)C[C@@H]12]

Step 1

Methyl {(1R,5S,6s)-3-[2-chloro-6-(trifluoromethyl)pyrimidin-4-yl]-3-azabicyclo[3.1.0]hex-6-yl}acetate To a solution of methyl (1R,5S,6S)-3-azabicyclo[3.1.0]hex-6-ylacetate hydrochloride (120.2 g, 627.2 mmol) in DCM (1250 mL) 2,4-dichloro-6-(trifluoromethyl)pyrimidine (145.7 g, 671.5 mmol) in DCM (50 ml) was added in drops at −72° C.; the addition funnel was washed with DCM (50 ml) and the wash was added into the reaction flask. DIPEA (273 mL, 1570 mmol) was added over 10 min with the reaction temperature maintained between −70° C. to −60° C. The mixture was stirred at −65° C. to −63° C. for 1 h and then warmed to 25° C. over 3 h. The resulting clear solution was concentrated to ~⅕ of the initial volume. To the obtained heavy slurry, MTBE (700 mL) and heptane (700 mL) were added and the resulting slurry was stirred at 25° C. for 10 min then solids were filtered off and washed with MTBE-heptane (4:1). The combined mother liquor was concentrated in vacuo to an oil, which was combined with heptane (1200 mL). The obtained heterogeneous mixture was stirred at 25° C. for 2.5 days. A white solid formed. The liquid was decanted and the solid was washed with heptane (200 mL) and dried in flow of nitrogen. The obtained title product was used for the next step without additional purification.

$^1$H NMR (400 MHz, CDCl$_3$) δ: 6.47 (s, 1H), 4.07 (d, 1H), 3.71 (s, 3H), 3.53-3.68 (m, 3H), 2.36-2.49 (m, 1H), 2.21-2.34 (m, 1H), 1.60-1.73 (m, 2H), 0.88-0.97 (m, 1H).

Step 2

Methyl {(1R,5S,6S)-3-[2-chloro-6-(trifluoromethyl)pyrimidin-4-yl]-3-azabicyclo[3.1.0]hex-6-yl}acetate from Step 1 was dissolved in acetonitrile (1500 mL) and (2S)-2-methylazetidinium [(1R,4S)-7,7-dimethyl-2-oxobicyclo[2.2.1]hept-1-yl]methanesulfonate (223.0 g, 735 mmol) was added. The mixture was stirred at 60° C. and DIPEA (77.0 mL, 442 mmol) was added during 3 h. The mixture was stirred for 3 h and then DIPEA (180 mL, 1.03 mol) was added over 3 h and the mixture was stirred at 60° C. for 18 h. Additional (2S)-2-methylazetidinium [(1R,4S)-7,7-dimethyl-2-oxobicyclo[2.2.1]hept-1-yl]methanesulfonate (18.0 g, 59 mmol) was added and the mixture was stirred at 60° C. for another 18 h. The mixture was concentrated to ~¼ of the initial volume and the resultant yellow oil was partitioned between 500 mL of water, 400 mL of heptane, and 400 mL of MTBE. The aqueous phase was separated and extracted again with MTBE-heptane (1:1) mixture (2×150 mL). The combined organic extract was washed with 120 mL of saturated NaHCO$_3$ (120 mL), and then stirred with SiO$_2$ (70 g) and anhydrous MgSO$_4$ (70 g). Solids were filtered off and the clear solution was concentrated to obtain 216.6 g Example 3 as a colorless oil.

MS (ES+): 371.1 (M+H). $^1$H NMR (400 MHz, CDCl$_3$) δ: 5.91 (s, 1H), 4.37-4.48 (m, 1H), 3.87-4.05 (m, 3H), 3.70 (s, 3H), 3.50-3.64 (m, 1H), 3.41-3.50 (m, 2H), 2.33-2.42 (m, 1H), 2.31 (d, 2H), 1.88-1.99 (m, 1H), 1.52-1.59 (m, 2H), 1.49 (d, 3H), 0.88-0.96 (m, 1H).

Example 4: [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid

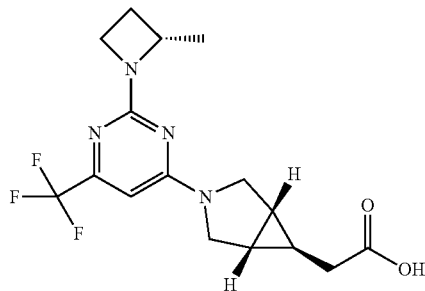 [SMILES: C[C@H]1CCN1c1nc(N2C[C@@H]3[C@@H](CC(=O)O)[C@@H]3C2)cc(C(F)(F)F)n1]

To a stirred solution of unpurified methyl [(1R,5S,6R)-3-{2-[(2S)-2-methylazetidin-1-yl]-6-(trifluoromethyl)pyrimidin-4-yl}-3-azabicyclo[3.1.0]hex-6-yl]acetate in methanol (650 mL) was added a solution of sodium hydroxide (35.1 g, 877 mmol) in water (70 mL) in small portions under stirring at 5° C. to 15° C. The mixture became clear in 30 min. The clear solution was stirred at RT for 3 h, then concentrated to ~⅓ of the initial volume and the residue was diluted with water (750 mL) and brine (250 mL), then washed with a mixture of MTBE (260 mL) and heptane (130 mL). The organic wash was discarded. The aqueous phase was washed with MTBE-heptane (2:1) mixture (2×300 mL) and the organic layers discarded. The aqueous layer was then combined with MTBE (250 mL) and heptane (250 mL) and cooled to 0° C. Slowly under stirring at 0° C. to 4° C., 6 M aq. HCl (130 mL) was added, followed by 1 M aq. KHSO$_4$ (150 mL), and the obtained mixture was stirred for 15 min. The organic phase was separated and the aqueous phase was additionally extracted with a mixture of MTBE (170 mL) and heptane (170 mL). The combined organic extract was washed with water-brine (1:1) mixture (150 mL), dried over anhydrous MgSO$_4$ (60 g) and SiO$_2$ (60 g), filtered, and concentrated to give a colorless oil. It was combined (as a concentrated solution in MTBE) with another batch, which was prepared using identical conditions on the same scale. The combined MTBE solution was concentrated in vacuo, then heptane (2000 mL) was added and the suspension was concentrated again, with gradual increase of vacuum to obtain the desired product (406.0 g). A portion of this material (196 g) was dissolved in MTBE (220 mL) at 60° C. to 63° C., stirred slowly, and heptane (1500 mL) was added at 55° C. to 60° C. The mixture was seeded with crystalline title compound (50 mg). The mixture was stirred at 60° C. for 30 min, then additional heptane (1700 mL) was added during 20 min. The heterogeneous mixture was stirred at 60° C. for 2 h and then slowly cooled to 25° C. and stirred for 20 h. A small amount of solid was stuck on the flask walls and easily moved into the liquid phase with a spatula and the mixture was further stirred at 25° C. for 24 h. The solids were filtered off, washed with 5% MTBE in heptane, and dried in vacuo at 50° C. for 48 h to obtain Example 4 as a white crystalline solid (178.2 g, 73% over 3 steps). Crystalline solid of Example 4 has also been obtained using similar purification conditions without seeding.

MP: 122-123° C., [α]$_D$+86.3° (CDCl$_3$, c=1.37). MS (ES+): 357.3 (M+H). $^1$H NMR (400 MHz, CDCl$_3$) δ: 10.84 (br. s, 1H), 5.92 (s, 1H), 4.38-4.51 (m, 1H), 3.89-4.10 (m, 3H), 3.53-3.66 (m, 1H), 3.41-3.53 (m, 2H), 2.30-2.46 (m, 3H), 1.94 (ddt, 1H), 1.55-1.63 (m, 2H), 1.50 (d, 3H), 0.94 (m, 1H).

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength Kα$_1$=1.54056 Å from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software.

PXRD data file was not processed prior to peak searching. Using the peak search algorithm in the EVA software, peaks were selected with a threshold value of 1 and a width value of 0.3 were used to make preliminary peak assignments. The output of automated assignments was visually checked to ensure validity and adjustments manually made if necessary.

Peaks with relative intensity of 3% were generally chosen. The peaks which were not resolved or were consistent with noise were also discarded. A typical error associated with the peak position from PXRD stated in USP and JP is up to +1-0.2°.

Characteristic peaks for crystalline free acid of Example 4 include Angle 2Θ (°) values of about 9.0, 10.4, 15.0, and 21.4+/−0.2°. Yet another embodiment of the crystalline free acid of Example 4 is where characteristic peaks include Angle 2Θ (°) values of about 9.0, 15.0 19.6, 21.4, and 26.5+/−0.2°. Yet another embodiment of the crystalline free acid of Example 4 is where characteristic peaks include Angle 2Θ (°) values of about 9.0, 10.4, 11.5, 15.0, 16.5, 19.6, 21.4, and 26.5+/−0.2°. Yet another embodiment of the crystalline free acid of Example 4 is where characteristic peaks include Angle 2Θ (°) values of about 10.4, 11.5, 15.0, 19.6, and 26.5+/−0.2°. Table 1 provides PXRD peak list for crystalline free acid of Example 4, +/−0.2° is to apply to said peaks. FIG. 1 provides the PXRD pattern of crystalline free acid of Example 4.

TABLE 1

| PXRD peak list for crystalline free acid of Example 4 | |
|---|---|
| Angle 2Θ (°)* | Intensity (%) |
| 9.0 | 37 |
| 10.4 | 17 |
| 11.5 | 16 |
| 13.5 | 10 |
| 13.9 | 5 |
| 15.0 | 45 |
| 16.5 | 23 |
| 17.3 | 4 |
| 17.7 | 14 |
| 18.1 | 40 |
| 18.3 | 85 |
| 18.8 | 17 |
| 18.9 | 7 |
| 19.6 | 100 |
| 21.4 | 36 |
| 22.8 | 22 |
| 22.9 | 15 |
| 23.3 | 55 |
| 23.7 | 6 |
| 25.7 | 7 |
| 25.9 | 20 |
| 26.5 | 30 |
| 27.1 | 9 |
| 27.6 | 5 |
| 28.1 | 9 |
| 29.1 | 6 |
| 30.1 | 10 |
| 30.5 | 6 |
| 31.6 | 4 |

Example 5: [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetic acid

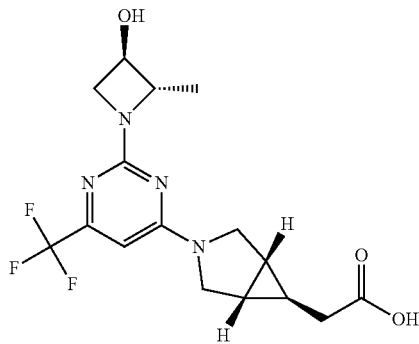 [SMILES: C[C@H]1[C@H](O)CN1c1nc(N2C[C@@H]3[C@@H](CC(=O)O)[C@@H]3C2)cc(C(F)(F)F)n1]

Step 1: methyl [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetate A solution of methyl {(1R,5S,6S)-3-[2-chloro-6-(trifluoromethyl)pyrimidin-4-yl]-3-azabicyclo[3.1.0]hex-6-yl}acetate (1.55 g, 4.60 mmol), (2S,3R)-3-hydroxy-2-methylazetidin-1-ium [(1R,4S)-7,7-dimethyl-2-oxobicyclo[2.2.1]hept-1-yl]methanesulfonate (1.62 g, 5.10 mmol), triethylamine (1.6 mL, 12.0 mmol) and acetonitrile (15.4 mL) was heated at 60° C. for 16 h. The reaction was cooled to rt and concentrated. Water (15 mL) was added and the reaction was extracted with EtOAc (10 mL×3). The combined organic layers were concentrated and purified by flash chromatography (EtOAc/heptane, 0% to 100%) on a silica gel column to give the title compound (1.3 g, 73%) as a white solid.

$^1$H NMR (400 MHz, CDCl$_3$) δ: 5.98 (s, 1H), 4.31 (ddd, 1H), 4.23 (t, 1H), 4.21-4.11 (m, 1H), 4.09-3.89 (m, 1H), 3.76 (dd, 1H), 3.72 (s, 3H), 3.67-3.54 (m, 1H), 3.53-3.41 (m, 2H), 2.34 (d, 2H), 1.61-1.58 (m, 2H), 1.54 (d, 3H), 0.98-0.88 (m, 1H).

Step 2

To a solution of methyl [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetate (1.30 g, 3.36 mmol) in methanol (5 mL) was added 2M aqueous NaOH (4.2 mL, 8.4 mmol). After 3 h at rt, the reaction is quenched with 1M aqueous potassium hydrogen sulfate (10 mL), extracted with t-butyl methyl ether (10 mL×3) and concentrated to yield Example 5 (1.2 g, 96%). A crystalline sodium salt form was made by mixing Example 5 (500 mg, 1.34 mmol) with 1M NaOH (1.34 mL, 1.34 mmol). The solution was stirred at rt for 5 minutes then dried under reduced pressure to yield a white solid. EtOAc (3 mL), heptane (0.5 mL) and water (0.1 mL) were added and the suspension was stirred at rt for 16 h. The resulting white solid was isolated and dried to yield Example 5 as the crystalline sodium salt.

MS (AP+): 373.4 (M+H). $^1$H NMR (400 MHz, CDCl$_3$) δ: 5.96 (s, 1H), 4.34-4.25 (m, 1H), 4.25-4.17 (m, 1H), 4.17-4.10 (m, 1H), 4.06-3.88 (m, 1H), 3.74 (dd, 1H), 3.65-3.53 (s, 1H), 3.53-3.43 (m, 2H), 2.45-2.27 (m, 2H), 1.62-1.55 (m, 2H), 1.52 (d, 3H), 0.97-0.87 (m, 1H).

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength $K\alpha_1=1.54056$ Å from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software.

PXRD data file was not processed prior to peak searching. Using the peak search algorithm in the EVA software, peaks were selected with a threshold value of 1 and a width value of 0.3 were used to make preliminary peak assignments. The output of automated assignments was visually checked to ensure validity and adjustments manually made if necessary. Peaks with relative intensity of 3% were generally chosen. The peaks which were not resolved or were consistent with noise were also discarded. A typical error associated with the peak position from PXRD stated in USP and JP is up to +1-0.2°.

Figure 2:
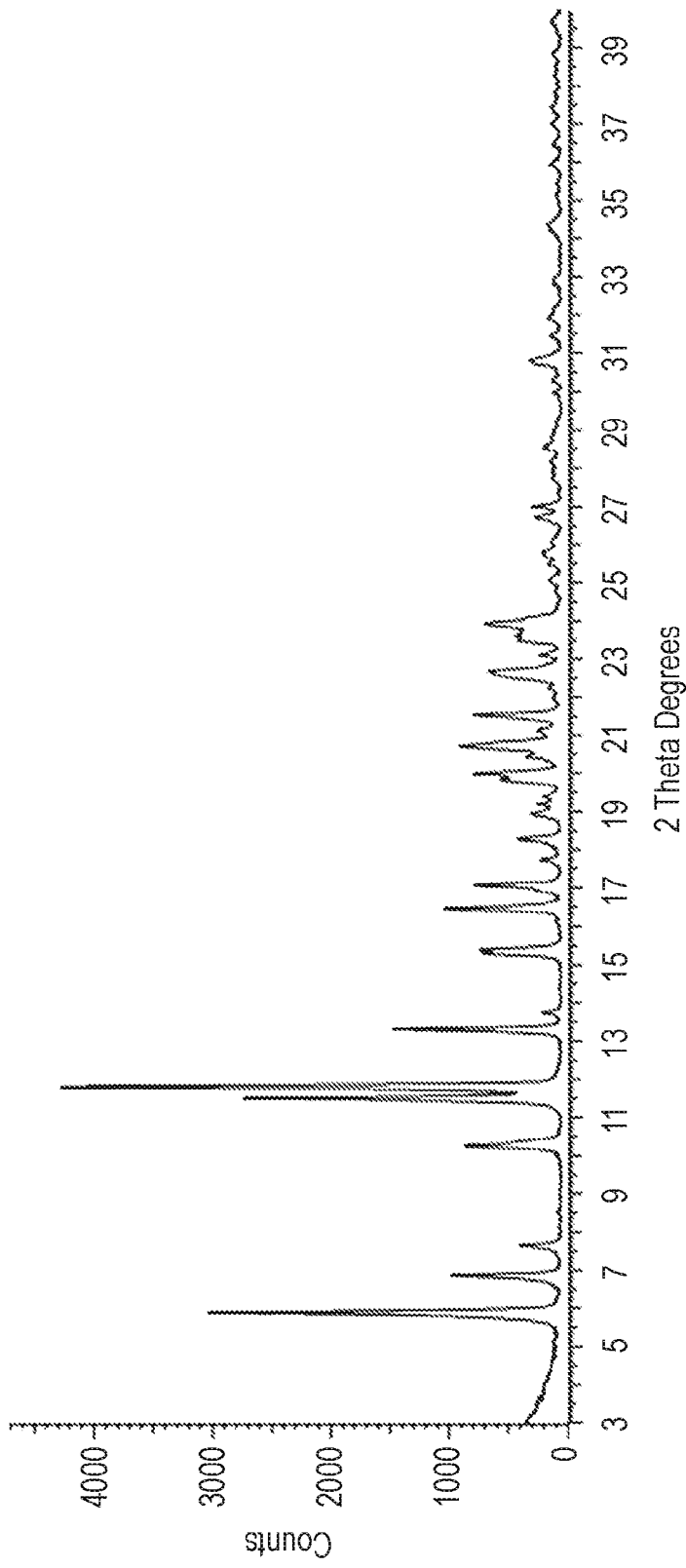
FIG. 2 provides the PXRD pattern of crystalline sodium salt of Example 5.

Characteristic peaks for crystalline sodium salt of Example 5 include Angle 2Θ (°) values of about 5.9, 11.5, 11.8, 13.3, 21.5+/−0.2°. Yet another embodiment of the crystalline sodium salt of Example 5 is where characteristic peaks include Angle 2Θ (°) values of about 5.9, 10.3, 11.5, 11.8, 13.3, 16.5, 21.5, ad 22.6+/−0.2°. Yet another embodiment of the crystalline sodium salt of Example 5 is where characteristic peaks include Angle 2Θ (°) values of about 5.9, 10.3, 11.8, 16.5, and 21.5+/−0.2°. Table 2 provides PXRD peak list for crystalline sodium salt of Example 5, +/−0.2° is to apply to said peaks. FIG. 2 provides the PXRD pattern of crystalline sodium salt of Example 5.

TABLE 2

PXRD peak list for crystalline sodium salt of Example 5

| Angle 2Θ (°)* | Intensity (%) |
|---|---|
| 5.9 | 81 |
| 6.8 | 27 |
| 7.6 | 11 |
| 10.3 | 26 |
| 11.5 | 92 |
| 11.8 | 100 |
| 13.3 | 48 |
| 13.7 | 5 |
| 15.3 | 20 |
| 16.5 | 33 |
| 17.0 | 22 |
| 17.7 | 6 |
| 18.3 | 11 |
| 19.0 | 5 |
| 19.2 | 4 |
| 19.9 | 15 |
| 20.4 | 7 |
| 20.7 | 28 |
| 21.1 | 4 |
| 21.5 | 21 |
| 22.6 | 18 |
| 23.1 | 4 |
| 23.7 | 11 |
| 23.9 | 20 |
| 25.0 | 3 |
| 25.8 | 4 |
| 26.7 | 6 |
| 27.0 | 8 |

TABLE 2-continued

PXRD peak list for crystalline sodium salt of Example 5

| Angle 2Θ (°)* | Intensity (%) |
|---|---|
| 28.6 | 3 |
| 30.8 | 8 |
| 31.5 | 3 |
| 34.3 | 3 |
| 36.0 | 3 |

Example 6: {(1R,5S,6s)-3-[2-cyclobutyl-6-(trifluoromethyl)pyrimidin-4-yl]-3-azabicyclo[3.1.0]hex-6-yl}acetic acid

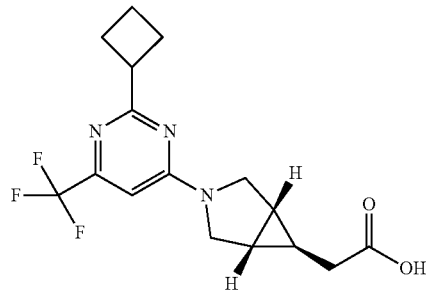 [SMILES: O=C(O)C[C@@H]1[C@H]2CN(c3cc(C(F)(F)F)nc(C4CCC4)n3)C[C@@H]12]

Step 1: Ethyl {(1R,5S,6S)-3-[2-cyclobutyl-6-(trifluoromethyl)pyrimidin-4-yl]-3-azabicyclo[3.1.0]hex-6-yl}acetate To a solution of ethyl {(1R,5S,6S)-3-[2-chloro-6-(trifluoromethyl)pyrimidin-4-yl]-3-azabicyclo[3.1.0]hex-6-yl}acetate (50 mg, 0.14 mmol; prepared in an analogous manner to the compound obtained in Step 1 of Example 3) in dry DMF (3 mL) was added $(tBu_3P)_2Pd$ (7.3 mg, 0.014 mmol). The mixture was purged with nitrogen and 0.5 M solution of cyclobutylzinc bromide in THF (0.86 mL, 0.43 mmol) was added. The resulting grey suspension was flushed with nitrogen and then stirred in a capped vial at 100° C. for 1 h. The mixture was poured into saturated aqueous $NH_4Cl$ (15 mL) and extracted with EtOAc (3×15 mL). The combined organic extract was washed with brine, dried over $Na_2SO_4$, and concentrated. The residue was purified by preparative TLC, eluting with a mixture EtOAc-petroleum ether (1:5) to obtain the title compound as a colorless gum (45 mg, 85% yield).

MS (ES+): 369.9 (M+H).

Step 2

Example 6 was synthesized in an analogous manner to Example 1, Step 3, using ethyl {(1R,5S,6S)-3-[2-cyclobutyl-6-(trifluoromethyl)pyrimidin-4-yl]-3-azabicyclo[3.1.0]hex-6-yl}acetate, and purified by reverse phase preparative HPLC to provide 15 mg (36% yield) as a white solid.

MS (ES+): 342.1 (M+H). $^1$H NMR (400 MHz, $CD_3OD$) δ: 6.57 (s, 1H), 4.04-4.18 (m, 1H), 3.46-3.76 (m, 4H), 2.20-2.50 (m, 6H), 1.98-2.14 (m, 1H), 1.85-1.96 (m, 1H), 1.57-1.76 (m, 2H), 0.79-0.94 (m, 1H).

Example 7: [(1R,5S,6R)-3-{5-cyclopropyl-2-[(2S,3R)-3-hydroxy-2-methylazetidin-1-yl]-6-(trifluoromethyl)pyrimidin-4-yl}-3-azabicyclo[3.1.0]hex-6-yl]acetic acid

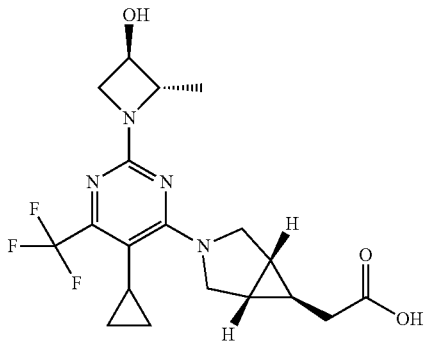 [SMILES: C[C@H]1[C@H](O)CN1c1nc(N2C[C@@H]3[C@@H](CC(=O)O)[C@@H]3C2)c(C2CC2)c(C(F)(F)F)n1]

Step 1: Ethyl [(1R,5S,6R)-3-{5-cyclopropyl-2-[(2S,3R)-3-hydroxy-2-methylazetidin-1-yl]-6-(trifluoromethyl)pyrimidin-4-yl}-3-azabicyclo[3.1.0]hex-6-yl]acetate To a mixture of ethyl [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetate (100 mg, 0.250 mmol; synthesized in an analogous manner to the compound obtained in Step 1 of Example 5), was added potassium cyclopropyltrifluoroborate (185 mg, 1.25 mmol), AgNO$_3$ (8.5 mg, 0.050 mmol), K$_2$S$_2$O$_8$ (338 mg, 1.25 mmol), DCE (5.0 mL) and water (5.0 mL). TFA (57 mg, 0.50 mmol) was then added. The reaction vial was capped and the reaction mixture was stirred at 50° C. for 16 h. The reaction mixture was diluted with aq. ammonium chloride (10 mL), extracted with EtOAc (3×30 mL). The combined organic layers were washed with brine, dried over with Na$_2$SO$_4$, and concentrated to give the crude product as yellow oil, which was purified by preparative TLC with 10% MeOH in DCM to give the title compound (30 mg, 27%) as colorless oil.

MS (ES+): 441.1 (M+H).

Step 2

Example 7 was synthesized in an analogous manner to Example 1, Step 3, using ethyl [(1R,5S,6R)-3-{5-cyclopropyl-2-[(2S,3R)-3-hydroxy-2-methylazetidin-1-yl]-6-(trifluoromethyl)pyrimidin-4-yl}-3-azabicyclo[3.1.0]hex-6-yl]acetate, and purified by reverse phase preparative HPLC to provide 10 mg (36% yield) as a white solid.

MS (ES+): 413.1 (M+H). $^1$H NMR (400 MHz, CD$_3$OD) δ: 4.30-4.19 (m, 3H), 4.15-4.07 (m, 2H), 3.70-3.56 (m, 3H), 2.31 (d, 2H), 1.90-1.81 (m, 1H), 1.58-1.53 (m, 2H), 1.47 (d, 3H), 1.02-0.95 (m, 2H), 0.93-0.84 (m, 1H), 0.49-0.41 (m, 2H).

Example 8: [(1R,5S,6R)-3-{5-ethyl-2-[(2S,3R)-3-hydroxy-2-methylazetidin-1-yl]-6-(trifluoromethyl)pyrimidin-4-yl}-3-azabicyclo[3.1.0]hex-6-yl]acetic acid

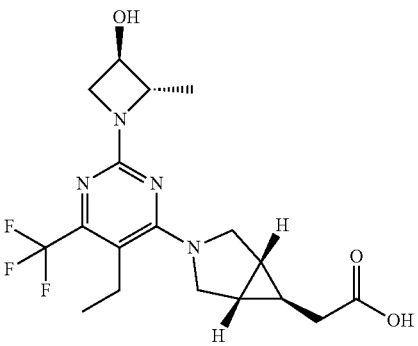 [SMILES: CCc1c(N2C[C@@H]3[C@@H](CC(=O)O)[C@@H]3C2)nc(N2C[C@@H](O)[C@@H]2C)nc1C(F)(F)F]

Step 1: ethyl [(1R,5S,6R)-3-{5-bromo-2-[(2S,3R)-3-hydroxy-2-methylazetidin-1-yl]-6-(trifluoromethyl)pyrimidin-4-yl}-3-azabicyclo[3.1.0]hex-6-yl]acetate To a 0° C. solution of ethyl [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetate (100 mg, 0.259 mmol; made in analogous manner to methyl [(1R,5S,6R)-3-{2-[(2S,3R)-3-hydroxy-2-methylazetidin-1-yl]-6-(trifluoromethyl)pyrimidin-4-yl}-3-azabicyclo[3.1.0]hex-6-yl]acetate) in dry acetonitrile (10 mL) was added N-bromosuccinimide (60 mg, 0.29 mmol, 85% purity) and the reaction was stirred for 1 h at 0° C. The mixture was diluted with aqueous sodium bicarbonate, extracted with EtOAc (30 mL×3) and the combined organic layers were washed with brine, dried over with Na$_2$SO$_4$, filtered and concentrated to give the crude material which was purified by silica gel chromatography (EtOAc in petroleum ether, 0% to 40%) to give the title compound (110 mg, 91% yield) as light yellow solid.

Step 2: ethyl [(1R,5S,6R)-3-{5-ethenyl-2-[(2S,3R)-3-hydroxy-2-methylazetidin-1-yl]-6-(trifluoromethyl)pyrimidin-4-yl}-3-azabicyclo[3.1.0]hex-6-yl]acetate To a mixture of ethyl [(1R,5S,6R)-3-{5-bromo-2-[(2S,3R)-3-hydroxy-2-methylazetidin-1-yl]-6-(trifluoromethyl)pyrimidin-4-yl}-3-azabicyclo[3.1.0]hex-6-yl]acetate (50 mg, 0.11 mmol), tributylvinyl tin (51 mg, 0.16 mmol) and Pd(PPh$_3$)$_2$Cl$_2$ (11 mg, 0.015 mmol) in dry dioxane (5.0 mL) was added tetrabutylammonium bromide (35 mg, 0.11 mmol). The red reaction mixture was stirred at 50° C. for 16 h. The black reaction mixture was diluted with aq. NH$_4$Cl, extracted with EtOAc (20 mL) three times. The combined organic layer was washed with brine, dried over with Na$_2$SO$_4$, filtered and the filtrate was concentrated to give the crude product as red oil. The residue was purified by Prep-TLC (Petroleum ether:EtOAc=1:1) to give the crude product, and re-purified under the same condition by preparative TLC (Petroleum ether:EtOAc=1:1) to obtain the title compound as a white solid (15 mg). MS (ES+): 427.1 (M+H).

Step 3: ethyl [(1R,5S,6R)-3-{5-ethenyl-2-[(2S,3R)-3-hydroxy-2-methylazetidin-1-yl]-6-(trifluoromethyl)pyrimidin-4-yl}-3-azabicyclo[3.1.0]hex-6-yl]acetate To a mixture of ethyl [(1R,5S,6R)-3-{5-ethenyl-2-[(2S,3R)-3-hydroxy-2-methylazetidin-1-yl]-6-(trifluoromethyl)pyrimidin-4-yl}-3-azabicyclo[3.1.0]hex-6-yl]acetate (50 mg, 0.020 mmol, 17% purity) in dry ethanol (10.0 mL) was added Pd/C (2.1 mg, 0.0020 mmol). The black suspension was stirred at 25° C. for 16.0 hours under a hydrogen atmosphere (30 Psi). The catalyst was filtered and the filtrate was concentrated to give the desired product 35 mg, as white solid.

Step 4

Example 8 was synthesized in an analogous manner to Example 1, Step 3 using ethyl [(1R,5S,6R)-3-{5-ethenyl-2-[(2S,3R)-3-hydroxy-2-methylazetidin-1-yl]-6-(trifluoromethyl)pyrimidin-4-yl}-3-azabicyclo[3.1.0]hex-6-yl]acetate and purified via preparative reverse phase chromatography to provide 6 mg as a white solid.

MS (ES+): 401.0 (M+H). $^1$H NMR (400 MHz, CD$_3$OD) δ 4.22 (dd, 1H), 4.16-4.08 (m, 2H), 4.03 (t, 2H), 3.75-3.64 (m, 2H), 3.45-3.48 (m, 1H), 2.73 (q, 2H), 2.36-2.29 (d, 2H), 1.63-1.59 (br. m 2H), 1.49 (d, 3H), 1.03 (t, 3H), 0.91-0.83 (m, 1H).

Example 9: (2S,3R)-2,3-dimethyl-1-[4-{(1R,5S,6S)-6-[(methylsulfonyl)methyl]-3-azabicyclo[3.1.0]hex-3-yl}-6-(trifluoromethyl)pyrimidin-2-yl]azetidin-3-ol

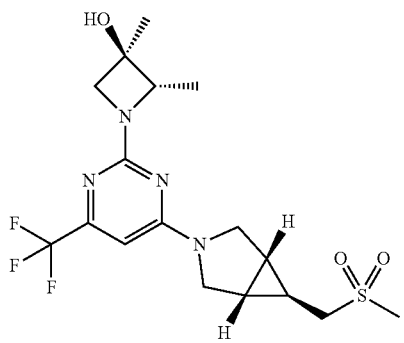 [SMILES: C[C@@H]1N(c2nc(N3C[C@@H]4[C@H](C3)[C@H]4CS(C)(=O)=O)cc(C(F)(F)F)n2)C[C@@]1(C)O]

Step 1: (1R,5S,6r)-3-benzyl-6-(iodomethyl)-3-azabicyclo[3.1.0]hexane

[(1R,5S,6r)-3-benzyl-3-azabicyclo[3.1.0]hex-6-yl]methyl methanesulfonate (600 mg, 2.13 mmol) and NaI (639, 4.26 mmol) was suspended in MeCN (5 mL) and stirred for 16 h. The white suspension was diluted with NH$_4$Cl (20 mL) and extracted with EtOAc (30 ml×3). The combined organics were concentrated to yield a red oil which was purified by flash chromatography (Petroleum ether/EtOAc 0 to 40%) on a silica gel column to isolate the title compound (500 mg, 75%) as a yellow oil.

$^1$H NMR (400 MHz, CDCl$_3$) δ 7.36-7.18 (m, 5H), 3.57 (s, 2H), 3.12 (d, 2H), 2.98 (d, 2H), 2.37-2.24 (m, 2H), 1.87-1.76 (m, 1H), 1.36-1.29 (m, 2H)

Step 2: (1R,5S,6r)-3-benzyl-6-[(methylsulfonyl)methyl]-3-azabicyclo[3.1.0]hexane (1R,5S,6r)-3-Benzyl-6-(iodomethyl)-3-azabicyclo[3.1.0]hexane (500 mg, 1.60 mmol) was dissolved in EtOH (10 mL). Sodium methanesulfinate (489 mg, 4.79 mmol) was added portionwise. The yellow solution was stirred at 80° C. for 16 h, then at rt for 48 h. The reaction was diluted with water (50 ml) and extracted with EtOAc (30 ml×3). The combined organics were concentrated to yield a colorless oil which was purified by flash chromatography (Petroleum ether/EtOAc 50 to 80%) on a silica gel column to isolate the title compound (310 mg, 73%) as a yellow solid.

$^1$H NMR (400 MHz, CDCl$_3$) δ 7.41-7.10 (m, 5H), 3.59 (s, 2H), 3.04 (d, 2H), 2.96-2.86 (m, 5H), 2.44-2.33 (m, 2H), 1.75-1.65 (m, 1H), 1.53-1.41 (m, 2H).

Step 3: (1R,5S,6r)-6-[(methylsulfonyl)methyl]-3-azabicyclo[3.1.0]hexane (1R,5S,6r)-3-Benzyl-6-[(methylsulfonyl)methyl]-3-azabicyclo[3.1.0]hexane (310 mg, 1.17 mmol) was dissolved in EtOH (10 mL) and 10 wt % Pd/C (249 mg, 0.234 mmol) was added. The suspension was stirred under 50 psi of H$_2$ for 48 h. The reaction was filtered and the filtrate was concentrated to yield a white solid (200 mg, 98%) and used directly in the next step without purification.

Step 4

Example 9 was made analogously to Example 1, Steps 1-2 starting from (1R,5S,6r)-6-[(methylsulfonyl)methyl]-3-azabicyclo[3.1.0]hexane (40 mg, 0.11 mmol). Upon completion, the reaction was quenched with sat. aq. NH$_4$Cl and extracted with EtOAc. The organics were concentrated and purified by preparatory HPLC (Phenomenex Gemini C18 250*50 10 μm 26% MeCN in water (0.225% Formic Acid) to 46% MeCN in water (0.225% Formic Acid)) to isolate Example 9 (30 mg, 25% yield over two steps) as a white solid.

MS (ES+): 420.9 (M+H). $^1$H NMR (400 MHz, CD$_3$OD) δ 6.13 (s, 1H), 4.16 (q, 1H), 4.09-3.87 (m, 1H), 3.87-3.75 (m, 2H), 3.75-3.62 (m, 1H), 3.61-3.46 (m, 2H), 3.16 (d, 2H), 2.99 (s, 3H), 1.87 (s, 2H), 1.42 (d, 3H), 1.39 (s, 3H), 0.98 (tt, 1H)

Example 10: 2-[(1R,5S,6R)-3-{2-[(2S)-2-methylazetidin-1-yl]-6-(trifluoromethyl)pyrimidin-4-yl}-3-azabicyclo[3.1.0]hex-6-yl]-N-(methylsulfonyl)acetamide

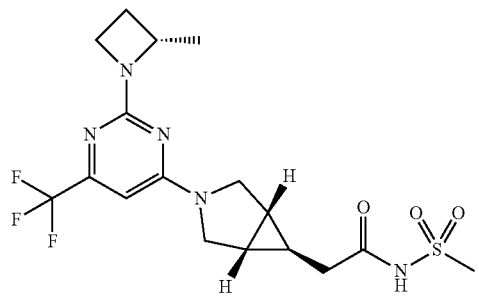 [SMILES: C[C@H]1CCN1c1nc(N2C[C@@H]3[C@@H](CC(=O)NS(C)(=O)=O)[C@@H]3C2)cc(C(F)(F)F)n1]

[(1R,5S,6R)-3-{2-[(2S)-2-Methylazetidin-1-yl]-6-(trifluoromethyl)pyrimidin-4-yl}-3-azabicyclo[3.1.0]hex-6-yl]

acetic acid (75 mg, 0.21 mmol) was dissolved in DCM (6 mL). Carbonyldiimidazole (34 mg, 0.21 mmol) was added. After 2 h, methanesulfonamide (22 mg, 0.23 mmol) and 1,8-Diazabicycloundec-7-ene (38 mg, 0.25 mmol) were added. After stirring for 16 h, the reaction was diluted with NH$_4$Cl solution (15 mL) and extracted with DCM (15 ml×3). The combined organics were concentrated and the crude material was purified by preparatory HPLC (Agela Durashell C18 150*25 5u Mobile phase: from 43% MeCN in water (0.225% formic acid) to 63% MeCN in water (0.225% FA) to isolate Example 10 as a white solid (32 mg, 35%).

MS (ES+): 434.0 (M+H). $^1$H NMR (400 MHz, CD$_3$OD) δ 6.05 (s, 1H), 4.50-4.35 (m, 1H), 4.04-3.83 (m, 3H), 3.71-3.40 (m, 3H), 3.24 (s, 3H), 2.45-2.36 (m, 1H), 2.34 (d, 2H), 2.00-1.86 (m, 1H), 1.69-1.57 (m, 2H), 1.48 (d, 3H), 0.90-0.79 (m, 1H).

Example 11: (1R,5S,6R)-3-{2-[(2S)-2-methylazetidin-1-yl]-6-(trifluoromethyl)pyrimidin-4-yl}-6-(1H-tetrazol-5-ylmethyl)-3-azabicyclo[3.1.0]hexane

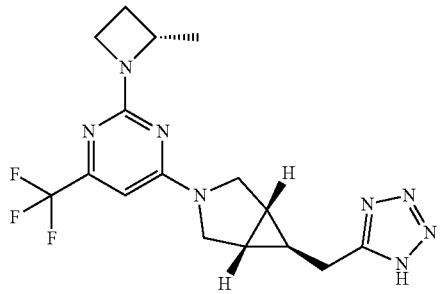 [SMILES: C[C@H]1CCN1c1nc(N2C[C@@H]3[C@@H](Cc4nnn[nH]4)[C@@H]3C2)cc(C(F)(F)F)n1]

Step 1: tert-butyl (1R,5S,6s)-6-(1H-tetrazol-5-ylmethyl)-3-azabicyclo[3.1.0]hexane-3-carboxylate tert-Butyl (1R,5S,6S)-6-(cyanomethyl)-3-azabicyclo[3.1.0]hexane-3-carboxylate (50 mg, 0.22 mmol) was dissolved in toluene (2 mL) and tributyltin azide (224 mg, 0.675 mmol) was added. The reaction was refluxed for 16 h then cooled to rt. The reaction was diluted with saturated aq. Na$_2$CO$_3$ (5 mL) and water (5 mL) and washed with DCM (15 mL×2). The aq. layer was then acidified to pH=5 and extracted with 10:1 CH$_2$Cl$_2$:MeOH (15 mL×3). The combined organics were concentrated to yield the title compound (50 mg, 84%) as a colorless oil. This compound was used without further purification.

$^1$H NMR (400 MHz, CDCl$_3$) δ 3.60-3.48 (m, 2H), 3.46-3.29 (m, 2H), 3.08 (dd, 1H), 2.90 (dd, 1H), 1.65-1.50 (m, 2H), 1.43 (s, 9H), 1.13-1.02 (m, 1H).

Step 2: (1R,5S,6s)-6-(1H-tetrazol-5-ylmethyl)-3-azabicyclo[3.1.0]hexane trifluoroacetic acid salt tert-Butyl (1R,5S,6S)-6-(1H-tetrazol-5-ylmethyl)-3-azabicyclo[3.1.0]hexane-3-carboxylate (45 mg, 0.10 mmol) was dissolved in DCM (3 mL) and TFA (1.5 mL) was added. After 2 h at rt, the reaction was concentrated to dryness to give the title compound which used without further purification.

Step 3

Example 11 was made analogously to Example 1, Steps 1 to 2 from (1R,5S,6s)-6-(1H-tetrazol-5-ylmethyl)-3-azabicyclo[3.1.0]hexane (trifluoroacetate salt, 70 mg, 0.12 mmol). Upon completion, the reaction was quenched with sat. aq. NH$_4$Cl (20 mL), acidified to pH=5, and extracted with EtOAc (20 mL×3). The organics were concentrated and purified by preparatory HPLC (Daiso 150*25 5 μm, 36% MeCN in water (0.225% Formic Acid) to 66% MeCN in water (0.225% Formic Acid)) to isolate Example 11 (9 mg, 19%) as a white solid.

MS (ES+): 381.0 (M+H). $^1$H NMR (400 MHz, CD$_3$OD) δ 6.07 (s, 1H), 4.50-4.35 (m, 1H), 4.09-3.84 (m, 3H), 3.72-3.56 (m, 1H), 3.56-3.44 (m, 2H), 3.00 (d, 2H), 2.46-2.34 (m, 1H), 2.02-1.86 (m, 1H), 1.82-1.67 (m, 2H), 1.49 (d, 3H), 1.04-0.94 (m, 1H).

Example 12: [(1R,5S,6R)-3-{3-chloro-2-(1,1-difluoroethyl)-6-[(2S,3R)-3-hydroxy-2-methylazetidin-1-yl]pyridin-4-yl}-3-azabicyclo[3.1.0]hex-6-yl]acetic acid

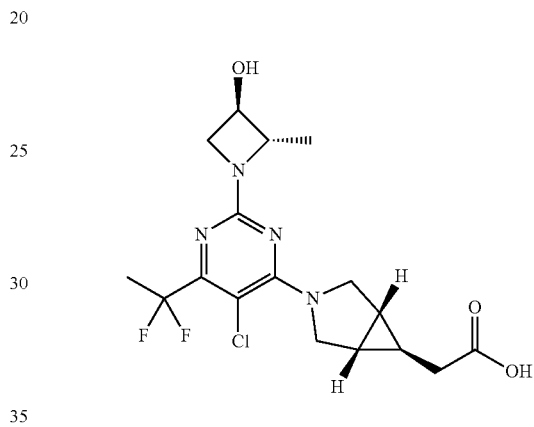

Step 1: ethyl-3-amino-4,4-difluoropent-2-enoate

In two separate batches, a solution of EtOAc (6.0 g, 70 mmol) in THF (50 mL) was added sodium hydride (60% in mineral oil, 2.72 g, 68.1 mmol) in portions. After the addition was complete, ethyl 2,2-difluoropropanoate (11.3 g, 81.7 mmol) was added over 15 min in a dropwise manner. The reaction mixture was heated at 50° C. for 4 h, then stirred at rt for 16 h. The reaction mixture was poured into 10% sulfuric acid (50 mL) and extracted with EtOAc (2×50 mL). The combined organics were dried over Na$_2$SO$_4$, filtered and concentrated. The crude products were combined and purified using column chromatography eluting with EtOAc/petroleum ether (1:5) to give a yellow oil. The product was dissolved in ethanol (150 mL) and treated with ammonium acetate (42.8 g, 555 mmol). The mixture was heated at 80° C. for 16 h. The solvent was removed under reduced pressure and the residue was diluted with aqueous NaHCO$_3$ (100 mL) and extracted with DCM (2×100 mL). The combined organic phases were dried over Na$_2$SO$_4$, filtered and concentrated to give the title compound (22.5 g, 90.5%) as a brown oil.

$^1$H NMR (400 MHz, CDCl$_3$) δ: 4.89 (s, 1H), 4.16 (q, 2H), 1.81 (t, 3H), 1.28 (t, 3H).

Step 2: ethyl-3-[(3-ethoxy-3-oxopropanoyl)amino]-4,4-difluoropent-2-enoate

To a solution of ethyl-3-amino-4,4-difluoropent-2-enoate (22.5 g, 126 mmol) and pyridine (11.9 g, 151 mmol) in DCM (250 mL) was added ethyl 3-chloro-3-oxopropanoate (18.9 g, 126 mmol) dropwise at 0° C. The solution was stirred at rt for 16 h. The reaction mixture was washed with 1N HCl (250 mL) and saturated aqueous NaHCO$_3$ (250 mL), dried over Na$_2$SO$_4$, filtered and concentrated. The crude product was purified using column chromatography eluting with EtOAc/petroleum ether (1:10) to give the title compound (18.9 g, 51.3% yield) as light yellow oil.

$^1$H NMR (400 MHz, CDCl$_3$) δ: 10.53 (br. s, 1H), 5.77 (s, 1H), 4.18-4.28 (m, 4H), 3.45 (s, 2H), 1.99 (t, 3H), 1.23-1.39 (m, 6H).

Step 3: ethyl 6-(1,1-difluoroethyl)-2,4-dihydroxy-pyridine-3-carboxylate

A suspension of ethyl-3-[(3-ethoxy-3-oxopropanoyl) amino]-4,4-difluoropent-2-enoate (18.9 g, 64.4 mmol) and potassium tert-butoxide (8.68 g, 77.3 mmol) in EtOH (100 mL) was stirred at 80° C. for 4 h followed by 10° C. for 16 h. The solvent was removed under reduced pressure, and the residue was poured into ice-water (150 mL). The resulting solution was acidified to pH=2 with aqueous 2N HCl. The product was extracted with EtOAc (2×200 mL). The combined organic layers were filtered, and the white cake (13.0 g) was collected. The filtrate was concentrated to dryness and washed with MeOH to give additional white solids (1.5 g), which were combined with the filtered solids to give the title compound (14.5 g, 91% yield) as a white solid.

$^1$H NMR (400 MHz, DMSO-d$_6$) δ: 11.82 (br. s, 2H), 6.30 (s, 1H), 4.23 (q, 2H), 1.92 (t, 3H), 1.28 (t, 3H).

Step 4: ethyl 6-(1,1-difluoroethyl)-2,4-diethoxypyridine-3-carboxylate

To a mixture of ethyl 6-(1,1-difluoroethyl)-2,4-dihydropyridine-3-carboxylate (2.00 g, 8.09 mmol) and solid potassium carbonate (2.80 g, 20.2 mmol) in DMF (35 mL) was added iodoethane (2.52 g, 16.2 mmol) dropwise at 0° C. The mixture was stirred at 30° C. for 16 h. The reaction mixture was diluted with water (100 mL) and extracted with EtOAc (3×35 mL). The combined organic layers were washed with brine (2×40 mL), dried over Na$_2$SO$_4$, filtered and concentrated to give a crude product (2.51 g, >100%) as a yellow oil, which was used to the next step directly.

$^1$H NMR (400 MHz, CDCl$_3$) δ: 6.87 (s, 1H), 4.36-4.44 (m, 4H), 4.15 (q, 2H), 1.94 (t, 3H), 1.41 (t, 3H), 1.33-1.39 (m, 6H).

Step 5: ethyl 5-chloro-6-(1,1-difluoroethyl)-2,4-diethoxypyridine-3-carboxylate

To a solution of ethyl 6-(1,1-difluoroethyl)-2,4-dihydroxypyridine-3-carboxylate (2.50 g, 8.24 mmol) in acetonitrile (30 mL) was added N-chlorosuccinimide (2.20 g, 16.5 mmol). The colorless reaction mixture was stirred at 100° C. for 16 h. The reaction mixture was diluted with water (120 mL) and aqueous saturated NaHCO$_3$ (30 mL). The product was extracted with EtOAc (3×40 mL). The combined organic layers were washed with brine (50 mL), dried over Na$_2$SO$_4$, filtered and concentrated. The crude product was purified by column chromatography eluting with EtOAc/petroleum ether (0:100 to 96:4) to give the title compound (2.1 g, 75%) as a light yellow oil.

$^1$H NMR (400 MHz, CDCl$_3$) δ: 4.33-4.34 (m, 4H), 4.21 (q, 2H), 2.02 (t, 3H), 1.35-1.46 (m, 9H).

Step 6: 5-chloro-6-(1,1-difluoroethyl)pyridine-2,4-diol

A solution of ethyl 5-chloro-6-(1,1-difluoroethyl)-2,4-diethoxypyridine-3-carboxylate (2.10 g, 6.21 mmol) in 48% aqueous hydrobromic acid (25 mL) was stirred at 110° C. for 48 h. The reaction mixture was concentrated and treated with ammonium hydroxide (6 mL). The reaction mixture was concentrated to give the title compound (3.1 g, >100%, 30% pure) as a light yellow solid.

$^1$H NMR (400 MHz, DMSO-d$_6$) δ: 6.36 (s, 1H), 1.93 (t, 3H).

Step 7: 3,4,6-trichloro-2-(1,1-difluoroethyl)pyridine

A mixture of 5-chloro-6-(1,1-difluoroethyl)pyridine-2,4-diol (1.80 g, 2.6 mmol, 30% pure) in phosphorus oxychloride (18 mL) and DMF (4.5 mL) was stirred at 100° C. for 16 h. The reaction mixture was poured into ice-water (80 mL) and extracted with EtOAc (3×40 mL). The combined organic layers were washed with brine (2×50 mL), dried over Na$_2$SO$_4$, filtered and concentrated. The crude product was purified using column chromatography eluting with EtOAc/petroleum ether (0:100 to 0.5:99.5) to give the title compound (540 mg, 85%) as a white solid.

$^1$H NMR (400 MHz, CDCl$_3$) δ: 7.56 (s, 1H), 2.08 (t, 3H).

Step 8: ethyl {(1R,5S,6S)-3-[3,6-dichloro-2-(1,1-difluoroethyl)pyridin-4-yl]-3-azabicyclo[3.1.0]hex-6-yl}acetate A mixture of 3,4,6-trichloro-2-(1,1-difluoroethyl)pyridine (50 mg, 0.2 mmol), ethyl (1R,5S,6S)-3-azabicyclo[3.1.0] hex-6-ylacetate (34 mg, 0.20 mmol) and triethylamine (62 mg, 0.61 mmol) in DMF (2 mL) was stirred at 60° C. for 16 h. The mixture was diluted with water (15 mL) and aqueous ammonium chloride (10 mL) and extracted with EtOAc (3×15 mL). The combined organics were washed with brine, dried over Na$_2$SO$_4$, filtered and concentrated. The crude product was purified using column chromatography eluting with EtOAc/petroleum ether (0:100 to 7:93) to give the title compound (70 mg) as a yellow solid.

$^1$H NMR (400 MHz, CD$_3$OD) δ: 6.84 (s, 1H), 4.13 (q, 2H), 4.02-4.08 (m, 2H), 3.45-3.54 (m, 2H), 2.33 (d, 2H), 1.97 (t, 3H), 1.57-1.62 (m, 2H), 1.25 (t, 3H), 0.99-1.06 (m, 1H).

Step 9

To a solution of ethyl {(1R,5S,6S)-3-[3,6-dichloro-2-(1,1-difluoroethyl)pyridin-4-yl]-3-azabicyclo[3.1.0]hex-6-yl}acetate (70 mg, 0.18 mmol) in dioxane (5 mL) was added (2S,3R)-3-hydroxy-2-methylazetidin-1-ium [(1R,4S)-7,7-dimethyl-2-oxobicyclo[2.2.1]hept-1-yl]methanesulfonate (64.3 mg, 0.200 mmol), sodium tert-butoxide (71.0 mg, 0.738 mmol), chloro(2-dicyclohexylphosphino-2',6'-di-i-propoxy-1,1'-biphenyl)[2-(2-aminoethylphenyl)]palladium (II) (6.73 mg, 0.00923 mmol) and 2-dicyclohexylphosphino-2',6'-diisopropoxybiphenyl (4.31 mg, 0.00923 mmol) under nitrogen. The reaction mixture was stirred at 70° C. for 16 h, then 80° C. for 40 h. The cooled reaction mixture was diluted with water, acidified to pH=5 with 2N HCl, and extracted with EtOAc (3×25 mL), the combined organics were washed with brine, dried over Na$_2$SO$_4$, filtered and concentrated. The crude product was purified using preparatory thin-layer chromatography and then purified using Prep. HPLC to give Example 12 (10.5 mg, 14%) as a white solid.

MS (ES+): 401.9 (M+H). $^1$H NMR (400 MHz, CD$_3$OD) δ: 5.78 (s, 1H), 4.09-4.15 (m, 2H), 3.88-3.96 (m, 3H), 3.41-3.47 (m, 1H), 3.18-3.24 (m, 2H), 2.26 (d, 2H), 1.92 (t, 3H), 1.49-1.51 (m, 2H), 1.46 (d, 3H), 1.14-1.18 (m, 1H).

Example 13: [(1R,5S,6R)-3-{2-[(2S,3R)-3-hydroxy-2-methylazetidin-1-yl]-5-methoxy-6-(trifluoromethyl)pyrimidin-4-yl}-3-azabicyclo[3.1.0]hex-6-yl] acetic acid

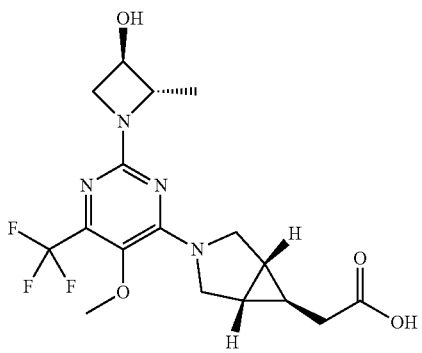 [SMILES: COc1c(N2C[C@@H]3[C@@H](CC(=O)O)[C@@H]3C2)nc(N2C[C@@H](O)[C@@H]2C)nc1C(F)(F)F]

To a solution of ethyl [(1R,5S,6R)-3-{5-bromo-2-[(2S,3R)-3-hydroxy-2-methylazetidin-1-yl]-6-(trifluoromethyl)pyrimidin-4-yl}-3-azabicyclo[3.1.0]hex-6-yl]acetate (50 mg, 0.13 mmol) in methanol (5.0 mL) was added sodium methoxide (16.9 mg, 0.313 mmol) and copper (I) bromide (2.2 mg, 0.016 mmol) and heated to 60° C. for 16 h. Additional copper (I) bromide (2.2 mg, 0.016 mmol) was added and the reaction heated at 60° C. for 16 h. The reaction mixture was diluted with aq. ammonium chloride solution and extracted with EtOAc (3×20 mL). The combined organic layers were washed with brine, dried over with Na$_2$SO$_4$, filtered and concentrated to give a crude product that was purified via reverse phase preparative HPLC to provide 20 mg (48% yield) of Example 13 as a white solid.

MS (ES+): 403.0 (M+H). 1H NMR (400 MHz, CD$_3$OD) δ: 4.19-3.97 (m, 5H), 3.64-3.57 (m, 3H), 3.57 (s, 3H), 2.30 (br. d, 2H), 1.57 (br. s, 2H), 1.46 (s, 3H), 0.91-0.81 (m, 1H).

Biological Data

A screening assay was developed for KHK involving a coupled enzyme system which used the product of the KHK reaction to drive an absorbance signal in kinetic mode. KHK takes fructose and ATP and converts it to F1P and ADP. ADP then serves as substrate to pyruvate kinase which converts PEP to pyruvate which is then reduced to lactate by lactate dehydrogenase with the concomitant oxidation of NADH to NAD$^+$. The resulting depletion of NADH was monitored by measuring absorbance at 340 nm.

Recombinant human KHK-C and KHK-A were expressed in E. coli as a His-tagged fusion protein and purified using Ni-NTA chromatography. The cDNA was synthesized based on NCBI refseq NP_006479.1 along with sequences for an N-terminal His-tag and a thrombin cleavage site, and cloned into pET28a(+) vector. The protein was expressed in BL-21 (DE3) using IPTG induction and purified using Ni-NTA column followed by Superdex 75. Purified KHK-C and KHK-A were treated with thrombin to remove the His-tag, and final cleanup was done using Ni-NTA/strapavidin affinity purification. The protein prep was ~95% pure on SDS-PAGE and the molecular weight was confirmed by mass spectrometry to be 32663 Da (expected 32667 Da).

In one assay, referred to as Assay A, a 384-well format on a Corning 3653 assay plate is used, and monitored by UV-vis spectroscopy in continuous mode at rt. Compounds were prepared in DMSO as 4 mM stocks, diluted using an 11-point half-log scheme on a Biomek FX (Beckman Coulter), and incubated at rt for 30 minutes with the reaction mixture containing 50 mM HEPES, pH 7.4, 140 mM KCl, 3.5 mM MgCl$_2$, 0.8 mM fructose, 2 mM TCEP, 0.8 mM PEP, 0.7 mM NADH, 0.01% Triton X-100, 30 U/mL pyruvate kinase-lactate dehydrogenase, and 10 nM purified KHK-C. The compound concentration in each well ranged from 1 nM to 100 μM. The reaction was initiated with the addition of 0.2 mM ATP. The absorbance was measured for 30 minutes on a SpectraMax reader (Molecular Devices) after ATP was added. The concentrations provided are based on the final mixture volume of 40 μL (referred to as the final concentration).

Controls: N8-(cyclopropylmethyl)-N4-(2-(methylthio)phenyl)-2-(piperazin-1-yl)pyrimido[5,4-d]pyrimidine-4,8-diamine at 2 μM final concentration was used as high percent effect (HPE) control, and 2.5% DMSO which was present in all reaction wells was used as zero percent effect (ZPE) control. Reaction rates were obtained for 300-1800 seconds time window in units of 1000*AU/min (absorbance unit per minute), and average values for ZPE and HPE controls from 16 wells each were calculated, AveZPE and AveHPE, respectively.

Percent inhibition (% inhibition) was calculated for each well using this equation:

$$100 - 100 \times \frac{(\text{Compound absorbance rate value} - Ave_{HPE})}{(Ave_{ZPE} - Ave_{HPE})}$$

The % inhibition was then plotted against the log of compound concentration using GraphPad Prism, and the data was fit to the equation "log[compound] vs. response—variable slope" using nonlinear regression analysis to give IC$_{50}$ values. For each compound tested, the IC$_{50}$ provided is the average based on at least two separate assays conducted on separate days.

Compounds having an IC$_{50}$ value less than 20 nM were examined in a second KHK assay, referred to as Assay B, using 10-fold less enzyme and measuring absorbance for 3 hours to obtain IC$_{50}$ values below the 10 nM lower limit of Assay A. Compounds were prepared in DMSO as 4 μM stocks, diluted using an 11-point 2-fold dilution scheme on a Biomek FX spanning a concentration range of 97 μM to 100 nM, and incubated with reaction mixture prepared in a similar manner as in Assay A but containing 1 nM KHK-C. The reaction was initiated with addition of 0.2 mM ATP, and the absorbance was monitored for 3 hours at 340 nm. Reaction rates and IC$_{50}$ values were calculated as described above.

A third KHK assay, referred to as Assay C, was performed at high fructose and ATP concentrations, conditions that would be more consistent with physiological concentrations of the natural substrates of the KHK enzyme. Assay C was conducted as described above for Assay B except using 8 mM fructose and 2 mM ATP, and compound concentration range of 10 μM to 1 μM or 50 μM to 5 μM using half-log dilution scheme.

A fourth assay, referred to as Assay D, was performed using human KHK-A to assess the potency of compounds in inhibiting activity of this enzyme. Compounds were prepared in DMSO as 4 μM stocks, diluted using an 11-point 2-fold dilution scheme on a Biomek FX spanning a final concentration range of 0.25 to 250 nM, and incubated with reaction mixture prepared in a similar manner as in Assay A but containing 8 mM fructose and 1 nM KHK-A. The reaction was initiated with addition of 0.2 mM ATP, and the absorbance was monitored for 3 hours at 340 nm. Reaction rates and $IC_{50}$ values were calculated as described above.

TABLE 3

Biological Data for Assays A, B, C and D[+]

| Example No. | $IC_{50}$ (nM) | | | |
|---|---|---|---|---|
| | Assay A 10 nM KHK-C | Assay B 1 nM KHK-C | Assay C 1 nM KHK-C | Assay D 1 nM KHK-A |
| 1 | 5.5 (6) | 1.5 (2) | 3.3 (6) | 7.3 (2) |
| 2 | 6.8 (2) | 1.5 (2) | 3.6 (2) | |
| 3 | 3,508 (2) | | | |
| 4 | 14.2 (16) | 8.4 (2) | 37.3 (10) | 66.0 (2) |
| 5 | 24.7 (6) | 13.6 (6) | 58.8 (10) | 95.5 (2) |
| 6 | 169.5 (2) | | | |
| 7 | 110.9 (2) | | | |
| 8 | 53.8 (3) | | | |
| 9 | 14,361 (2) | | | |

TABLE 3-continued

Biological Data for Assays A, B, C and D[+]

| Example No. | $IC_{50}$ (nM) | | | |
|---|---|---|---|---|
| | Assay A 10 nM KHK-C | Assay B 1 nM KHK-C | Assay C 1 nM KHK-C | Assay D 1 nM KHK-A |
| 10 | 682.1 (2) | | | |
| 11 | 866.1 (2) | | | |
| 12 | 288.8 (2) | | | |
| 13 | 33.9 (2) | | | |
| 24 | 9.7 (4) | 3.3 (2) | 11.0 (4) | 12.1 (2) |
| 40 | 11.1 (4) | 3.7 (2) | | 37.9 (2) |
| 42 | 8.8 (4) | 2.4 (4) | | 10.5 (2) |
| 43 | 17.8 (4) | 8.0 (4) | | 48.6 (2) |
| 50 | 4.4 (2) | 1.5 (2) | 2.6 (2) | |

[+]Avg $IC_{50}$ based on (#) number of runs per Example.

Figure 3:
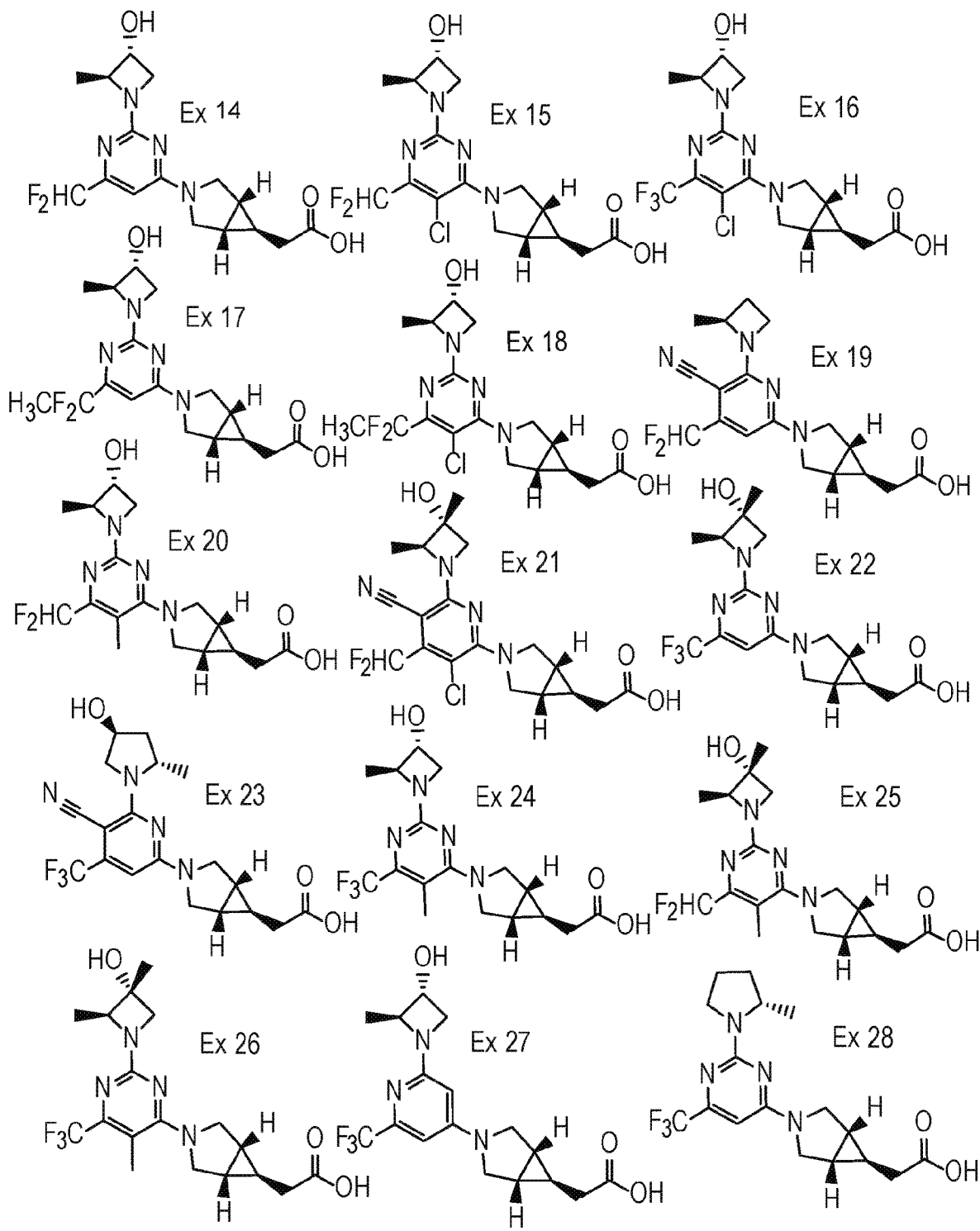
FIG. 3 provides structures of Examples from Table 4.
Figure 3:
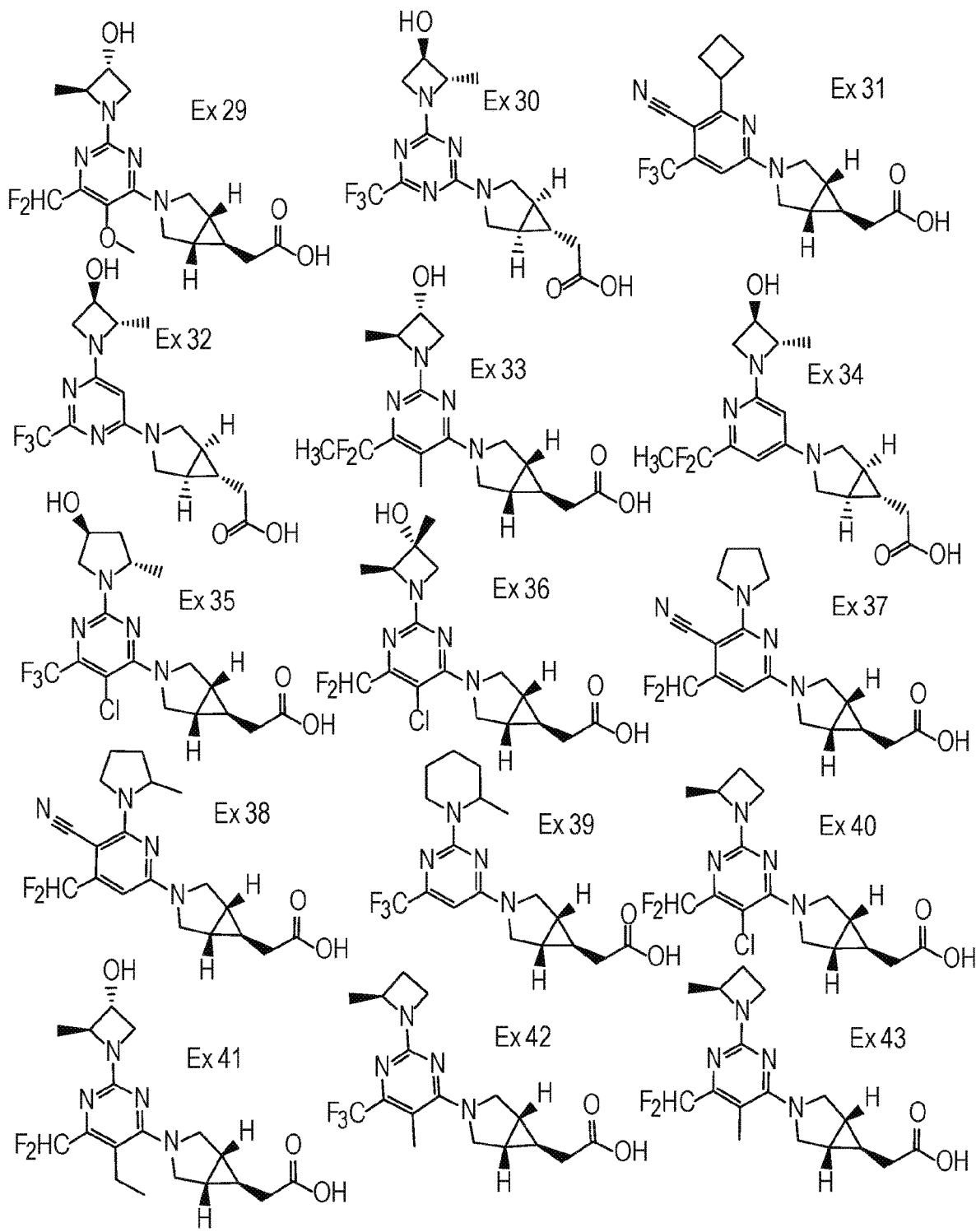
Figure 3:
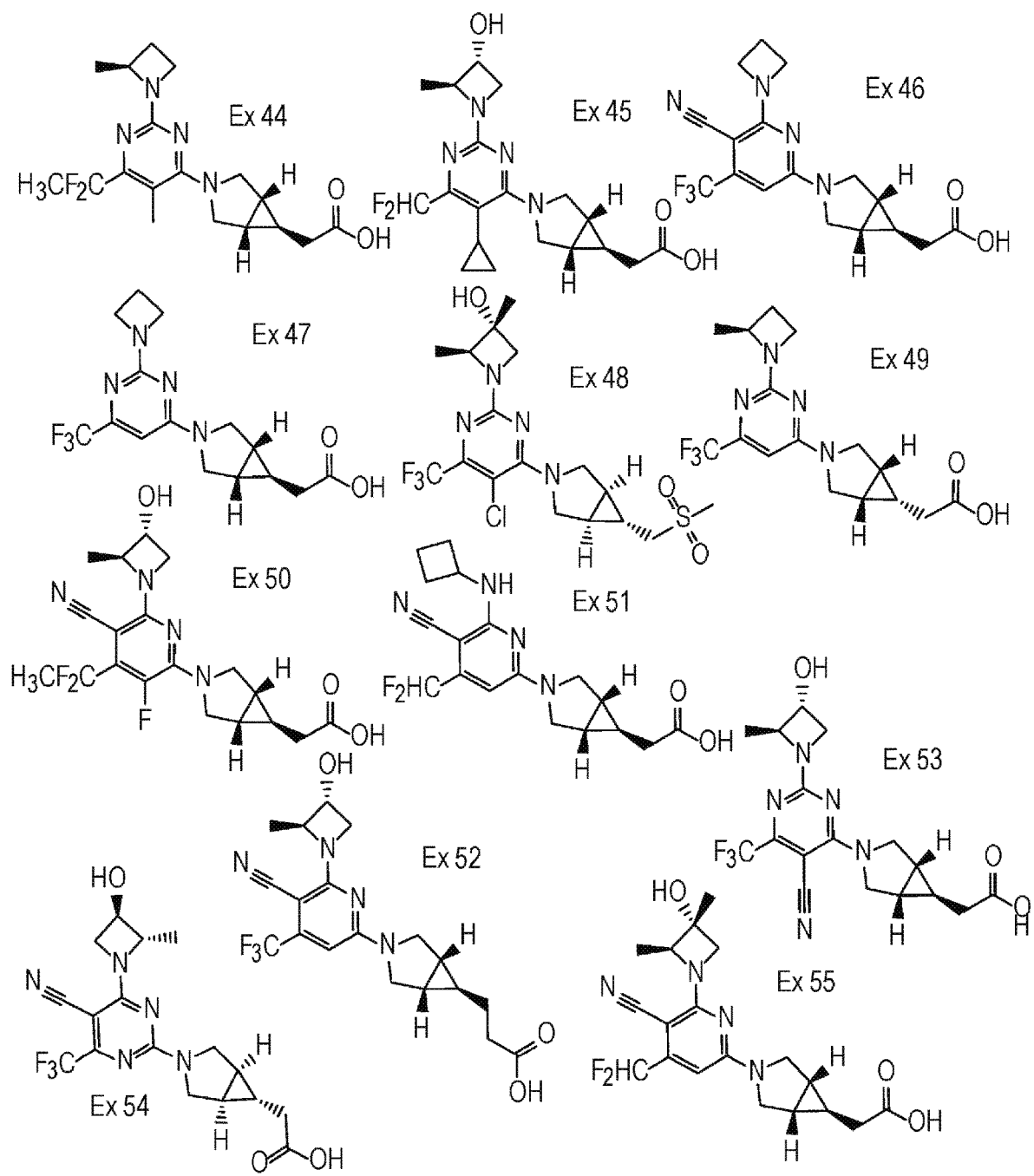

The following Examples presented in Table 4 were made using conditions similar to the referenced Examples listed in the column identified as "Ref. Ex. #", making non-critical, routine changes. Table 4 also contains biological data from Assay A for these Examples. Structures of these Examples from Table 4 are found in FIG. 3.

TABLE 4

Examples and Biological Data for Assay A

| Ex # | Name | NMR Data/LCMS Data | Ref. Ex. # | $IC_{50}$ (nM) Assay A[+] |
|---|---|---|---|---|
| Ex 14 | [(1R,5S,6R)-3-{6-(difluoromethyl)-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 6.30 (t, 1H), 6.03 (s, 1H), 4.21 (dd, 1H), 4.15-4.03 (m, 2H), 3.90 (br. s, 1H) 3.68-3.55 (m, 2H), 3.54-3.41 (m, 2H), 2.32 (d, 2H), 1.61 (br. s, 2H), 1.49 (d, 3H), 0.86-0.79 (m, 1H). MS (ES+): 355.0 (M + H). | Ex 1 | 152.2 (2) |
| Ex 15 | [(1R,5S,6R)-3-{5-chloro-6-(difluoromethyl)-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 6.75 (t, 1H), 4.26 (dd, 2H), 4.19 (dd, 1H), 4.13-4.00 (m, 2H), 3.72 (t, 2H), 3.64 (dd, 1H), 2.26 (d, 2H), 1.56 (br. s, 2H), 1.47 (d, 3H), 0.91-0.74 (m, 1H). MS (ES+): 389.0 (M + H). | Ex 2 | 19.1 (2) |
| Ex 16 | [(1R,5S,6R)-3-{5-chloro-2-[(2S,3R)-3-hydroxy-2-methylazetidin-1-yl]-6-(trifluoromethyl)pyrimidin-4-yl}-3-azabicyclo[3.1.0]hex-6-yl]acetic acid | $^1$H NMR (400 MHz, CD$_3$OD) δ: 4.27 (t, 2H), 4.21-4.14 (m, 1H), 4.14-4.00 (m, 2H), 3.74 (br. t, 2H), 3.65 (dd, 1H), 2.29 (d, 2H), 1.57 (br. s, 2H), 1.47 (d, 3H), 0.87-0.78 (m, 1H). MS (ES+): 406.9 (M + H). | Ex 2 | 6.4 (4) |
| Ex 17 | [(1R,5S,6R)-3-{6-(1,1-difluoroethyl)-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 6.00 (s, 1H), 4.26-4.15 (m, 1H), 4.14-3.99 (m, 2H), 3.88 (br. s, 1H), 3.62 (dd, 2H), 3.52-3.41 (m, 2H), 2.30 (d, 2H), 1.82 (t, 3H), 1.59 (br. s, 2H), 1.49 (d, 3H), 0.88-0.78 (m, 1H). MS (ES+): 369.1 (M + H). | Ex 1 | 131.4 (2) |
| Ex 18 | [(1R,5S,6R)-3-{5-chloro-6-(1,1-difluoroethyl)-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 4.27 (t, 2H), 4.20-3.94 (m, 3H), 3.73-3.65 (m, 2H), 3.62 (dd, 1H), 2.29 (d, 2H), 1.90 (t, 3H), 1.55 (br. s, 2H), 1.47 (d, 3H), 0.87-0.79 (m, 1H). MS (ES+): 403.2 (M + H). | Ex 2 | 16.7 (2) |
| Ex 19 | [(1R,5S,6R)-3-{5-cyano-4-(difluoromethyl)-6-[(2S)-2-methylazetidin-1-yl]pyridin-2-yl}-3-azabicyclo[3.1.0]hex-6-yl]acetic acid | $^1$H NMR (400 MHz, CD$_3$OD) δ: 6.86 (t, 1H), 6.02 (s, 1H), 4.68-4.53 (m, 1H), 4.39 (td, 1H), 4.12-4.01 (m, 1H), 3.90-3.60 (br. m, 2H), 3.57-3.41 (m, 2H), 2.51-2.36 (m, 1H), 2.31 (m, 2H), 2.05-1.93 (m, 1H), 1.61 (br. s, 2H), 1.49 (d, 3H), 0.86-0.79 (m, 1H). MS (ES+): 363.1 (M + H) | Ex 1 | 7.2 (4) |
| Ex 20 | [(1R,5S,6R)-3-{6-(difluoromethyl)-2-[(2S,3R)-3-hydroxy-2-methylazetidin-1-yl]-5-methylpyrimidin-4-yl}-3-azabicyclo[3.1.0]hex-6- | $^1$H NMR (400 MHz, CD$_3$OD) δ: 7.03 (t, 1H), 4.53-4.43 (m, 1H), 4.41-4.29 (m, 1H), 4.29-4.15 (m, 3H), 4.00-3.87 (m, 2H), 3.85 (dd, 1H), 2.37-2.30 (m, 5H), 1.70-1.64 (br. s, 2H), 1.52 (d, 3H), | Ex 1 | 33.4 (2) |

TABLE 4-continued

Examples and Biological Data for Assay A

| Ex # | Name | NMR Data/LCMS Data | Ref. Ex. # | IC$_{50}$ (nM) Assay A+ |
|---|---|---|---|---|
| | yl]acetic acid | 0.88-0.80 (m, 1H). MS (ES+): 368.9 (M + H). | | |
| Ex 21 | [(1R,5S,6R)-3-{3-chloro-5-cyano-4-(difluoromethyl)-6-[(2S,3R)-3-hydroxy-2,3-dimethylazetidin-1-yl]pyridin-2-yl}-3-azabicyclo[3.1.0]hex-6-yl]acetic acid | $^1$H NMR (400 MHz, CD$_3$OD) δ: 7.11 (t, 1H), 4.38-4.21 (m, 4H), 3.85 (d, 1H), 3.75 (dd, 2H), 2.29 (d, 2H), 1.61-1.55 (m, 2H), 1.41 (s, 3H), 1.40 (d, 3H), 0.88-0.81 (m, 1H). MS(ES+): 427.0 (M + H). | Ex 2 | 8.7 (2) |
| Ex 22 | [(1R,5S,6R)-3-{2-[(2S,3R)-3-hydroxy-2,3-dimethylazetidin-1-yl]-6-(trifluoromethyl)pyrimidin-4-yl}-3-azabicyclo[3.1.0]hex-6-yl]acetic acid | MS(ES+): 387.1 (M + H). Retention time: 2.190 min; Column: Waters Atlantis dC18 4.6 × 50 mm, 5 μm. Modifier: TFA 0.05%. Gradient: 95% water/5% acetonitrile linear to 5% water/95% acetonitrile over 4.0 min, HOLD at 5% water/95% acetonitrile for total run time of 5.0 min. Flow: 2.0 mL/min. | Ex 1 | 702.8 (2) |
| Ex 23 | [(1R,5S,6R)-3-{5-cyano-6-[(2S,4S)-4-hydroxy-2-methylpyrrolidin-1-yl]-4-(trifluoromethyl)pyridin-2-yl}-3-azabicyclo[3.1.0]hex-6-yl]acetic acid | MS(AP+): 411.1 (M + H); retention time = 1.62 min; Column: Waters XBridge C18 4.6 × 50, 5 μm Mobile phase A: 0.03% NH$_4$OH in H$_2$O (v/v); Mobile phase B: 0.03% NH$_4$OH in acetonitrile (v/v) Gradient: 95.0% H$_2$O/5.0% Acetonitrile linear to 5% H$_2$O/95% Acetonitrile in 4.0 min, HOLD at 5% H$_2$O/95% Acetonitrile for total run time of 5.0 min. Flow: 2 mL/min | Ex 1 | 11.6 (2) |
| Ex 24 | [(1R,5S,6R)-3-{2-[(2S,3R)-3-hydroxy-2-methylazetidin-1-yl]-5-methyl-6-(trifluoromethyl)pyrimidin-4-yl}-3-azabicyclo[3.1.0]hex-6-yl]acetic acid | $^1$H NMR (600 MHz, CD$_3$OD) δ: 4.15-4.22 (m, 1H), 4.02-4.14 (m, 4H), 3.56-3.67 (m, 3H), 2.32 (br. d, 2H), 2.20-2.23 (m, 3H), 1.54-1.57 (m, 2H), 1.50 (d, 3H), 0.87-0.94 (m, 1H). MS(ES+): 387.8 (M + H). | Ex 1 | 9.7 (4) |
| Ex 25 | [(1R,5S,6R)-3-{6-(difluoromethyl)-2-[(2S,3R)-3-hydroxy-2,3-dimethylazetidin-1-yl]-5-methylpyrimidin-4-yl}-3-azabicyclo[3.1.0]hex-6-yl]acetic acid | $^1$H NMR (400 MHz, CD$_3$OD) δ: 6.46 (m, 1H), 4.17-3.98 (m, 3H), 3.79 (d, 1H), 3.72 (d, 1H), 3.59 (dd, 2H), 2.29 (d, 2H), 2.23 (s, 3H), 1.53 (br. s, 2H), 1.46-1.31 (m, 6H), 0.93-0.84 (m, 1H). MS (ES+): 382.9 (M + H). | Ex 1 | 258.9 (2) |
| Ex 26 | [(1R,5S,6R)-3-{2-[(2S,3R)-3-hydroxy-2,3-dimethylazetidin-1-yl]-5-methyl-6-(trifluoromethyl)pyrimidin-4-yl}-3-azabicyclo[3.1.0]hex-6-yl]acetic acid | $^1$H NMR (400 MHz, CD$_3$OD) δ: 4.17-3.98 (m, 3H), 3.76 (dd, 2H), 3.58 (t, 2H), 2.28 (d, 2H), 2.19 (d, 3H), 1.53 (br. s, 2H), 1.45-1.30 (m, 6H), 0.94-0.81 (m, 1H). MS (ES+): 401.0 (M + H). | Ex 1 | 63.6 (2) |
| Ex 27 | [(1R,5S,6R)-3-{2-[(2S,3R)-3-hydroxy-2-methylazetidin-1-yl]-6-(trifluoromethyl)pyridin-4-yl}-3-azabicyclo[3.1.0]hex-6-yl]acetic acid | $^1$H NMR (400 MHz, CD$_3$OD) δ: 6.30 (d, 1H), 5.46 (s, 1H), 4.23-4.16 (m, 1H), 4.16-4.08 (m, 1H), 4.00-3.90 (m, 1H), 3.57 (dd, 2H), 3.50 (dd, 2H), 3.41-3.32 (m, 2H), 2.31 (d, 2H), 1.67-1.62 (m, 2H), 1.48 (d, 3H), 0.93-0.82 (m, 1H). MS (ES+): 371.9 (M + H) | Ex 1 | 109.4 (2) |
| Ex 28 | [(1R,5S,6R)-3-{2-[(2S)-2-methylpyrrolidin-1-yl]-6-(trifluoromethyl)pyrimidin-4-yl}-3-azabicyclo[3.1.0]hex-6-yl]acetic acid | $^1$H NMR (400 MHz, CD$_3$OD) δ: 5.97 (s, 1H), 4.26-4.18 (m, 1H), 3.93 (br. s, 1H), 3.72-3.40 (m, 5H), 2.32 (d, 2H), 2.15-1.94 (m, 2H), 1.94-1.81 (m, 1H), 1.74-1.64 (m, 1H), 1.60 (br. s, 2H), 1.24 (d, 3H), 0.87-0.79 (m, 1H). MS(ES+): 371.0 (M + H) | Ex 1 | 119.8 (2) |
| Ex 29 | [(1R,5S,6R)-3-{6-(difluoromethyl)-2-[(2S,3R)-3-hydroxy-2-methylazetidin-1-yl]-5-methoxypyrimidin-4-yl}-3-azabicyclo[3.1.0]hex-6-yl]acetic acid | $^1$H NMR (400 MHz, CD$_3$OD) δ: 6.71 (t, 1H), 4.23-3.97 (m, 5H), 3.61-3.54 (m, 3H), 3.58 (s, 3H), 2.30 (br. d, 2H), 1.56 (br. s, 2H), 1.47 (s, 3H), 0.90-0.82 (m, 1H). MS(ES+): 384.9(M + H) | Ex 13 | 264.9 (2) |
| Ex 30 | [(1R,5S,6R)-3-{4-[(2S,3R)-3-hydroxy-2-methylazetidin-1-yl]-6-(trifluoromethyl)-1,3,5-triazin-2-yl}-3-azabicyclo[3.1.0]hex-6-yl]acetic acid | $^1$H NMR (400 MHz, CD$_3$OD) δ: 4.32-4.22 (m, 1H), 4.22-4.10 (m, 2H), 3.97-3.85 (m, 2H), 3.73 (dd, 1H), 3.55-3.42 (m, 2H), 2.41-2.21 (m, 2H), 1.56 (br. s, 2H), 1.50 (d, 3H), 0.85-0.68 (m, 1H). MS(ES+): 373.9 (M + H) | Ex 1 | 509.2 (2) |
| Ex 31 | {(1R,5S,6s)-3-[5-cyano-6-cyclobutyl-4-(trifluoromethyl)pyridin-2-yl]-3-azabicyclo[3.1.0]hex-6- | $^1$H NMR (400 MHz, CD$_3$OD) δ: 6.59 (s, 1H), 4.26-4.05 (m, 1H), 4.02-3.88 (m, 1H), 3.81-3.53 (m, 3H), 2.39-2.52 (m, 2H) 2.39-2.28 (m, 4H), 2.16-2.03 (m, | Ex 6 | 30.0 (2) |

TABLE 4-continued

Examples and Biological Data for Assay A

| Ex # | Name | NMR Data/LCMS Data | Ref. Ex. # | IC$_{50}$ (nM) Assay A+ |
|---|---|---|---|---|
| | yl}acetic acid | 1H), 1.99-1.86 (m, 1H), 1.75-1.62 (m, 2H), 0.92-0.83 (m, 1H). MS(ES+): 365.9 (M + H). | | |
| Ex 32 | [(1R,5S,6R)-3-{6-[(2S,3R)-3-hydroxy-2-methylazetidin-1-yl]-2-(trifluoromethyl)pyrimidin-4-yl}-3-azabicyclo[3.1.0]hex-6-yl]acetic acid | $^1$H NMR (400 MHz, CD$_3$OD) δ: 5.18 (s, 1H), 4.25-4.18 (m, 1H), 4.18-4.12 (m, 1H), 4.11-4.03 (m, 1H), 3.73 (br. m, 2H), 3.57 (dd, 1H), 3.42 (br. d, 2H), 2.31 (d, 2H), 1.59 (br. s, 2H), 1.48 (d, 3H), 0.86-0.79 (m, 1H). MS(ES+): 372.9 (M + H) | Ex 1 | 1,760.4 (2) |
| Ex 33 | [(1R,5S,6R)-3-{6-(1,1-difluoroethyl)-2-[(2S,3R)-3-hydroxy-2-methylazetidin-1-yl]-5-methylpyrimidin-4-yl}-3-azabicyclo[3.1.0]hex-6-yl]acetic acid | $^1$H NMR (400 MHz, CD$_3$OD) δ: 4.24-3.91 (m, 5H), 3.68-3.44 (m, 3H), 2.27 (d, 2H), 2.20 (br. s, 3H), 1.90 (t, 3H), 1.58-1.41 (m, 5H), 0.91 (br. s, 1H). MS (ES+): 382.9 (M + H). | Ex 1 | 113.6 (4) |
| Ex 34 | [(1R,5S,6R)-3-{2-(1,1-difluoroethyl)-6-[(2S,3R)-3-hydroxy-2-methylazetidin-1-yl]pyridin-4-yl}-3-azabicyclo[3.1.0]hex-6-yl]acetic acid | $^1$H NMR (400 MHz, CD$_3$OD) δ: 6.27 (s, 1H), 5.40 (s, 1H), 4.19 (t, 1H), 4.09-4.14 (m, 1H), 3.91-3.98 (m, 1H), 3.54-3.58 (m, 2H), 3.48 (dd, 1H), 3.32-3.36 (m, 2H), 2.30 (d, 2H), 1.86 (t, 3H), 1.61-1.64 (m, 2H), 1.47 (t, 3H), 0.85-0.89 (m, 1H). MS(ES+): 368.0 (M + H). | Ex 12 | 331.4 (2) |
| Ex 35 | [(1R,5S,6R)-3-{5-chloro-2-[(2S,4S)-4-hydroxy-2-methylpyrrolidin-1-yl]-6-(trifluoromethyl)pyrimidin-4-yl}-3-azabicyclo[3.1.0]hex-6-yl]acetic acid | MS (ES+): 421.32 (M + H). Retention time = 4.1336; SFC Column: Lux Cell 3 4.6 × 100 mm 5 μm. Modifier A: CO$_2$, Modifier B: Methanol with 0.2% NH$_4$OH. Gradient: 85:15 A: B, hold for 6 minutes. Column Temp = 40° C. Back Pressure: 120 Bar. Flow: 1.5 mL/min. | Ex 2 | 187.5 (2) |
| Ex 36 | [(1R,5S,6R)-3-{5-chloro-6-(difluoromethyl)-2-[(2S,3R)-3-hydroxy-2,3-dimethylazetidin-1-yl]pyrimidin-4-yl}-3-azabicyclo[3.1.0]hex-6-yl]acetic acid | $^1$H NMR (400 MHz, CD$_3$OD) δ: 6.75 (t, 1H), 4.25 (dd, 2H), 4.14 (q, 1H), 3.88-3.65 (m, 4H), 2.30 (d, 2H), 1.57 (br. s, 2H), 1.47-1.31 (m, 6H), 0.88-0.78 (m, 1H). MS (ES+): 402.9 (M + H). | Ex 2 | 102.8 (2) |
| Ex 37 | {(1R,5S,6s)-3-[5-cyano-4-(difluoromethyl)-6-(pyrrolidin-1-yl)Pyridin-2-yl]-3-azabicyclo[3.1.0]hex-6-yl}acetic acid | MS (API+): 363 (M + H). Retention time: 3.218. Method 1* | Ex 1 | 58.3 (4) |
| Ex 38 | {(1R,5S,6s)-3-[5-cyano-4-(difluoromethyl)-6-(2-methylpyrrolidin-1-yl)pyridin-2-yl]-3-azabicyclo[3.1.0]hex-6-yl}acetic acid | MS (API+): 377 (M + H). Retention time: 3.325. Method 1* | Ex 1 | 25.3 (4) |
| Ex 39 | {(1R,5S,6s)-3-[2-(2-methylpiperidin-1-yl)-6-(trifluoromethyl)pyrimidin-4-yl]-3-azabicyclo[3.1.0]hex-6-yl}acetic acid | MS (API+): 385 (M + H). Retention time = 3.528. Method 2** | Ex 1 | 24.8 (2) |
| Ex 40 | [(1R,5S,6R)-3-{5-chloro-6-(difluoromethyl)-2-[(2S)-2-methylazetidin-1-yl]pyrimidin-4-yl}-3-azabicyclo[3.1.0]hex-6-yl]acetic acid | $^1$H NMR (400 MHz, CD$_3$OD) δ: 6.74 (t, 1H), 4.45-4.35 (m, 1H), 4.25 (t, 2H), 3.98 (dt, 1H), 3.89 (q, 1H), 3.72 (br. t, 2H), 2.45-2.33 (m, 1H), 2.30 (d, 2H), 2.00-1.89 (m, 1H), 1.61-1.53 (m, 2H), 1.47 (d, 3H), 0.87-.080 (m, 1H). MS(ES+): 373.1 (M + H). | Ex 2 | 11.1 (4) |
| Ex 41 | [(1R,5S,6R)-3-{6-(difluoromethyl)-5-ethyl-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 6.52 (t, 1H), 4.20-4.14 (m, 1H), 4.09 (q, 1H), 4.05-3.93 (m, 3H), 3.66-3.56 (m, 3H), 2.75 (q, 2H), 2.34-2.27 (br. m, 2H), 1.57 (br. s, 2H), 1.48 (d, 3H), 1.03 (t, 3H), 0.93-0.85 (m, 1H). MS(ES+): 382.9 (M + H). | Ex 8 | 110.7 (2) |
| Ex 42 | [(1R,5S,6R)-3-{5-methyl-2-[(2S)-2-methylazetidin-1-yl]-6-(trifluoromethyl)pyrimidin-4-yl}-3-azabicyclo[3.1.0]hex-6-yl]acetic acid | $^1$H NMR (400 MHz, CDCl$_3$) δ: 4.34-4.43 (m, 1H), 3.95-4.09 (m, 3H), 3.86-3.95 (m, 1H), 3.48-3.61 (m, 2H), 2.30-2.40 (m, 3H), 2.16 (s, 3H), 1.89-2.00 (m, 1H), 1.45-1.54 (m, 5H), 0.95-1.04 (m, 1H). MS(ES+): 371.1 (M + H). | Ex 1 | 8.8 (4) |
| Ex 43 | [(1R,5S,6R)-3-{6-(difluoromethyl)-5-methyl-2- | $^1$H NMR (400 MHz, CD$_3$OD) δ: 6.45 (t, 1H), 4.43-4.28 (m, 1H), 4.06 (dd, 2H), | Ex 1 | 17.8 (4) |

TABLE 4-continued

Examples and Biological Data for Assay A

| Ex # | Name | NMR Data/LCMS Data | Ref. Ex. # | IC$_{50}$ (nM) Assay A+ |
|---|---|---|---|---|
| | [(2S)-2-methylazetidin-1-yl]pyrimidin-4-yl}-3-azabicyclo[3.1.0]hex-6-yl]acetic acid | 3.94 (td, 1H), 3.85 (q, 1H), 3.64-3.50 (m, 2H), 2.36 (dtd, 1H), 2.28 (d, 2H), 2.21 (t, 3H), 2.00-1.88 (m, 1H), 1.51 (br. s, 2H), 1.47 (d, 3H), 0.99-0.81 (m, 1H). MS (ES+): 353.1 (M + H). | | |
| Ex 44 | [(1R,5S,6R)-3-{6-(1,1-difluoroethyl)-5-methyl-2-[(2S)-2-methylazetidin-1-yl]pyrimidin-4-yl}-3-azabicyclo[3.1.0]hex-6-yl]acetic acid | $^1$H NMR (400 MHz, CD$_3$OD) δ: 4.43-4.21 (m, 1H), 4.02 (t, 2H), 3.94-3.77 (m, 2H), 3.49 (t, 2H), 2.40-2.29 (m, 1H), 2.26 (d, 2H), 2.19 (br. s, 3H), 1.93 (m, 4H), 1.47 (m, 5H), 0.98-0.87 (m, 1H). MS (ES+): 367.3 (M + H). | Ex 1 | 51.4 (4) |
| Ex 45 | [(1R,5S,6R)-3-{5-cyclopropyl-6-(difluoromethyl)-2-[(2S,3R)-3-hydroxy-2-methylazetidin-1-yl]pyrimidin-4-yl}-3-azabicyclo[3.1.0]hex-6-yl]acetic acid | $^1$H NMR (400 MHz, CD$_3$OD) δ: 7.04 (t, 1H), 4.27-4.18 (m, 3H), 4.11-4.03 (m, 2H), 3.65-3.51 (m, 3H), 2.30 (d, 2H), 1.86-1.75 (m, 1H), 1.54-1.50 (m, 2H), 1.47 (d, 3H), 1.04-0.97 (m, 2H), 0.95-0.87 (m, 1H), 0.47-0.41 (m, 2H). MS(ES+): 395.0 (M + H). | Ex 7 | 237.8 (2) |
| Ex 46 | {(1R,5S,6s)-3-[6-(azetidin-1-yl)-5-cyano-4-(trifluoromethyl)pyridin-2-yl]-3-azabicyclo[3.1.0]hex-6-yl}acetic acid | $^1$H NMR (400 MHz, CD$_3$OD) δ: 6.07 (s, 1H), 4.29 (t, 4H), 4.04-3.56 (br. m, 2H), 3.51 (dd, 2H), 2.41-2.27 (m, 4H), 1.62 (br. s, 2H), 0.87-0.74 (m, 1H). MS (ES+): 366.8 (M + H). | Ex 1 | 21.5 (2) |
| Ex 47 | {(1R,5S,6s)-3-[2-(azetidin-1-yl)-6-(trifluoromethyl)pyrimidin-4-yl]-3-azabicyclo[3.1.0]hex-6-yl}acetic acid | $^1$H NMR (400 MHz, CD$_3$OD) δ: 6.30 (s, 1H), 4.18 (t, 4H), 4.05-3.93 (m, 1H), 3.79-3.70 (m, 1H), 3.65-3.50 (m, 2H), 2.43-2.34 (m, 2H), 2.33 (d, 2H), 1.70-1.59 (m, 2H), 0.87-0.79 (m, 1H). MS (ES+): 342.9 (M + H). | Ex 1 | 619.1 (2) |
| Ex 48 | (2S,3R)-1-[5-chloro-4-{(1R,5S,6S)-6-[(methylsulfonyl)methyl]-3-azabicyclo[3.1.0]hex-3-yl}-6-(trifluoromethyl)pyrimidin-2-yl]-2,3-dimethylazetidin-3-ol | $^1$H NMR (400 MHz, CD$_3$OD) δ: 4.42-4.27 (m, 2H), 4.21-4.10 (m, 1H), 3.89-3.70 (m, 4H), 3.17 (d, 2H), 3.01 (s, 3H), 1.86 (d, 2H), 1.50-1.33 (m, 6H), 1.06-0.93 (m, 1H). MS(ES+): 455.0 (M + H). | Ex 1 | 1,359 (2) |
| Ex 49 | [(1R,5S,6S)-3-{2-[(2S)-2-methylazetidin-1-yl]-6-(trifluoromethyl)pyrimidin-4-yl}-3-azabicyclo[3.1.0]hex-6-yl]acetic acid | $^1$H NMR (400 MHz, CD$_3$OD) δ: 6.05 (s, 1H), 4.49-4.37 (m, 1H), 4.00 (dt, 1H), 3.95-3.85 (m, 1H), 3.77-3.54 (m, 3H), 3.42 (br. d, 1H), 2.40 (dddd, 1H), 2.12 (d, 2H), 2.01-1.79 (m, 3H), 1.48 (d, 3H), 1.38-1.29 (m, 1H). MS(ES+): 356.9 (M + H). | Ex 1 | 2084 (4) |
| Ex 50 | [(1R,5S,6R)-3-{5-cyano-4-(1,1-difluoroethyl)-3-fluoro-6-[(2S,3R)-3-hydroxy-2-methylazetidin-1-yl]pyridin-2-yl}-3-azabicyclo[3.1.0]hex-6-yl]acetic acid | $^1$H NMR (400 MHz, CD$_3$OD) δ: 4.71-4.64 (m, 1H), 4.24-4.30 (m, 1H), 4.16-4.11 (m, 1H), 4.09-3.98 (m, 2H), 3.78-3.62 (m, 3H), 2.35 (d, 2H), 1.99 (t, 3H), 1.66-1.60 (m, 2H), 1.47 (d, 3H), 0.92-0.87 (m, 1H). MS(ES+): 411.1 (M + H). | Ex 1 | 4.4 (2) |
| Ex 51 | {(1R,5S,6s)-3-[5-cyano-6-(cyclobutylamino)-4-(difluoromethyl)pyridin-2-yl]-3-azabicyclo[3.1.0]hex-6-yl}acetic acid | MS (API+): 363 (M + H). Retention time = 3.226. Method 2** | Ex 1 | 150.4 (4) |
| Ex 52 | 3-[(1R,5S,6R)-3-{5-cyano-6-[(2S,3R)-3-hydroxy-2-methylazetidin-1-yl]-4-(trifluoromethyl)pyridin-2-yl}-3-azabicyclo[3.1.0]hex-6-yl]propanoic acid | $^1$H NMR (400 MHz, CD$_3$OD) δ: 6.13 (s, 1H), 4.66 (ddd, 1H), 4.34-4.23 (m, 1H), 4.14 (dt, 1H), 4.01-3.78 (br. m, 1H), 3.78 (dd, 1H), 3.68-3.40 (m, 3H), 2.40 (t, 2H), 1.65-1.52 (m, 4H), 1.49 (d, 3H), 0.60 (tt, 1H). MS(ES+): 411.0 (M + H). | Ex 1; | 82.5 (2) |
| Ex 53 | [(1R,5S,6R)-3-{5-cyano-2-[(2S,3R)-3-hydroxy-2-methylazetidin-1-yl]-6-(trifluoromethyl)pyrimidin-4-yl}-3-azabicyclo[3.1.0]hex-6-yl]acetic acid | MS(ES+): 398.3 (M + H); Retention time: 2.1964. Method 3*** | Ex 1 | 21.0 (2) |
| Ex 54 | [(1R,5S,6R)-3-{5-cyano-4-[(2S,3R)-3-hydroxy-2-methylazetidin-1-yl]-6-(trifluoromethyl)pyrimidin-2-yl}-3-azabicyclo[3.1.0]hex-6-yl]acetic acid | MS(ES+): 398.2 (M + H); retention time: 2.6397. Method 3*** | Ex 1 | 19.0 (2) |

TABLE 4-continued

Examples and Biological Data for Assay A

| Ex # | Name | NMR Data/LCMS Data | Ref. Ex. # | IC$_{50}$ (nM) Assay A[+] |
|---|---|---|---|---|
| Ex 55 | [(1R,5S,6R)-3-{5-cyano-4-(difluoromethyl)-6-[(2S,3R)-3-hydroxy-2,3-dimethylazetidin-1-yl]pyridin-2-yl}-3-azabicyclo[3.1.0]hex-6-yl]acetic acid | $^1$H NMR (600 MHz, CD$_3$OD) δ: 6.69 (t, 1H), 6.08 (s, 1H), 4.35 (q, 1H), 4.26 (d, 1H), 4.10-3.93 (br. s, 1H), 3.87 (d, 1H), 3.74-3.43 (m, 3H), 2.32 (d, 2H), 1.69-1.55 (m, 2H), 1.44-1.38 (m, 6H), 0.87-0.81 (m, 1H). MS(ES+): 392.9 (M + H). | Ex 1 | 13.7 (2) |

[+]Avg IC$_{50}$ based on (#) number of runs per Example.
*Examples 37 and 38 use Method 1: Column: Xbridge C18 2.1 × 50 mm 5 μm. Temperature: 40° C. Mobile Phase A: 0.0375% TFA in H$_2$O. Mobile Phase B: 0.01875% TFA in acetonitrile. Initial conditions: B: 1%, A: 99%. Gradient: B: 1%, A: 99% to B: 5%, A: 95% from t = 0.00 min to 0.60 min, then to B: 100% from t = 0.60 min to 4.00 min, then to B: 1%, A: 99% from t = 4.00 min to 4.30 min, hold until t = 4.70 min. Flow rate = 0.8 mL/min, 2 μL injection volume.
**Examples 39 and 51 use Method 2: Column: Xbridge C18 2.1 × 50 mm 5 μm. Temperature: 40° C. Mobile Phase A: 0.0375% TFA in H$_2$O. Mobile Phase B: 0.01875% TFA in acetonitrile. Initial conditions: B: 10%, A: 90%. Hold from t = 0.00 min to 0.50 min. Gradient: B: 10%, A: 90% to B: 100%, A: 0% from t = 0.50 min to 4.00 min, then to B: 10%, A: 90% from t = 4.00 min to 4.30 min, hold until t = 4.70 min. Flow rate = 0.8 mL/min, 2 μL injection volume.
***Examples 53 and 54 use Method 3: Column: OJ-H 4.6 × 100 mm, 5 μm; Mobile phase A: Methanol (v/v); Mobile phase B: CO$_2$ (v/v). Gradient: 80.0% CO$_2$/20.0% Methanol Isocratic over 5 min. Flow: 1.5 mL/min. Back Pressure: 100 Bar.

It is claimed:

1. A method of treating a disease for which an inhibitor of KHK is indicated, the method comprising the administration to a human in need thereof a therapeutically effective amount of a compound, wherein the compound is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid, or pharmaceutically acceptable salt thereof, and wherein the disease is selected from any one or a combination of obesity, visceral adipose dysfunction, eating disorders, and excessive sugar craving.

2. The method of claim 1, wherein the compound is a crystalline form of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid.

3. The method of claim 2, wherein the crystalline form is characterized substantially by the following principal powder x-ray diffraction pattern peaks expressed in terms of 2θ as measured with a copper radiation chosen from 9.0+/−0.2°, 10.4+/−0.2°, 15.0+/−0.2°, and 21.4+/−0.2°.

4. The method of claim 1, wherein the compound is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid.

5. The method of claim 4, wherein the disease is obesity.

6. The method of claim 4, wherein the disease is visceral adipose dysfunction.

7. The method of claim 4, wherein the disease is eating disorders.

8. The method of claim 4, wherein the disease is excessive sugar craving.

* * * * *